(12) United States Patent
Norris et al.

(10) Patent No.: US 6,239,285 B1
(45) Date of Patent: May 29, 2001

(54) PROCESS FOR MAKING 5-LIPOXYGENASE INHIBITORS HAVING VARIED HETEROCYCLIC RING SYSTEMS

(75) Inventors: Timothy Norris, Gales Ferry, CT (US); Megan E. Hnatow, Charlestown, MA (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/606,318

(22) Filed: Jun. 29, 2000

Related U.S. Application Data

(62) Continuation of application No. 09/207,342, filed on Dec. 8, 1998, now Pat. No. 6,063,928, which is a division of application No. 09/020,014, filed on Feb. 6, 1998, now Pat. No. 5,883,106, which is a continuation of application No. 08/809,901, filed as application No. PCT/IB95/00408 on Jun. 13, 1997, now abandoned.
(60) Provisional application No. 60/151,610, filed on Aug. 31, 1999.

(51) Int. Cl.$^7$ .................... C07D 231/12; C07D 231/56; C07D 233/04; C07D 235/18
(52) U.S. Cl. .................... 548/304.7; 548/311.1; 548/362.5; 548/365.7
(58) Field of Search .................... 548/304.7, 311.1, 548/362.5, 365.7

(56) References Cited

U.S. PATENT DOCUMENTS

| | | | |
|---|---|---|---|
| 4,739,084 | 4/1988 | Takaya et al. | 556/21 |
| 4,739,085 | 4/1988 | Takaya et al. | 556/21 |
| 4,764,629 | 8/1988 | Sayo et al. | 556/23 |
| 4,766,277 | 8/1988 | Bigelow, Jr. | 200/293 |
| 4,961,037 | 10/1990 | Orii et al. | 318/696 |
| 4,994,607 | 2/1991 | Chan | 562/496 |

FOREIGN PATENT DOCUMENTS

| | | |
|---|---|---|
| 9015790 | 12/1990 | (WO) . |
| 9209552 | 6/1992 | (WO) . |
| 9522405 | 8/1995 | (WO) . |
| 9611911 | 4/1996 | (WO) . |
| 9621507 | 7/1996 | (WO) . |
| 9924410 | 5/1999 | (WO) . |

OTHER PUBLICATIONS

Migita, et al., *Bull. Chem. Soc. Japan*, vol. 53, pp. 1385–1389 (1980).
Trost, et al., *J. Amer. Chem. Soc.*, 102, pp. 7932–7934 (1980).
Tani, et al, *J. Chem. Soc. Chem. Commun.*, 600 (1982).
Miyashita, et al., *Tetrahedron*, 40(8), pp. 1245–1253 (1984).
Tani, et al., *Angew Chem. Int. Ed. Engl.*, 24(3), pp. 217–219 (1985).
Noyori, et al., *J. Am. Chem. Soc.*, vol. 109, pp. 5856 (1987).
Takagi, *Chemistry Letters*, pp. 2221–2224 (1987).
Mieczyslaw Makosza,*Advances in Catalysis*, vol. 35, pp. 375–422 (1987).

(List continued on next page.)

*Primary Examiner*—Joseph K. McKane
*Assistant Examiner*—Taofiq A. Solola
(74) *Attorney, Agent, or Firm*—Peter C. Richardson; Paul H. Ginsburg; Raymond M. Speer

(57) ABSTRACT

A process is described for preparing a compound of Formula (1.3.0):

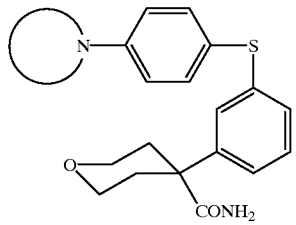

(1.3.0)

where

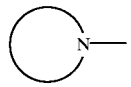

(1.3.1)

is:

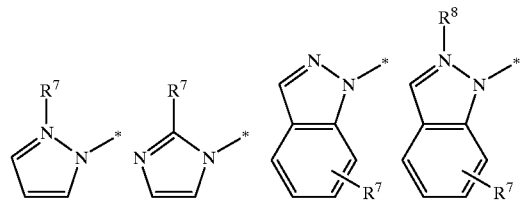

comprising: establishing a reaction mixture consisting of

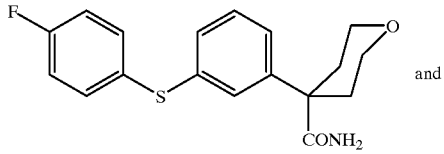

(2.0.0)
and

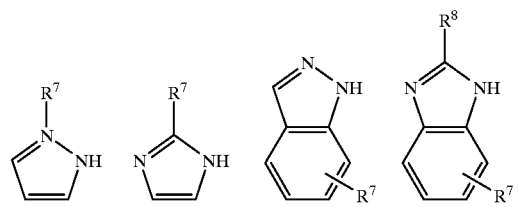

in an aprotic solvent; in the presence of NaOH or KOH; optionally in the presence of a phase transfer catalyst, especially a quaternary ammonium salt or a phosphonium salt; followed by heating said reaction mixture under a nitrogen atmosphere.

1 Claim, No Drawings

OTHER PUBLICATIONS

Naruta, et al., *Tetrahedron Letters*, 28, pp. 4553–4556 (1987).
Hayashi, et al., *J. Am. Chem. Soc.*, 110, pp. 5579–5581 (1988).
Jan–E. Backvall, *Advances in Metal–Organic Chemistry*, vol. 1, pp. 135–175 (1989).
Hayashi, et al., *J. Am. Chem. Soc.*, 111, pp. 3426–3428 (1989).
Morgan, et al., *J. Med. Chem.*, vol. 33, pp. 1091–1097 (1990).
Ryoji Noyori, *Science*, vol. 248, pp. 1194–1199 (1990).
Kollar, et al., *J. Molecular Catalysis*, 67, pp. 191–198 (1991).
Yamaguchi, et al., *Tetrahedron Asymmetry*, 2(7), pp. 663–666 (1991).
Burgess, et al., *Tetrahedron Asymmetry*, 2(7), pp. 613–621 (1991).
Kagechika, et al., *J. Org. Chem.*, 56, pp. 4093–4094 (1991).
Sakamoto, et al., *Tetrahedron Letters*, 33, pp. 6845–6848 (1992).
Ozawa, et al., *Tatrahedron Letters*, 33(11), pp. 1485–1488 (1992).
Ozawa, et al, *Chemistry Letters*, pp. 2177–2180 (1992).
Brocato, et al., *Tetrahedron Lett.*, vol. 33, pp. 7433–7436 (1992).
Wu, et al., *Tetrahedron Letters*, 33, pp. 6331–6334 (1992).
Murakami, et al., *Bull. Chem. Soc. Jpn.*, 65, pp. 3095–3102 (1992).
Collman, et al., *J. Chem. Soc. Chem. Commun.*, pp. 1647–1649 (1992).
Collman, et al., *J. Chem. Soc. Chem. Commun.*, p. 428 (1993).
Arcadi, et al., *Tetrahedron Lett.*, vol. 34, pp. 2813–2816 (1993).
Brunner, et al., *J. Organometallic Chem.*, 456, pp. 71–75 (1993).
McClure, et al., *J. Amer. Chem. Soc.*, vol. 115, pp. 6094–6100 (1993).
Nuss, et al., *J. Am. Chem. Soc.*, vol. 115, pp. 6691–6692 (1993).
Ozawa, et al., *Tetrahedron Letters*, 34(15), pp. 2505–2508 (1993).
Paquette, et al., *J. Org. Chem.*, vol. 58, pp. 165–169 (1993).
Wu, et al., *Tetrahedron Letters*, 34(37), pp. 5927–5930 (1993).
Waldman, et al., ACS Symposium Series, 517 (1993), M. E. Davis and S. L. Snib, Eds.
Ozawa, et al., ACS Symposium Series, 517 (1993), M. E. Davis and S. L. Snib, Eds.
Chan, et al., ACS Symposium Series, 517 (1993), M. E. Davis and S. L. Snib, Eds.
Desponds, et al., *Journal of Organometallic Chemistry*, vol. 507, pp. 257–261 (1996).
Classics in Total Synthesis, K. C. Nicolaou and E. J. Sorensen, p. 567, VCH 1996, Weinheim, Germany, New York, USA, Basel, Switzerland, Cambridge, England, Tokyo, Japan.
Mann, et al. in *J. Am. Chem. Soc.* 120, 9205–9219 (1998).
Cao. et al., *Org. Synth.*, vol. 76, pp. 6–11 (1999).

PROCESS FOR MAKING 5-LIPOXYGENASE INHIBITORS HAVING VARIED HETEROCYCLIC RING SYSTEMS

REFERENCE TO APPLICATIONS

This application is continuation of Ser. No. 09/207,342 filed Dec. 8, 1998; now U.S. Pat. No. 6,063,928 which is a divisional of application Ser. No. 09/020,014 filed Feb. 6, 1998, now U.S. Pat. No. 5,883,106; which is a continuation of application Ser. No. 08/809,901 filed May 29, 1995, now abandoned; This application also claims the benefit of Ser. No. 60/151,610, Aug. 31, 1999; claiming priority from application Ser. No. PCT/JP94/01747 filed Oct. 18, 1994, now abandoned; and a § 371 of application Ser. No. PCT/IB95/00408 filed May 29, 1995, now lapsed, and published as WO 96/11911 on Apr. 25, 1996, which discloses 5-lipoxygenase inhibitors useful in the treatment of inflammatory diseases and allergy. Several processes for preparing said 5-lipoxygenase inhibitors are described therein, but nothing that is disclosed would teach the person of ordinary skill the improved process of the present invention.

Reference is also made to copending application Ser. No. 60/113,221 filed Dec. 22, 1998, which discloses a novel process for preparing 4-{3-[4-(2-methyl-imidazol-1-yl)-phenyl sulfanyl]-phenyl}-tetrahydro-pyran-4-carboxylic acid amide methyl sulfonate. However, said disclosed process is not the same as that of the present invention.

Reference is further made to copending applications filed of even date with the instant application, Attorney Docket Nos. PC10530 and PC10682, which also involve processes of making 5-lipoxygenase inhibitors having varied heterocyclic ring systems and which have some process elements in common with the process of the instant application.

BACKGROUND OF THE INVENTION

There is disclosed in WO 96/11911 a class of novel compounds active as inhibitors of the activity of the 5-lipoxygenase enzyme, characterized by the following structural Formula (1.1.0):

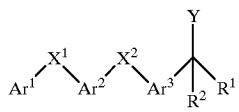

(1.1.0)

wherein:

$Ar^1$ is a heterocyclic moiety selected from the group consisting of imidazolyl; pyrrolyl; pyrazolyl; 1,2,3-triazolyl; 1,2,4-triazolyl; indolyl; indazolyl; and benzimidazolyl; bonded to $X^1$ through a ring nitrogen atom; and substituted with 0–2 substituents selected from the group consisting of halo; hydroxy; cyano; amino; $(C_1-C_4)$alkyl; $(C_1-C_4)$alkoxy; $(C_1-C_4)$alkylthio; $(C_1-C_4)$halo-substituted alkyl; $(C_1-C_4)$halo-substituted alkoxy; $(C_1-C_4)$alkylamino; and di$(C_1-C_4)$alkylamino;

$X^1$ is a direct bond or $(C_1-C_4)$alkylene;

$Ar^2$ is phenylene substituted with 0–2 substituents selected from the group consisting of halo; hydroxy; cyano; amino; $(C_{1-C4})$alkyl; $(C_1-C_4)$alkoxy; $(C_1-C_4)$alkylthio; $(C_1-C_4)$halo-substituted alkyl; and $(C_1-C_4)$halo-substituted alkoxy;

$X^2$ is —A-X— or —X-A— wherein A is a direct bond or $(C_1-C_4)$alkylene and X is oxy; thio; sulfinyl; or sulfonyl;

$Ar^3$ is a member selected from the group consisting of phenylene; pyridylene; thienylene; furylene; oxazolylene; and thiazolylene; substituted with 0–2 substituents selected from halo; hydroxy; cyano; amino; $(C_1-C_4)$alkyl; $(C_1-C_4)$alkoxy; $(C_1-C_4)$alkylthio; $(C_1-C_4)$halo-substituted alkyl; $(C_1-C_4)$halo-substituted alkoxy; $(C_1-C_4)$alkylamino; and di$(C_1-C_4)$alkylamino;

$R^1$ and $R^2$ are each $(C_1-C_4)$alkyl; or together they form a group of formula: —$D^1$-Z-$D^2$— which together with the carbon atom to which it is attached defines a ring having 3 to 8 atoms, wherein $D^1$ and $D^2$ are $(C_1-C_4)$alkylene and Z is a direct bond or oxy; thio; sulfinyl; sulfonyl; or vinylene; and $D^1$ and $D^2$ may be substituted by $(C_1-C_3)$alkyl; and Y is $CONR^3R^4$; CN; $C(R^3)$=N-$OR^4$; $COOR^3$; $COR^3$; or $CSNR^3R^4$; wherein $R^3$ and $R^4$ are each H or $(C_1-C_4)$alkyl.

With respect to the above-recited compounds, the preferred meaning for $(C_1-C_4)$halo-substituted alkyl is trifluoromethyl; and the preferred meaning for $(C_1-C_4)$halo-substituted alkoxy is trifluoromethoxy. A preferred group of the above-recited compounds consists of those wherein $Ar^2$ is 1,4-phenylene and $Ar^3$ is 1,3-phenylene or 5-fluoro-1,3-phenylene. Within said preferred group, more preferred compounds are those in which $Ar^1$ is 2-alkylimidazolyl; $X^1$ is a direct bond; and Y is $CONH^2$; and those in which $Ar^1$ is pyrrolyl; $X^1$ is $CH_2$; and Y is $CONH^2$.

A particularly preferred embodiment of the above-described class of inhibitory compounds is the following compound of Formula (1.0.0):

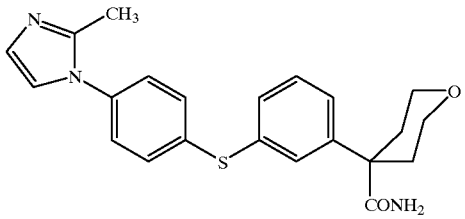

(1.0.0)

Compounds which inhibit the action of lipoxygenase enzyme are useful in the treatment or alleviation of inflammatory diseases, allergy and cardiovascular diseases in mammals including humans. Lipoxygenase enzyme activity occurs as part of the arachidonic acid cascade. Arachidonic acid is the biological precursor of several groups of biologically active endogenous metabolites. Arachidonic acid is first released from membrane phospholipids via the action of phospholipase A2. Arachidonic acid is then metabolized (i) by cyclooxygenase to give prostaglandins including prostacyclin, and thromboxanes; or (ii) by lipoxygenase to give hydroperoxy fatty acids, which may be further converted to leukotrienes.

Leukotrienes, in turn, are extremely potent and elicit a wide variety of biological effects, e.g., peptidoleukotrienes, $LTC_4$, $LTD_4$, and $LTE_4$, are important bronchoconstrictors and vaso-constrictors, and cause plasma extravasation by increasing capillary permeability. $LTB_4$ is a potent chemotactic agent which intensifies leukocyte infiltration and degranulation at a site of inflammation. Leukotrienes have been implicated in a number of human disease states including asthma, chronic obstructive pulmonary disease, allergic rhinitis, rheumatoid arthritis, gout, psoriasis, atopic dermatitis, adult respiratory distress syndrome (ARDS), and inflammatory bowel diseases including. Crohn's disease. An agent which actively inhibits lipoxygenases, and as a consequence the production of leukotrienes, will be of significant therapeutic value in treating acute and chronic inflammatory conditions. See Masamune and Melvin, *Annual Reports in Medicinal Chemistry* 24, 71–80 (1989). Particular lipoxygenase inhibitors have been disclosed in EP 0 462 830; EP 0 505 122; and EP 0 540 165.

Several preparation processes for the lipoxygenase inhibitors described in above-mentioned published application WO 96/39408 are set forth therein. An example of such a preparation process is the coupling of a compound of Formula (1.2.0) and a compound of Formula (1.2.1), which may be represented by the reaction scheme set out below:

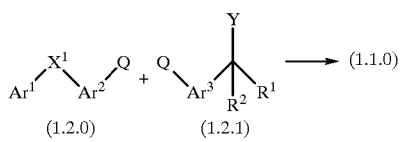

where $Ar^1$ is 2-methyl-imidazol-1-yl; $X^1$ is a direct bond; $Ar^2$ and $Ar^3$ are both phenylene; Y is CN; and $R^1$ and $R^2$ are taken together to form 3,4,5,6-tetrahydro-2H-pyran. $X^2$ is S, resulting in a thioether, and is formed by the reaction of the two Q displaceable groups, in the presence of thiourea and a suitable catalyst, e.g., tetrakis(triphenylphosphine)-palladium, and a reducing agent, e.g., sodium cyanoborohydride. Reference is made to *Chem. Lett.*, 1379–1380 (1986); and U.S. Pat. No. 5,883,106 mentioned further above. Suitable displaceable groups Q are said to include a halo or sulfonyloxy group.

DESCRIPTION OF THE STATE OF THE ART

The present invention is in the field of methods used for synthetic preparation of compounds of the type of Formula (1.0.0), some of which are known compounds, some of which are novel compounds, and some of which are not in the public domain because they cannot be obtained using methods of preparation heretofore known in the art. All of the compounds, however, possess biological activity as inhibitors of 5-lipoxygenase.

In order to facilitate a more ready and complete understanding of the preparation processes of the present invention and their relationship to the state of the art, there follows Sysnthesis Scheme (10.0.0) which depicts the flow of reaction steps in a simplified manner and demonstrates the process parameters by means of specific exemplification.

SYNTHESIS SCHEME (10.0.0)

It will be noted from the synthesis scheme which follows that the first step in the preparation processes of the present invention involves the formation of a thioether by use of an alkylthio-de-halogenation technique analogous to the Williamson Reaction for alkoxy-de-halogenation. This step is catalyzed by a palladium catalyst which is used together with a member from a particular class of bidentate auxiliary ligands, e.g., BINAP.

After this first step, the next two succeeding steps in the preparation processes of the present invention both involve alternate routes. The second step, in which, e.g., the 2-methyl-imidazol-1-yl group is attached by fluorine atom displacement, may be carried out in two ways, identified in the synthesis scheme as (ii-a) and (ii-b). The first involves the use of cesium carbonate, $Cs_2CO_3$ while the second involves the use of solid sodium hydroxide, NaOH, and optionally a catalytic amount of cesium carbonate, $Cs_2CO_3$, or of a phase transfer catalyst such as TBAC.

The third step involves two different approaches to preparing the mesylate salt, which are identified as (iii-a) and (iii-b). The pure final product is then prepared in step (iv).

SYNTHESIS SCHEME (10.0.0)

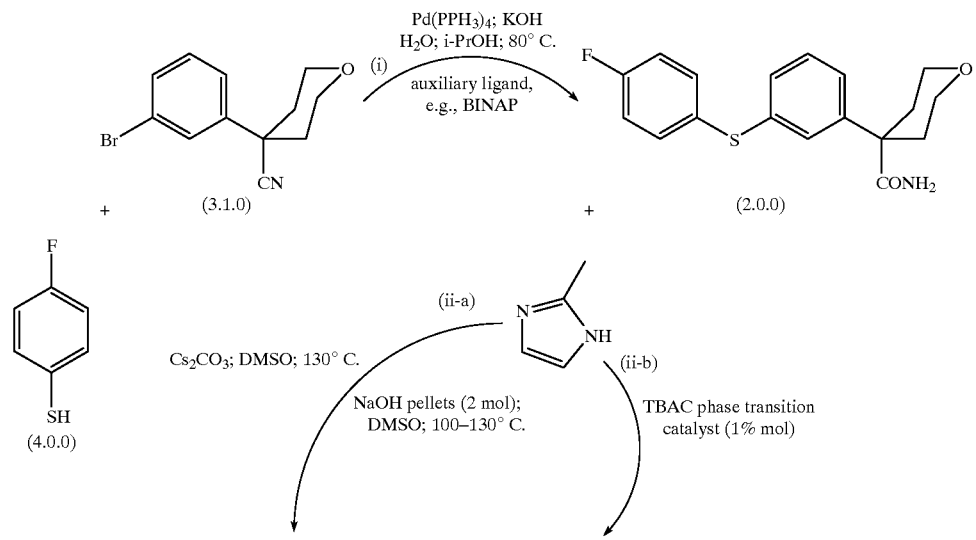

-continued

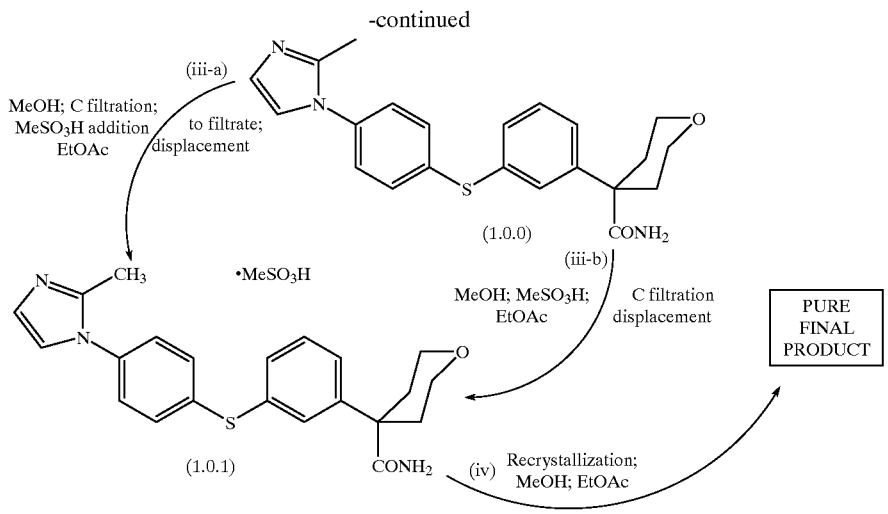

It is known in the art that compounds of the type in Formula (1.0.0) may be prepared by a process which initially uses a palladium catalyzed nucleophilic substitution of aryl halides by thiolate anions or thiols themselves. As in the Williamson reaction, which is the best general method for preparing unsymmetrical as well as symmetrical ethers, yields are improved by phase transfer catalysis. For a detailed treatment of the use of phase transfer catalysis in the preparation of sulfur-containing compounds, see, e.g., Weber; Gokel *Phase Transfer Catalysis in Organic Synthesis*, Springer; New York, 221–233 (1977). Further details concerning the initial stage of the process of the present invention may be found in Migita et al., *Bull. Chem. Soc. Japan* 53, 1385–1389 (1980). Said initial stage may be represented by the following reaction scheme:

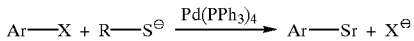

where X is I or Br; and R is phenyl or $(C_1–C_4)$alkyl.

The technical literature contains a number of disclosures relating to palladium-catalyzed synthesis. See, e.g., Brocato et al., *Tetrahedron Lett.* 33, 7433 (1992), which describes ring formation based on the palladium-, especially $Pd(PPh_3)_4$,-catalyzed reaction of bifunctional aromatic compounds with terminal alkynes and carbon monoxide, requiring both palladium(0) and palladium(II) catalysts.

Arcadi et al, *Tetrahedron Lett.* 34, 2813 (1993) discloses synthesis of 2,3,5-trisubstituted furans from aryl halides and 2-propargyl-1,3-dicarbonyl compounds in the presence of tetrakis(triphenylphosphine)palladium(0) and $K_2CO_3$. The authors observe that the nature of the base strongly affects the reaction course.

McClure and Danishefsky, *J. Am. Chem. Soc.* 115, 6094–6100 (1993) discloses synthesis of 1,5-epoxybenzazocine congeners in 90% yield using catalytic tetrakis(triphenylphosphine)-palladium(0) in acetonitrile containing triethylamine.

Nuss et al., *J. Am. Chem. Soc.* 115, 6991–6992 (1993) discloses synthesis of neocarzinostatin chromophore analogs using catalytic tetrakis(triphenylphosphine)palladium (0) in THF and alkynyl stannane reactants.

Paquette and Astles, *J. Org. Chem.* 58, 165–169 (1993) discloses synthesis of furanocembranolides with side chain extension mediated by palladium(0) catalyzed coupling to vinylstannane performed in refluxing benzene or dimethoxyethane. The authors note that the reaction is solvent-dependent, with a change to chloroform being particularly beneficial.

The use of ligands with palladium catalysts is also described in the technical literature, e.g., by Bäckvall, "Metal-Mediated Additions to Conjugated Dienes", *Advances in Metal-Organic Chemistry*, 1, 135–175 (1989), which discloses that the use of menthyl- and neomenthyl-diphenylphosphine complexes resulted in a low symmetric induction in the palladium-catalyzed hydrosilylation of cyclopentadiene and cyclohexadiene.

The technical literature also contains a number of disclosures relating to the use of other transition metals in addition to palladium to catalyze reactions. See, e.g., Takagi, *Chemistry Letters*, 2221–2224 (1987), which discloses the use of nickel(0) and palladium(0) complexes as catalysts in the synthesis of diaryl sulfides from aryl halides and aromatic thiols.

An especially important aspect of the preparation processes of the present invention is the use of a particular class of auxiliary ligand in conjunction with the palladium transition metal catalyst which is being employed in Step (i). An example of such an auxiliary ligand is BINAP. Such organic ligands direct the steric course of the reaction which is being catalyzed by the catalyst with which such organic ligand is associated. Such enantioselective catalysis can achieve very high ee (enantiomeric excess) values, e.g., >98% in the case of 2,2'-bis(diphenylphosphino)-1,1'-binaphthyl-ruthenium acetate [BINAP-Ru(OAc)$_2$] used in the asymmetric reduction of β-keto esters. See Noyori et al., *J. Am. Chem. Soc.* 109, 5856 (1987).

Asymmetric hydrogenations and other organic reactions have been carried out using BINAP-derived catalysts. See, e.g., U.S. Pat. Nos. 4,691,037; 4,739,084; 4,739,085; 4,764,629; 4,994,607; and 4,766,277. Published patent applications and references from the technical literature reporting enantioselective reactions using the BINAP ligand include, e.g., Wu, et al., *Tetrahedron Letters* 34(37), 5927–5930 (1993); Wu, et al., *Tetrahedron Letters* 33, 6331–6334 (1992); Tani, et al., *J. Chem. Soc. Chem. Commun.* 600 (1982); Tani, et al., *Angew Chem. Int. Ed. Engl.* 24(3), 217–219 (1985); Naruta, et al., *Tetrahedron Letters* 28, 4553–4556 (1987); Hodgson, et al., *J. Organomet. Chem.* 325, 627–630 (1987); Hayashi et al., *J. Am. Chem. Soc.* 110, 5579–5581 (1988); Hayashi et al., *J. Am. Chem. Soc.* 111, 3426–3428 (1989); Kollar, et al., *J. Molecular Catalysis* 67, 191–198 (1991); Collman, et al., *J. Chem. Soc. Chem. Commun.* 428 (1993); Murakami, et al. *Bull. Chem. Soc. Jpn.* 65, 3094–3102 (1992); Yamaguchi, et al. *Tetrahedron Asymmetry* 2(7), 663–666 (1991); Burgess, et al., *Tetrahedron Asymmetry* 2(7), 613–621 (1991); Ozawa, et al., *Tetrahedron Letters* 34(15), 2505–2508 (1993); Ozawa, et al., *Tetrahedron Letters* 33(11), 1485–1488 (1992); Ozawa, et al., *Chemistry Letters* 2177–2180 (1992); Kagechika, et al., *J. Org. Chem.* 56, 4093–4094 (1991); Sakamoto, et al.,. *Tetrahedron Letters* 33, 6845–6848 (1992); Brunner, et al., *J. Organometallic Chem.* 456, 71–75 (1993); Trost et al., *J. Amer. Chem. Soc.* 102, 7932–7934 (1980); Miyashita, et al., *Tetrahedron* 40(8), 1245–1253; Waldman, et al., "Selectivity in Catalysis," M. E. Davis and S. L. Snib, Eds., ACS Symposium Series 517 (1993); Ozawa, et al., "Selectivity in Catalysis," M. E. Davis and S. L. Snib, Eds., ACS Symposium Series 517 (1993); Chan, et al., "Selectivity in Catalysis," M. E. Davis and S. L. Snib, Eds., ACS Symposium Series 517 (1993); Durina, et al., "Homogeneous Catalysis By the Optically Active Complexes of Transition Metals and Its Application In the Synthesis of Bioactive Molecules," *J. Org. Chem. USSR* 28, 1547–1600 and 1913–1971; WO 90/15790; and WO 92/09552.

New ligand compositions for use with transition metal complexes have been developed which may represent suitable replacements for BINAP and related ligands. For example, new families of amine oxazolinyl ligands for practical asymmetric synthesis are disclosed in WO 99/24410, and include ligands such as those of Formula (1.0.10):

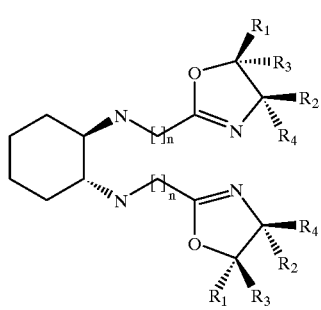

(1.0.10)

None of the above-described references, however, discloses or suggests the particular processes of preparation of the present invention, which are both facile and efficient, while at the same time affording acceptable yields not achievable heretofore.

SUMMARY OF THE INVENTION

The present invention is concerned with processes of preparation where a number of the ultimate products of said processes are known compounds of demonstrated utility as 5-lipoxygenase inhibitors. The present invention additionally concerns a number of other ultimate final products of said processes which have not been known heretofore because they were synthetically inaccessible prior to the availability of said processes of the present invention. These novel final products are also useful as 5-lipoxygenase inhibitors, as described in detail further herein. All of said processes of preparation of the present invention are recited in summary in the paragraphs immediately below.

A key intermediate used in the processes of preparation of the present invention is tetrahydro-4-[3-(4-fluorophenyl) thio]phenyl-2H-pyran-4-carboxamide of Formula (2.0.0):

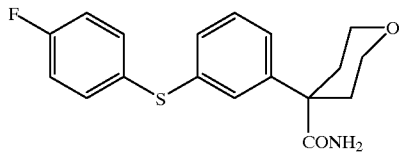

(2.0.0)

The present invention is thus also concerned with a process for preparing a compound of Formula (2.0.0), which may be illustrated by the following SYNTHESIS SCHEME (10.0.1)

SYNTHESIS SCHEME (10.0.1)

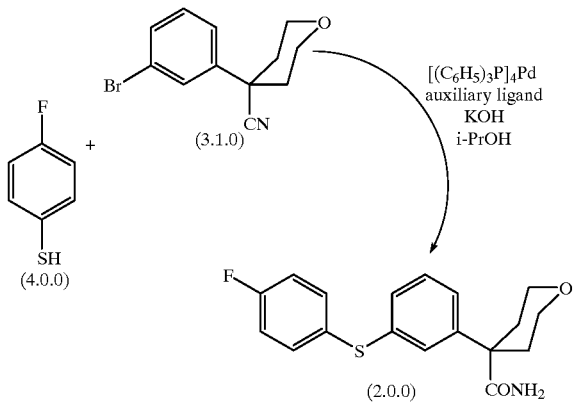

comprising:
(a) establishing a reaction mixture consisting of
(1) tetrahydro-4-(3-bromo- or iodo-phenyl)-2H-pyran-4-nitrile of Formula (3.0.0):

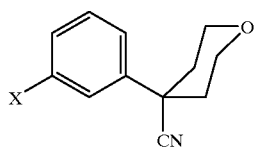

(3.0.0)

where X is bromo or iodo;
and
(2) 4-fluorothiophenol of Formula (4.0.0):

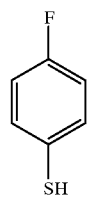

(4.0.0)

(3) in a solvent consisting of a straight or branched chain aliphatic alcohol having a total of from 2 to 7 carbon atoms, optionally as an aqueous mixture thereof; and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;

(4) in the presence of strong base of Formula (5.0.0):

$$M\text{-}O\text{-}R^5 \tag{5.0.0}$$

where

M is an alkali metal, Group 1/Ia element, selected from the group consisting of lithium, Li; sodium, Na; potassium, K; rubidium, Rb; and cesium, Cs; and $R^5$ is hydrogen, H; or straight or branched chain ($C_1$–$C_4$) alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$; including mixtures of the above; and further (5) in the presence of a transition metal catalyst comprising a palladium metal complex which preferably is a member selected from the group consisting of tetrakis(triphenylphosphine)palladium(0), $[(C_6H_5)_3P]_4Pd(0)$;

tetrakis(methyldiphenylphosphine)palladium(0), $[(C_6H_5)_2PCH_3]_4Pd(0)$;

trans-dichlorobis(methyldiphenylphosphine)palladium(II), $[(C_6H_5)_2PCH_3]_2PdCl_2$;

dichlorobis[methylenebis(diphenylphosphine)]dipalladium-dichloromethane adduct;

dichlorobis(triphenylphosphine)palladium(II), $[(C_6H_5)_3P]_2PdCl_2$;

tris(dibenzylideneacetone)dipalladium(0)-chloroform adduct, $(C_6H_5CH=CHCOCH=CHC_6H_5)_3Pd_2 \cdot CHCl_3$;

bis(dibenzylideneacetone)palladium(0), $(C_6H_5CH=CHCOCH=CHC_6H_5)_2Pd$;

[1,1'-bis(diphenylphosphino)ferrocene]dichloropalladium (II), complex with dichloromethane bis[1,2-bis(diphenylphosphino)ethane]palladium(0); and (π-allyl)palladium(II) chloride dimer;

and still further (6) in the presence of an auxiliary ligand for said transition metal catalyst comprising a palladium metal complex, wherein said ligand is a bidentate, chiral, axially dissymmetric aromatic compound of Formula (5.5.0) or (5.5.1):

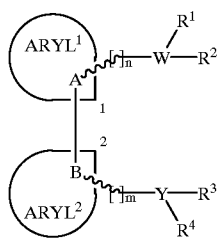

(5.5.0)

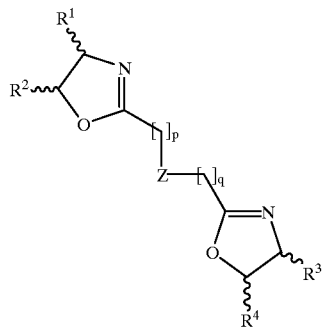

(5.5.1)

where in Formula (5.5.0): W and Y are both phosphorus or are both nitrogen, or taken together with $R^1$, $R^2$, $R^3$, and $R^4$ are hydrogen phosphate; m and n are independently 1 or 2; $R^1$, $R^2$, $R^3$, and $R^4$ are independently selected from the group consisting of hydrogen; ($C_1$–$C_4$)alkyl; phenyl; naphthyl; biphenyl; tolyl; furyl; pyrrolyl; and pyridyl; $ARYL^1$ and $ARYL^2$ are independently selected from the group consisting of phenyl; biphenyl; 1- or 2-naphthyl; pyridyl; and quinolinyl; or $ARYL^1$ and $ARYL^2$ are taken together to form a phenyl; naphthyl; biphenyl; pyridyl; quinolinyl; or cyclohexyl group; A and B are both carbon atoms which are either bonded directly to carbon atoms identified as 1 and 2, or else are adjacent constituent carbon atoms identified as 1 and 2 of $ARYL^1$ and $ARYL^2$, respectively, in which case the bonds attached to A and B of unspecified orientation are attached to carbon atoms α to carbon atoms identified as 1 and 2; and said bonds of unspecified orientation must have opposite orientations, whereby said auxiliary ligand is axially dissymmetric; and in Formula (5.5.1): p and q are independently 0, 1 or 2; $R^1$, $R^2$, $R^3$, and $R^4$ have the same meaning as above selected on an independent basis; Z is —N($R^5$)— or —($CH_2$)— where $R^5$ is hydrogen or ($C_1$–$C_4$)alkyl; provided that p and q cannot be 0 when Z is —N($R^5$)—; and for the bonds of unspecified orientation attached to $R^1$, $R^2$, $R^3$, and $R^4$, said bonds of $R^1$ and $R^2$ must have an orientation opposite to that of said bonds of $R^3$ and $R^4$, whereby said auxiliary ligand is axially dissymmetric;

preferably, said auxiliary ligand is (S)-(—)-2,2'-bis (diphenylphosphino)-1,1'-binaphthyl (S-BINAP);

followed by (b) heating said reaction mixture, preferably at reflux, preferably for a period of from 12 to 36 hours, more preferably from 18 to 24 hours; whereby there is produced said compound of Formula (2.0.0) which is optionally isolated using conventional separation techniques.

The above-described process of preparation in which the 4-carboxamide portion of the pyran moiety is formed during the thio-addition step is a preferred manner of carrying out this portion of the process of the present invention. A useful alternative embodiment comprises formation of the 4-carboxamide portion of the pyran moiety before the step of thio-addition is carried out. Said alternative embodiment of this portion of the process of the present invention involves a process for preparing a compound of Formula (2.0.0) which may be illustrated by the following SYNTHESIS SCHEME (10.1.0):

SYNTHESIS SCHEME (10.1.0)

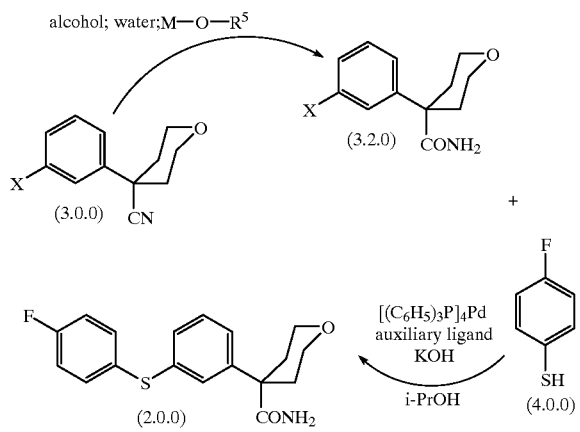

comprising:
(a) establishing a reaction mixture consisting of
(1) tetrahydro-4-(3-bromo- or iodo-phenyl)-2H-pyran-4-nitrile of Formula (3.0.0):

(3.0.0)

where X is bromo or iodo;
(2) in a solvent consisting of an alcohol as defined above, optionally as an aqueous mixture thereof; preferably a secondary alcohol as defined above; more preferably iso-propyl alcohol; optionally as an aqueous mixture of said secondary alcohol;
(3) in the presence of strong base of Formula (5.0.0):

$M-O-R^5$ (5.0.0)

where M and $R^5$ are as defined above; preferably wherein said strong base is sodium hydroxide, NaOH; potassium hydroxide, KOH; sodium ethoxide, $NaOCH_2CH_3$; or potassium tert-butoxide, $KOC(CH_3)_3$;
followed by
(b) heating said reaction mixture, preferably at reflux, preferably for a period of from 3 to 8 hours, more preferably from 5 to 6 hours; whereby there is produced a compound of Formula (3.2.0):

(3.2.0)

where X is bromo or iodo;
followed by (c) forming a reaction mixture consisting of said compound of Formula (3.2.0) and 4-fluorothiophenol of Formula (4.0.0):

(4.0.0)

(1) in a solvent consisting of an alcohol as defined above, optionally as an aqueous mixture thereof; preferably a secondary alcohol as defined above; more preferably iso-propyl alcohol; optionally as an aqueous mixture of said secondary alcohol;
(2) in the presence of a strong base of Formula (5.0.0):

$M-O-R^5$ (5.0.0)

where M and $R^5$ are as defined above; preferably wherein said strong base is sodium hydroxide, NaOH; potassium hydroxide, KOH; sodium ethoxide, $NaOCH_2CH_3$; or potassium tert-butoxide, $KOC(CH_3)_3$;
and further
(3) in the presence of a transition metal catalyst comprising a palladium metal complex, which is preferably a member selected from the group consisting of
tetrakis(triphenylphosphine)palladium(0), $[(C_6H_5)_3P]_4Pd(0)$;
tetrakis(methyldiphenylphosphine)palladium(0), $[(C_6H_5)_2PCH_3]_4Pd(0)$;
trans-dichlorobis(methyldiphenylphosphine)palladium(II), $[(C_6H_5)_2PCH_3]_2PdCl_2$;
dichlorobis[methylenebis(diphenylphosphine)]dipalladium-dichloromethane adduct;
dichlorobis(triphenylphosphine)palladium(II), $[(C_6H_5)_3P]_2PdCl_2$;
tris(dibenzylideneacetone)dipalladium(0)-chloroform adduct, $(C_6H_5CH=CHCOCH=CHC_6H_5)_3Pd_2 \cdot CHCl_3$;
bis(dibenzylideneacetone)palladium(0), $(C_6H_5CH=CHCOCH=CHC_6H_5)_2Pd$;
[1,1'-bis(diphenylphosphino)ferrocene]dichloropalladium (II), complex with dichloromethane
bis[1,2-bis(diphenylphosphino)ethane]palladium(0); and (π-allyl)palladium(II) chloride dimer;
and still further
(4) in the presence of an auxiliary ligand for said transition metal catalyst comprising a palladium metal complex, wherein said ligand is a bidentate, chiral, axially dissymmetric aromatic compound of Formula (5.5.0) or (5.5.1):

(5.5.0)

-continued

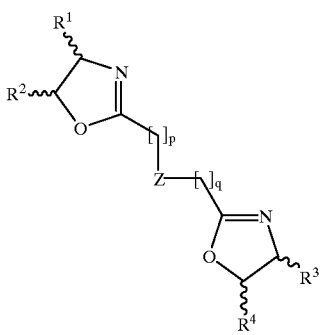

(5.5.1)

where in Formula (5.5.0): W and Y are both phosphorus or are both nitrogen; m and n are independently 1 or 2; $R^1$, $R^2$, $R^3$, and $R^4$ are independently selected from the group consisting of hydrogen; $(C_1-C_4)$alkyl; phenyl; naphthyl; biphenyl; tolyl; furyl; pyrrolyl; and pyridyl; $ARYL^1$ and $ARYL^2$ are independently selected from the group consisting of phenyl; biphenyl; 1- or 2-naphthyl; pyridyl; and quinolinyl; or $ARYL^1$ and $ARYL^2$ are taken together to form a phenyl; naphthyl; biphenyl; pyridyl; quinolinyl; or cyclohexyl group; A and B are both carbon atoms which are either bonded directly to carbon atoms identified as 1 and 2, or else are adjacent constituent carbon atoms identified as 1 and 2 of $ARYL^1$ and $ARYL^2$, respectively, in which case the bonds attached to A and B of unspecified orientation are attached to carbon atoms α to carbon atoms identified as 1 and 2; and said bonds of unspecified orientation must have opposite orientations, whereby said auxiliary ligand is axially dissymmetric; and in Formula (5.5.1): p and q are independently 0, 1 or 2; $R^1$, $R^2$, $R^3$, and $R^4$ have the same meaning as above selected on an independent basis; Z is —$N(R^5)$— or —$(CH_2)$— where $R^5$ is hydrogen or $(C_1-C_4)$alkyl; provided that p and q cannot be 0 when Z is —$N(R^5)$—; and for the bonds of unspecified orientation attached to $R^1$, $R^2$, $R^3$, and $R^4$, said bonds of $R^1$ and $R^2$ must have an orientation opposite to that of said bonds of $R^3$ and $R^4$, whereby said auxiliary ligand is axially dissymmetric;

preferably, said auxiliary ligand is (S-(—)-2,2'-bis (diphenylphosphino)-1,1'-binaphthyl (S-BINAP);

followed by (d) heating said reaction mixture, preferably at reflux, preferably for a period of from 5 to 15 hours, more preferably from 8 to 10 hours; whereby there is produced said compound of Formula (2.0.0).

Preparation of the key intermediate of Formula (2.0.0) as described in detail above, permits the next steps of the preparation processes of the present invention to be carried out, in accordance with which the desired end product of Formula (1.0.0), and the genus in which it is contained of Formula (is produced at high purity levels and in high yield. The above-mentioned next steps are described in detail in the paragraphs which follow.

The present invention is still further concerned with a process for preparing a compound of Formula (1.3.0):

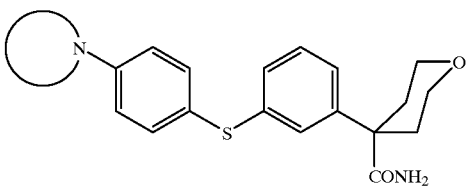

(1.3.0)

which may be illustrated by the following SYNTHESIS SCHEME (10.2.0):

SYNTHESIS SCHEME (10.2.0)

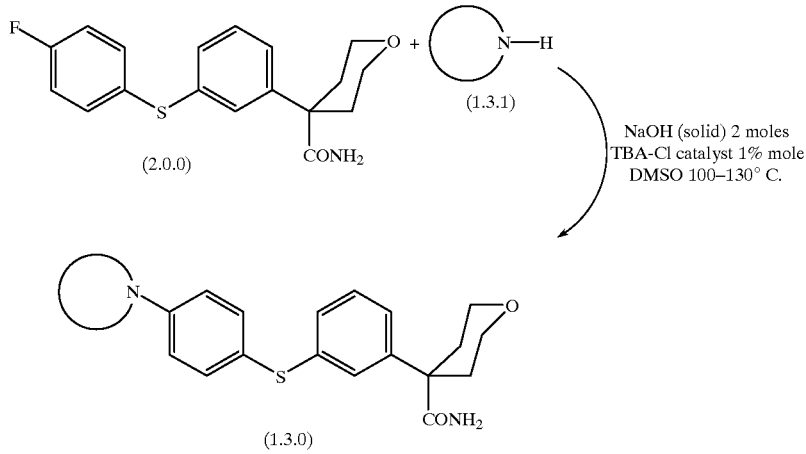

where
the moiety of following Formula (1.3.1):

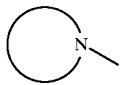
(1.3.1)

is an electron deficient monocyclic or benzo-fused bicyclic N-heterocyclic group containing two nitrogen atoms, of Formula (1.3.2) (1.3.3), (1.3.4) or (1.3.5):

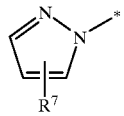
(1.3.2)

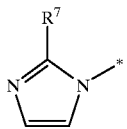
(1.3.3)

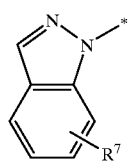
(1.3.4)

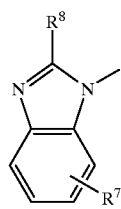
(1.3.5)

where
"*" is a symbol which represents the point of attachment of the moiety of Formula (1.3.2) (1.3.3, (1.3.4) or (1.3.5);
$R^7$ and $R^8$ are independently selected from the group consisting of H; straight or branched chain $(C_1-C_4)$alkyl; and $(C_6-C_{10})$aryl; wherein said alkyl and aryl groups are substituted by 0 to 2 substituents selected from the group consisting of halo; hydroxy; cyano; amino; $(C_1-C_4)$alkyl; $(C_1-C_4)$alkoxy; $(C_1-C_4)$alkylthio; $(C_1-C_4)$halo-substituted alkyl; $(C_1-C_4)$halo-substituted alkoxy; $(C_1-C_4)$alkylamino; and di$(C_1-C_4)$alkylamino;
comprising:
(a) establishing a reaction mixture consisting of
(1) tetrahydro-4-[3-(4-fluorophenyl)thio]phenyl-2H-pyran-4-carboxamide of Formula (2.0.0)

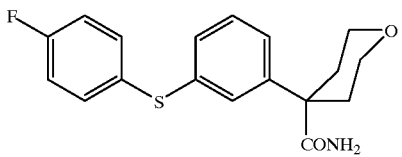
(2.0.0)

and
(2) an electron deficient monocyclic or benzo-fused bicyclic N-heterocycle containing two nitrogen atoms, of Formula (1.3.6) (1.3.7), (1.3.8) or (1.3.9):

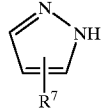
(1.3.6)

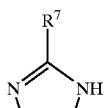
(1.3.7)

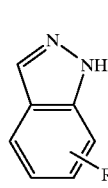
(1.3.8)

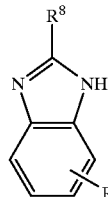
(1.3.9)

where $R^7$ and $R^8$ have the same meaning as set out above;
(3) in an aprotic solvent, preferably dimethylsulfoxide (DMSO);
(4) in the presence of a strong base in solid form selected from the group consisting of sodium hydroxide, NaOH; and potassium hydroxide, KOH;
and optionally
(5) in the presence of a catalytic amount of cesium carbonate, $Cs_2CO_3$, or of a phase transfer catalyst, preferably a member selected from the group consisting of cetyltrimethylammonium bromide (CTMAB); dibenzo-18-crown-6 (DB-18-c-6); dicyclohexano-18-crown-6 (DC-18-c-6); 18-crown6 (18-c-6); (—)-N-dodecyl-N-methylephedrinium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide (TBAI); tetra-ethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC); and more preferably a quaternary ammonium salt or a phosphonium salt comprising a member of the above-recited group;
followed by
(b) heating said reaction mixture, preferably at reflux, under a nitrogen atmosphere; whereby there is produced a compound of Formula (1.3.0).

An alternative process to the one described immediately above for preparing a compound of Formula (1.3.0) may also be used with acceptable results. Said alternative process may be illustrated by the following SYNTHESIS SCHEME (10.2.1):

SYNTHESIS SCHEME (10.2.1)

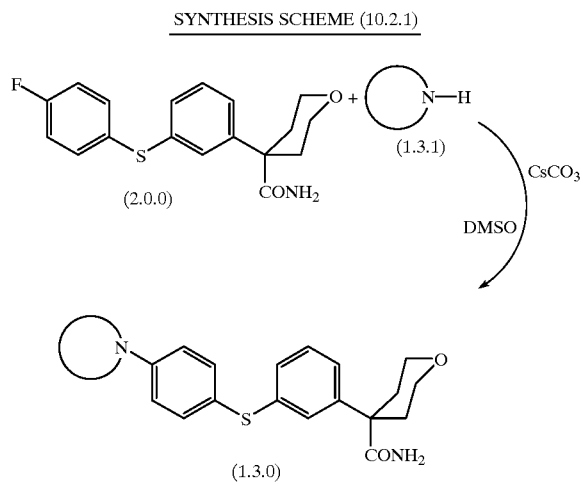

where the moiety of following Formula (1.3.1):

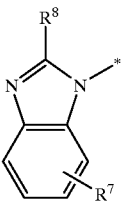
(1.3.1)

is an electron deficient monocyclic or benzo-fused bicyclic N-heterocyclic group containing two nitrogen atoms, of Formula (1.3.2) (1.3.3), (1.3.4) or (1.3.5):

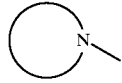
(1.3.2)

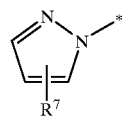
(1.3.3)

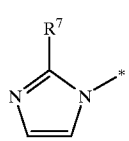
(1.3.4)

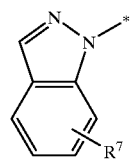
(1.3.5)

where

"*" is a symbol which represents the point of attachment of the moiety of Formula (1.3.2) (1.3.3), (1.3.4) or (1.3.5);

$R^7$ and $R^8$ are independently selected from the group consisting of H; straight or branched chain $(C_1-C_4)$alkyl; and $(C_6-C_{10})$aryl; wherein said alkyl and aryl groups are substituted by 0 to 2 substituents selected from the group consisting of halo; hydroxy; cyano; amino; $(C_1-C_4)$alkyl; $(C_1-C_4)$alkoxy; $(C_1-C_4)$alkylthio; $(C_1-C_4)$halo-substituted alkyl; $(C_1-C_4)$halo-substituted alkoxy; $(C_1-C_4)$alkylamino; and di$(C_1-C_4)$alkylamino;

comprising:

(a) establishing a reaction mixture consisting of (1) tetrahydro-4-[3-(4-fluorophenyl)thio]phenyl-2H-pyran-4-carboxamide of Formula (2.0.0):

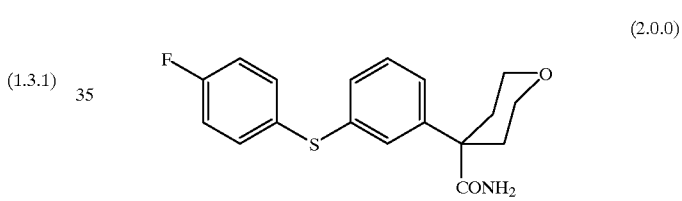
(2.0.0)

and (2) an electron deficient monocyclic or benzo-fused bicyclic N-heterocycle containing two nitrogen atoms, of Formula (1.3.6) (1.3.7), (1.3.8) or (1.3.9):

(1.3.6)

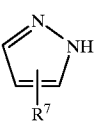
(1.3.7)

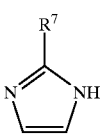
(1.3.8)

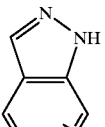

(1.3.9)

[Structure: benzimidazole with R⁸ at 2-position and R⁷ on benzo ring]

where R⁷ and R⁸ have the same meaning as set out above;

(3) in an aprotic solvent, preferably dimethylsulfoxide (DMSO);

(4) in the presence of a carbonate of Formula (5.1.0):

$$(M)_2\text{-}CO_3 \tag{5.1.0}$$

where M has the same meaning as defined further above, which is preferably cesium carbonate, $Cs_2CO_3$;

followed by (b) heating said reaction mixture, preferably at reflux, under a nitrogen atmosphere; whereby there is produced a compound of Formula (1.3.0).

The present invention is further concerned with the above-recited method of preparing a compound of Formula (1.3.0), wherein said compound of Formula (1.3.0) is a member selected from the group consisting of:

Tetrahydro-4-{3-[4-(2-methyl-1H-imidazol-1-yl)phenyl]thio}phenyl-2H-pyran-4-carboxamide;

Tetrahydro-4-{3-[4-(1H-imidazol-1-yl)phenyl]thio}phenyl-2H-pyran-4-carboxamide;

Tetrahydro-4-{3-[4-(1H-benzoimidazol-1-yl)phenyl]thio}phenyl-2H-pyran-4-carboxamide;

Tetrahydro-4-{3-[4-(1H-pyrazol-1-yl)phenyl]thio}phenyl-2H-pyran-4-carboxamide; and Tetrahydro-4-{3-[4-(4-methyl-1H-pyrazol-1-yl)phenyl]thio}phenyl-2H-pyran-4-carboxamide.

The above-mentioned final products have not been known heretofore because they have been synthetically inaccessible prior to the availability of the processes of the present invention. These novel final products are also useful as 5-lipoxygenase inhibitors, and consist of a member selected from the group consisting of:

Tetrahydro-4-{3-[4-(1H-imidazol-1-yl)phenyl]thio}phenyl-2H-pyran-4-carboxamide;

Tetrahydro-4-{3-[4-(1H-benzoimidazol-1-yl)phenyl]thio}phenyl-2H-pyran-4-carboxamide;

Tetrahydro-4-{3-[4-(1H-pyrazol-1-yl)phenyl]thio}phenyl-2H-pyran-4-carboxamide; and Tetrahydro-4-{3-[4-(4-methyl-1H-pyrazol-1-yl)phenyl]thio}phenyl-2H-pyran-4-carboxamide.

The present invention is still further concerned with a process for preparing a compound of Formula (1.0.0):

(1.0.0)

[Structure of Formula (1.0.0): 2-methylimidazole-substituted phenyl linked via S to phenyl bearing tetrahydropyran-4-carboxamide]

comprising:

(a) establishing a reaction mixture consisting of (1) tetrahydro-4-[3-(4-fluorophenyl)thio]phenyl-2H-pyran-4-carboxamide of Formula (2.0.0):

(2.0.0)

[Structure of Formula (2.0.0): 4-fluorophenyl linked via S to phenyl bearing tetrahydropyran-4-carboxamide]

and (2) 2-methylimidazole;

(3) in an aprotic solvent, preferably dimethylsulfoxide (DMSO);

(4) in the presence of a strong base in solid form selected from the group consisting of sodium hydroxide, NaOH; and potassium hydroxide, KOH;

and optionally (5) in the presence of a catalytic amount of cesium carbonate, $Cs_2CO_3$, or of a phase transfer catalyst, preferably a member selected from the group consisting of cetyltrimethylammonium bromide (CTMAB); dibenzo-18-crown-6 (DB-18-c-6); dicyclohexano-18-crown-6 (DC-18-c-6); 18-crown-6 (18-c-6); (—)-N-dodecyl-N-methylephedrinium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide TBAI); tetra-ethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC); and more preferably a quaternary ammonium salt or a phosphonium salt comprising a member of the above-recited group;

followed by (b) heating said reaction mixture, preferably at reflux, preferably from 115° to 145° C., more preferably from 125° to 130° C., under a nitrogen atmosphere, preferably for from 12 to 30 hours, more preferably for from 17 to 24 hours; whereby there is produced said compound of Formula (1.3.0).

The present invention is still further concerned with a process for preparing a substantially pure mesylate salt of Formula (1.0.1):

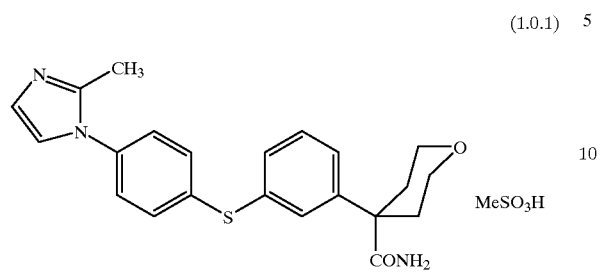
(1.0.1)

which may be illustrated by the following SYNTHESIS SCHEME (10.3.0):

comprising:

(a) preparing a compound of Formula (2.0.0):

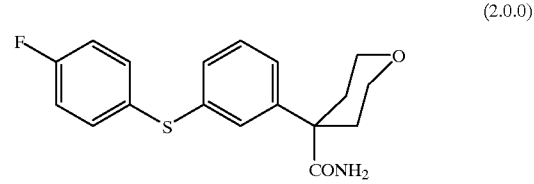
(2.0.0)

comprising:

(1) establishing a reaction mixture consisting of
   (i) tetrahydro-4-(3-bromo-phenyl)-2H-pyran-4-nitrile of Formula (3.1.0):

SYNTHESIS SCHEME (10.3.0)

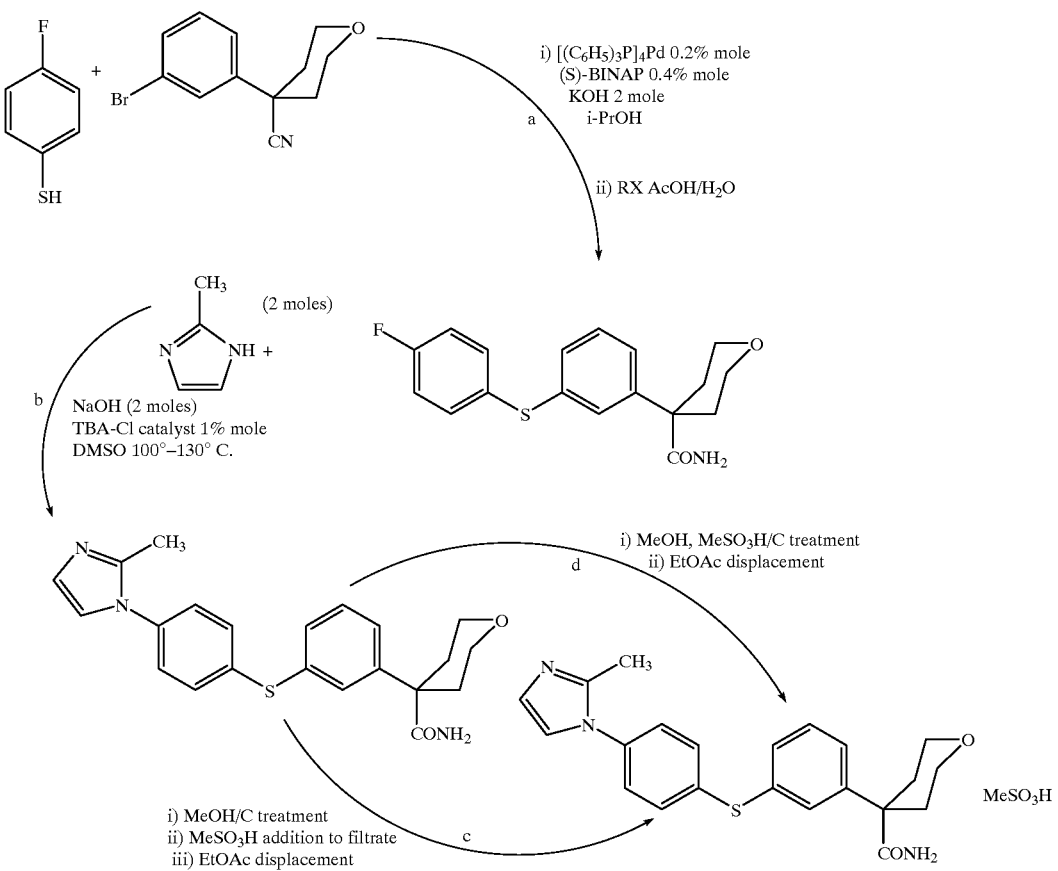

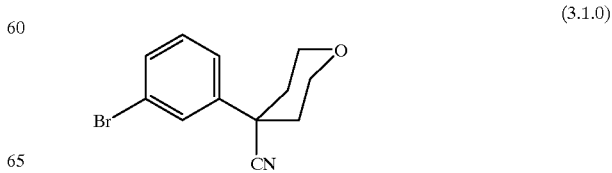
(3.1.0)

and (ii) 4-fluorothiophenol of Formula (4.0.0):

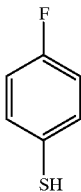
(4.0.0)

(iii) in a solvent selected from the group consisting of iso-propyl alcohol, sec-butyl alcohol, iso-pentyl alcohol, and 2-heptanol, preferably iso-propyl alcohol, optionally as an aqueous mixture thereof;

(iv) in the presence of a strong base selected from the group consisting of sodium hydroxide, NaOH; and potassium hydroxide, KOH;

and further (v) in the presence of a transition metal catalyst comprising a member independently selected from the group consisting of palladium metal complexes; preferably wherein said palladium metal complex is a member selected from the group consisting of tetrakis(triphenylphosphine)palladium(0), $[(C_6H_5)_3P]_4Pd(0)$;

tetrakis(methyldiphenylphosphine)palladium(0), $[(C_6H_5)_2PCH_3]_4Pd(0)$;

trans-dichlorobis(methyldiphenylphosphine)palladium(II), $[(C_6H_5)_2PCH_3]_2PdCl_2$;

dichlorobis[methylenebis(diphenylphosphine)]dipalladium-dichloromethane adduct;

dichlorobis(triphenylphosphine)palladium(II), $[(C_6H_5)_3P]_2PdCl_2$;

tris(dibenzylideneacetone)dipalladium(0)-chloroform adduct, $(C_6H_5CH=CHCOCH=CHC_6H_5)_3Pd_2·CHCl_3$;

bis(dibenzylideneacetone)palladium(0), $(C_6H_5CH=CHCOCH=CHC_6H_5)_2Pd$;

[1,1'-bis(diphenylphosphino)ferrocene]dichloropalladium (II), complex with dichloromethane bis[1,2-bis(diphenylphosphino)ethane]palladium(II); and (π-allyl)palladium(II) chloride dimer;

and still further (vi) in the presence of an auxiliary ligand for said transition metal catalyst comprising a palladium metal complex, wherein said ligand is a bidentate, chiral, axially dissymmetric aromatic compound of Formula (5.5.0) or (5.5.1):

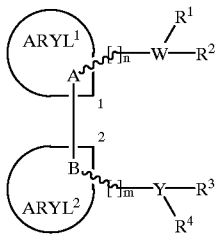
(5.5.0)

-continued

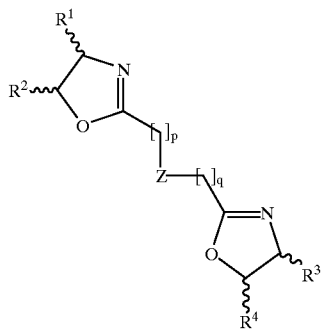
(5.5.1)

where in Formula (5.5.0): W and Y are both phosphorus or are both nitrogen; m and n are independently 1 or 2; $R^1$, $R^2$, $R^3$, and $R^4$ are independently selected from the group consisting of hydrogen; $(C_1–C_4)$alkyl; phenyl; naphthyl; biphenyl; tolyl; furyl; pyrrolyl; and pyridyl; $ARYL^1$ and $ARYL^2$ are independently selected from the group consisting of phenyl; biphenyl; 1- or 2-naphthyl; pyridyl; and quinolinyl; or $ARYL^1$ and $ARYL^2$ are taken together to form a phenyl; naphthyl; biphenyl; pyridyl; quinolinyl; or cyclohexyl group; A and B are both carbon atoms which are either bonded directly to carbon atoms identified as 1 and 2, or else are adjacent constituent carbon atoms identified as 1 and 2 of $ARYL^1$ and $ARYL^2$, respectively, in which case the bonds attached to A and B of unspecified orientation are attached to carbon atoms α to carbon atoms identified as 1 and 2; and said bonds of unspecified orientation must have opposite orientations, whereby said auxiliary ligand is axially dissymmetric; and in Formula (5.5.1): p and q are independently 0, 1 or 2; $R^1$, $R^2$, $R^3$, and $R^4$ have the same meaning as above selected on an independent basis; Z is —N($R^5$)— or —($CH_2$)— where $R^5$ is hydrogen or $(C_1–C_4)$alkyl; provided that p and q cannot be 0 when Z is —N($R^5$)—; and for the bonds of unspecified orientation attached to $R^1$, $R^2$, $R^3$, and $R^4$, said bonds of $R^1$ and $R^2$ must have an orientation opposite to that of said bonds of $R^3$ and $R^4$, whereby said auxiliary ligand is axially dissymmetric;

preferably, said auxiliary ligand is (S)(—)-2,2'-bis(diphenylphosphino)-1,1'-binaphthyl (S-BINAP);

followed by (2) heating said reaction mixture at reflux of from 80° to 84° C. for a period of from 18 to 30 hours, preferably 24 hours; whereby there is produced said compound of Formula (2.0.0);

(b) establishing a reaction mixture consisting of said compound of Formula (2.0.0) and a compound of Formula (1.3.10):

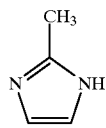
(1.3.10)

(1) in an aprotic solvent which is preferably dimethylsulfoxide (DMSO);

(2) in the presence of a strong base in solid form selected from the group consisting of sodium hydroxide, NaOH; and potassium hydroxide, KOH;

and optionally (3) in the presence of a catalytic amount of cesium carbonate, $Cs_2CO_3$, or of a phase transfer catalyst, preferably a member selected from the group consisting of cetyltrimethylammonium bromide (CTMAB); dibenzo-18-crown-6 (DB-18-c-6); dicyclohexano-18-crown-6 (DC-18-c-6); 18-crown-6 (18-c-6); (—)-N-dodecyl-N-methylephedrinium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide (TBAI); tetra-ethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC); and more preferably a quaternary ammonium salt or a phosphonium salt comprising a member of the above-recited group;

followed by (c) heating said reaction mixture at reflux, under a nitrogen atmosphere; whereby there is produced a compound of Formula (1.0.0):

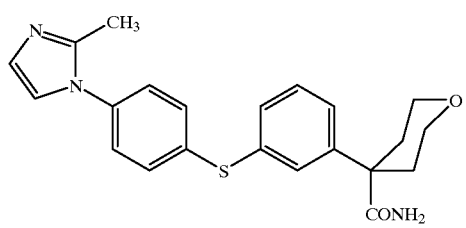

(1.0.0)

followed by (d) forming a concentrated methanol solution of said compound of Formula (1.0.0) which is then filtered, preferably through activated carbon, after which there is then added to the filtrate methanesulfonic acid, $MeSO_3H$; followed by further concentration and the addition of ethyl acetate ad seriatim until a crystalline product is isolated comprising substantially pure mesylate salt of Formula (1.0.1)

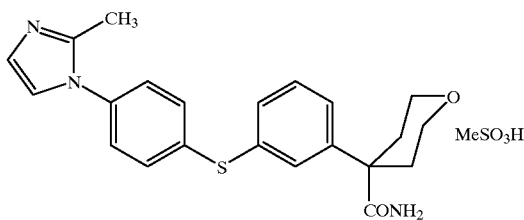

(1.0.1)

or, alternatively, followed by (e) forming a concentrated methanol solution of said compound of Formula (1.0.0) to which there is then added methanesulfonic acid, $MeSO_3H$; followed by filtering of the mixture, preferably through activated carbon, after which there follows further concentration and the addition of ethyl acetate ad seriatim until a crystalline product is isolated comprising substantially pure mesylate salt of Formula (1.0.1)

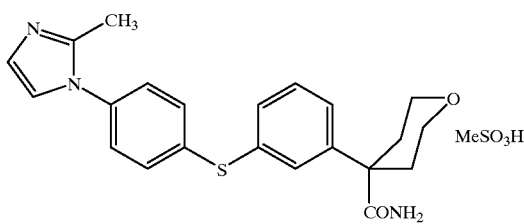

(1.0.1)

DETAILED DESCRIPTION OF THE INVENTION

The present invention involves an improved process for preparing known compounds of demonstrated utility as a 5-lipoxygenase inhibitors, and in particular the compound of Formula (1.0.0):

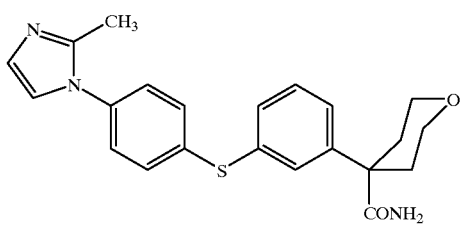

(1.0.0)

Further, the present invention involves preparation of a number of other compounds which have not been known heretofore because they were synthetically inaccessible prior to the availability of the improved process of the present invention. These novel compounds are also useful as 5-lipoxygenase inhibitors, and include, among others, the following compounds of Formulas (1.1.1); (1.1.2); (1.1.3); and (1.1.4):

Tetrahydro-4-{3-[4-(1H-imidazol-1-yl)phenyl]thio}phenyl-2H-pyran-4-carboxamide:

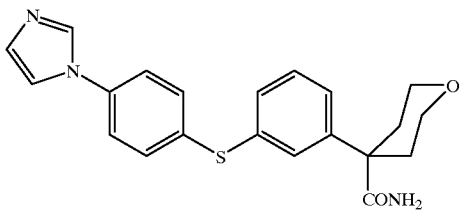
(1.1.1)

Tetrahydro-4-{3-[4-(1H-benzoimidazol-1-yl)phenyl]thio}phenyl-2H-pyran-4-carboxamide:

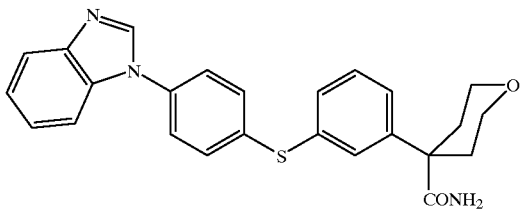
(1.1.2)

Tetrahydro-4-{3-[4-(1H-pyrazol-1-yl)phenyl]thio}phenyl-2H-pyran-4-carboxamide:

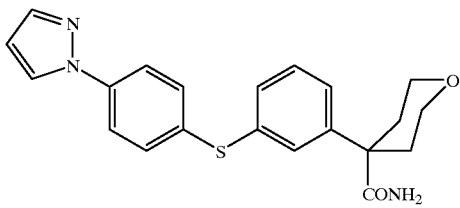
(1.1.3)

and

Tetrahydro-4-{3-[4-(4-methyl-1H-pyrazol-1-yl)phenyl]thio}phenyl-2H-pyran-4-carboxamide.

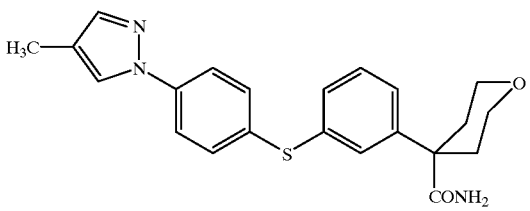
(1.1.4)

In order to prepare the above-mentioned compounds of Formulas (1.1.1)–(1.1.4) and similar compounds of this type, it is advantageous to use the following process of the present invention for preparing a compound of Formula (1.3.0):

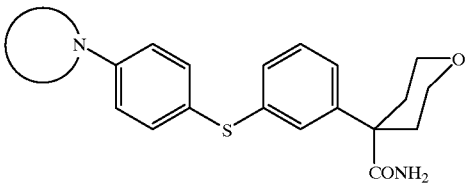
(1.3.0)

where
the moiety of Formula (1.3.1):

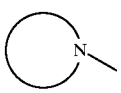
(1.3.1)

is an electron deficient monocyclic or benzo-fused bicyclic N-heterocyclic group containing two nitrogen atoms, of Formula (1.3.2) (1.3.3), (1.3.4) or (1.3.5):

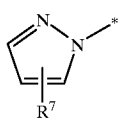
(1.3.2)

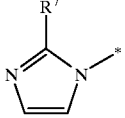
(1.3.3)

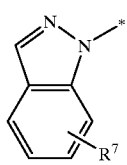
(1.3.4)

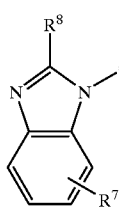
(1.3.5)

where
"*" is a symbol which represents the point of attachment of the moiety of Formula (1.3.2) (1.3.3), (1.3.4) or (1.3.5);

$R^7$ and $R^8$ are independently selected from the group consisting of H; straight or branched chain ($C_1$–$C_4$)alkyl; and ($C_6$–$C_{10}$)aryl; wherein said alkyl and aryl groups are substituted by 0 to 2 substituents selected from the group consisting of halo; hydroxy; cyano; amino; ($C_1$–$C_4$)alkyl; ($C_1$–$C_4$)alkoxy; ($C_1$–$C_4$)alkylthio; ($C_1$–$C_4$)halo-substituted alkyl; ($C_1$–$C_4$)halo-substituted alkoxy; ($C_1$–$C_4$)alkylamino; and di($C_1$–$C_4$)alkylamino.

The above-mentioned embodiment of the preparation process of the present invention may be illustrated by following SYNTHESIS SCHEME (10.2.0):

SYNTHESIS SCHEME (10.2.0)

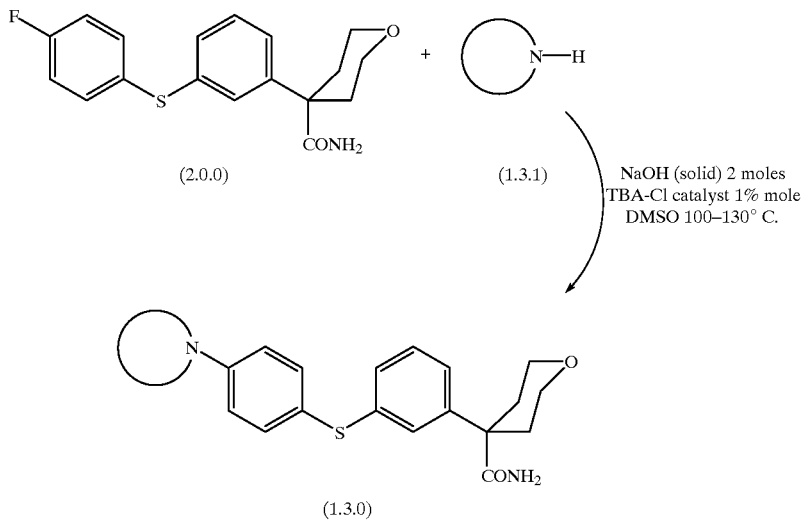

**+where the reactant of Formula (1.4.0):

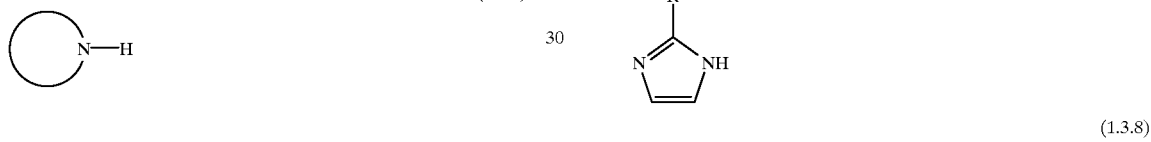

is an electron deficient monocyclic or benzo-fused bicyclic N-heterocycle containing two nitrogen atoms, of Formula (1.3.6) (1.3.7), (1.3.8) or (1.3.9), as defined further above.

Accordingly, the above-mentioned process of the present invention illustrated in SYNTHESIS SCHEME (10.2.0) may be carried out by:

(a) establishing a reaction mixture consisting of (1) tetrahydro-4-[3-(4-fluorophenyl)thio]phenyl-2H-pyran-4-carboxamide of Formula (2.0.0):

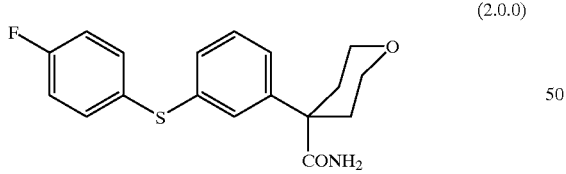

and (2) an electron deficient monocyclic or benzo-fused bicyclic N-heterocycle containing two nitrogen atoms, of Formula (1.3.6) (1.3.7), (1.3.8) or (1.3.9):

where $R^7$ and $R^8$ have the same meaning as set out above;

(3) in an aprotic solvent, preferably a member selected from the group consisting essentially of hexane; 1,4-dioxane; carbon tetrachloride; benzene; toluene; xylenes; diethyl ether; chloroform; ethyl acetate; tetrahydrofuran (THF); methylene chloride; hexamethylphosphoric triamide (HMPT); nitromethane; N,N-dimethylformamide (DMF); acetonitrile; sulfolane; and dimethylsulfoxide (DMSO); more preferably dimethylsulfoxide (DMSO);

(4) in the presence of a strong base in solid form selected from the group consisting of sodium hydroxide, NaOH; and potassium hydroxide, KOH;

and optionally (5) in the presence of a catalytic amount of cesium carbonate, $Cs_2CO_3$, or of a phase transfer catalyst, preferably a member selected from the group consisting of cetyltrimethylammonium bromide (CTMAB); dibenzo-18-crown-6 (DB-18-c-6); dicyclohexano-18-crown-6 (DC-18-c-6); 18-crown-6 (18-c-6); (—)-N-dodecyl-N-methylephedninium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide (TBAI); tetra-ethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC); and more preferably a quaternary ammonium salt or a phosphonium salt comprising a member of the above-recited group;

followed by (b) heating said reaction mixture, preferably at reflux, under a nitrogen atmosphere; whereby there is produced said compound of Formula (1.3.0).

As the person of ordinary skill in the art of preparing organic compounds of the type with which the present invention is concerned will recognize, displacement of aryl fluoride in the presence of base by an electron deficient nitrogen heterocycle is a relatively unknown method of forming carbon-nitrogen bonds, and is clearly one which has not been suggested heretofore as useful in preparing the types of compounds in question. Normally a strong electron withdrawing group, e.g., nitro, positioned para or ortho with respect to the fluorine atom, is required in order to achieve an acceptable level of displacement with a nitrogen nucleophile in the presence of base. Such displacement reactions typically afford only low yields, often require elevated temperatures and extended reaction times, and result in products requiring further purification. See, e.g., Morgan et al., *J. Med. Chem.*, 33, 1091–1097 (1990), which discloses a preparation method in which the methyl or ethyl ester of 4-fluoro-benzoic acid is reacted with the appropriate imidazole in DMSO using a base such as $K_2CO_3$, NaOH, or NaH. The 4-(2-methyl-1H-imidazol-1-yl)-benzoic acid ethyl ester compound was obtained in only 33% yield of unrecrystallized product. By contrast, the processes of preparation of the present invention give high yields, a result which is a wholly unexpected one because the aryl fluoride reactant in the processes of the present invention has no electron withdrawing substituents attached to the aryl ring.

The most preferred solvent for use in the above-described process of the present invention is dimethylsulfoxide (DMSO), although any aprotic solvent is suitable, and those recited above are preferred. In another preferred embodiment of the process, solid sodium hydroxide, NaOH, is used in the reaction mixture for which DMSO is the solvent. The strong base in solid form which is employed in this step of the preparation process of the present invention, is selected from sodium hydroxide, NaOH and potassium hydroxide, KOH. The term "solid" used in this connection is intended to refer to the phase in which the strong base which is present is to be found in the reaction mixture. Preferably, said solid is used in a sub-divided as opposed to unitary form, thereby providing a more extensive surface area upon which the other reactants are able to contact the strong base during the process step involved. Thus, the strong base in solid form may be used as a powder or as pellets. It is not necessary, on the other hand, that the solid form of the strong base be finely sub-divided. The solid forms of the strong base preferably used in the processes of the present invention are readily commercially available.

It is optional, but preferred, in this aryl fluoride displacement step of the processes of the present invention that a catalytic amount of cesium carbonate, $Cs_2CO_3$, or of a phase transfer catalyst ("PTC") also be employed. The amount used can vary between 0.5% and 10% mole, i.e., mole percent, but preferably will be between 1% and 5% mole. The amounts of catalyst which are suitable for use in the processes of the present invention can also be expressed as being in the range of from 0.005 to 0.5 equivalents, preferably from 0.01 to 0.1 equivalents, and more preferably about 0.05 equivalents, with reference to the other participants in the reaction.

Cesium carbonate, $Cs_2CO_3$, a material which is used as a catalyst in ethylene oxide polymerization and other catalyst assisted reactions, has been found to be a useful catalytic alternative to a phase transfer catalyst, as described herein.

The concentrations of the reactants in the same phase during this step can be less than optimal for convenient reaction rates to be achieved, and thus the use of a phase transfer catalyst can frequently be of benefit in reducing reaction temperatures and times. For example, when a phase transfer catalyst is used, the reaction may be carried out at 100° C. with a reaction time of 28 hours. Correspondingly, when the reaction temperature is 130° C. and a phase transfer catalyst is used, the reaction time is reduced to from 2 to 4 hours, with from 3 to 4 hours being required when a phase transfer catalyst is absent. It will be understood, nevertheless, that the present invention contemplates that solid NaOH or KOH may be used alone, i.e., without the use of a phase transfer catalyst.

There are two principal types of phase transfer catalyst based on their mode of action. The first type comprises quaternary ammonium salts or phosphonium salts, while the second type comprises crown ethers and other cryptands. Quaternary ammonium salts may comprise, in addition to the more typical aliphatic configurations, compounds in which the quaternized nitrogen atom is part of a heterocyclic ring system, e.g., a pyridinium or quininium salts. The first type of phase transfer catalyst, i.e., quaternary ammonium salts or phosphonium salts, are preferred for use as the phase transfer catalyst in the preparation processes of the present invention. Of this type, the quaternary ammonium salts are more preferred, and among these the most preferred phase transfer catalysts comprise a member selected from the group consisting of tetra-n-butylammonium bromide (TBAB); tetra-n-butylammonium chloride (TBAC); tetra-n-butylammonium hydroxide (TBAH); tetra-n-butylammonium iodide (TBAI); and tetra-ethylammonium chloride hydrate.

It will be appreciated that, notwithstanding the above-stated preferences as to the particular phase transfer catalysts which are selected for use in the preparation processes of the present invention, that there are a significant number of phase transfer catalysts which are known in the art and which are suitable for use in the present invention. The artisan will be well aware of the identity of such phase transfer catalysts as well as the appropriate steps by which their effectiveness in the preparation processes of the present invention may be demonstrated. For example, among phase transfer catalysts known in the art, the following are suitable for use in the preparation processes of the present invention: cetyltrimethylammonium bromide (CTMAB); dibenzo-18-crown-6 (DB-18-c-6); dicyclohexano-18-crown-6 (DC-18-c-6); 18-crown-6 (18-c-6); (—)-N-dodecyl-N-methylephedrinium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide (TBAI); tetraethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC).

The main mechanistic principle of phase transfer catalysis systems is continuous formation of lipophilic ion pairs of desired anions, with lipophilic cations supplied by the catalysts. The anions are thereby able to enter nonpolar organic media, in which the desired reaction takes place. Typical sources of lipophilic cations, which can act as catalysts in such systems, are tetraalkylammonium and other onium salts, crown ethers, cryptands, poly(ethylene glycol) ethers, and so forth. The fundamental nature of phase transfer catalysis is formation of lipophilic ion pairs, which can be found in nonpolar media. With highly lipophilic cations even small inorganic anions form such ion pairs. Phase transfer catalysis can function only in heterogeneous, mostly two-phase systems. In such systems an organic phase contains organic reactants and the catalyst, e.g., a lipophilic tetraalkylammonium chloride, whereas an aqueous, or in general inorganic, phase contains salts of desired anions or a base which can generate organic anions from corresponding precursors located in the organic phase.

In these systems catalysis consists of the transfer of the anions from the inorganic phase, or alternatively organic anions generated at the interface, to the organic phase, where they enter into the desired reaction, whereas the liberated catalyst can bring another anion into the organic phase. By continuous repetition of this action, 1 mol of the catalyst can promote conversion of $\geq 100$ mols or reactants. Depending upon the state of aggregation, kinds of anions, and some other factors, it is possible to differentiate a few variants of the above-described phase transfer catalytic process. Notwithstanding this, the skilled artisan will be able to readily adapt the basic requirements for carrying out phase transfer catalysis to the preparation processes of the present invention.

Returning now to the description of the preparation processes of the present invention, after the above-described reaction mixture is formed, it is heated to reflux under a nitrogen atmosphere. Under most ambient conditions, the reflux temperature of the reaction mixture will be from 120° to 140° C., usually from 125° to 135° C., and most usually 130° C.

It is necessary to heat the reaction mixture at the lower above-recited temperatures for a considerable period of time, from 12 to 30 hours, preferably from 16 to 24 hours, most preferably 18 to 20 hours. However, at the higher above-recited temperatures, the reaction proceeds more rapidly, and it is necessary to heat the reaction mixture for much shorter periods of time, from ½ to 4 hours, usually ¾ to 3 hours, and most typically from 1 to 2 hours.

The selection of a suitable temperature and time for carrying the reaction to completion are within the skill of the artisan knowledgeable in methods of organic synthesis. Isolation of the product of the above-described process, e.g., by vacuum filtration, washing with water, and drying in a vacuum oven, is accomplished using convention procedures which are likewise a matter of ordinary skill in the art. As further guidance for the artisan, there is provided herein the following table of values demonstrating different process yield results which have been obtained with solid sodium hydroxide mediated aryl fluoride displacements by 2-methylimidazole:

TABLE (11.0.0)

| Reaction Conditions | %[1] Yield | % Purity of (1.0.0)[2] | Isolated % Yield[3] | % Residual (2.0.0) |
|---|---|---|---|---|
| Solid NaOH, powdered; TBAC[4] 5% mole; 100° C. | 93 | 98.9 | 92.3 | 1.7 |
| Solid NaOH, powdered; TBAC 5% mole; 130° C. | 92 | 102.7 | 94.5 | 0.86 |
| Solid NaOH, pellets; TBAC 5% mole; 130° C. | 92 | 99.9 | 91.6 | 0.94 |
| Solid NaOH, powdered; TBAC 1% mole; 130° C. | 94 | 93.9 | 88.1 | 1.26 |
| Solid NaOH, pellets; 130° C. | 85 | 87.3 | 73.9 | 0.92 |
| Solid NaOH, pellets; 130° C. | 90 | 99.4 | 89.9 | 0 |
| Solid NaOH, powdered; TBAC 1% mole; water 0.1 vol.; 130° C. | 93 | 95.2 | 88.4 | 0.43 |
| Solid NaOH, powdered; TBAC 1% mole; 130° C. | 90.5 | 98.0 | 88.7 | 0.46 |

[1]All percentages are by weight.
[2]Measured by HPLC.
[3]HPLC based.
[4]TBAC = tetra-n-butylammonium chloride.

An alternative process to that described immediately above for preparing the compound of Formula (1.3.0) is also an embodiment of the preparation processes of the present invention, although the process described immediately above is the preferred embodiment of the present invention for preparing the compound of Formula (1.3.0). The alternative process may be illustrated by the following SYNTHESIS SCHEME (10.2.1):

SYNTHESIS SCHEME (10.2.1)

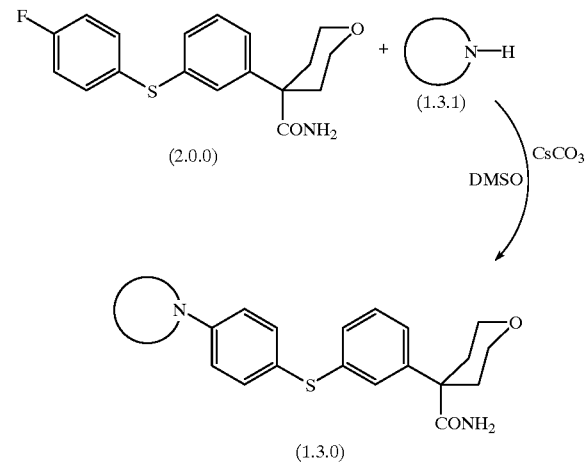

where the moiety of following Formula (1.3.1):

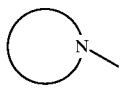

(1.3.1)

is an electron deficient monocydic or benzo-fused bicyclic N-heterocyclic group containing two nitrogen atoms, of Formula (1.3.2) (1.3.3), (1.3.4) or (1.3.5):

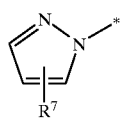

(1.3.2)

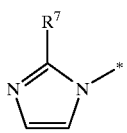

(1.3.3)

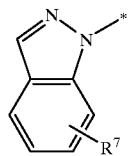

(1.3.4)

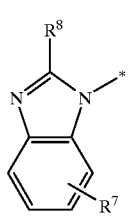

(1.3.5)

where

"*" is a symbol which represents the point of attachment of the moiety of Formula (1.3.2) (1.3.3, (1.3.4) or (1.3.5);

$R^7$ and $R^8$ are independently selected from the group consisting of H; straight or branched chain $(C_1-C_4)$alkyl; and $(C_6-C_{10})$aryl; wherein said alkyl and aryl groups are substituted by 0 to 2 substituents selected from the group consisting of halo; hydroxy; cyano; amino; $(C_1-C_4)$alkyl; $(C_1-C_4)$alkoxy; $(C_1-C_4)$alkylthio; $(C_1-C_4)$halo-substituted alkyl; $(C_1-C_4)$halo-substituted alkoxy; $(C_1-C_4)$alkylamino; and di$(C_1-C_4)$alkylamino;

comprising:

(a) establishing a reaction mixture consisting of (1) tetrahydro-4-[3-(4-fluorophenyl)thio]phenyl-2H-pyran-4-carboxamide of Formula (2.0.0):

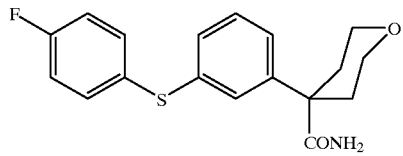

(2.0.0)

and (2) an electron deficient monocyclic or benzo-fused bicyclic N-heterocycle containing two nitrogen atoms, of Formula (1.3.6) (1.3.7), (1.3.8) or (1.3.9):

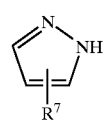

(1.3.6)

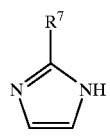

(1.3.7)

(1.3.8)

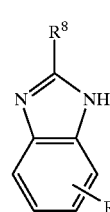

(1.3.9)

where $R^7$ and $R^8$ have the same meaning as set out above;

(3) in an aprotic solvent, preferably dimethylsulfoxide (DMSO);

(4) in the presence of a carbonate of Formula (5.1.0):

$$(M)_2\text{-}CO_3 \qquad (5.1.0)$$

where M has the same meaning as defined further above, which is preferably cesium carbonate, $Cs_2CO_3$;

followed by (b) heating said reaction mixture, preferably at reflux, under a nitrogen atmosphere; whereby there is produced a compound of Formula (1.3.0).

It will be noted that in the above-recited processes of the present invention, that one of the key reactants is the compound of Formula (2.0.0):

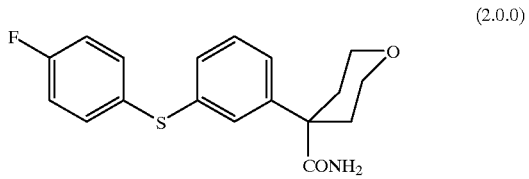

(2.0.0)

This compound is also a novel intermediate of the present invention, tetrahydro-4-[3-(4-fluorophenyl)thio]phenyl-2H-pyran4-carboxamide. In order to carry out the above-recited process of the present invention, it is thus necessary to provide a process by which this novel reactant/intermediate itself may be prepared. Accordingly, there follows a description of another process of the present invention by means of which the compound of Formula (2.0.0) is produced.

The present invention is further concerned with a process for preparing a compound of Formula (2.0.0):

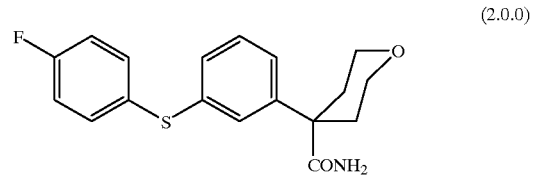

(2.0.0)

One of the preferred processes of the present invention for preparing the novel intermediate of Formula (2.0.0) may be illustrated by the following SYNTHESIS SCHEME (10.0.1):

SYNTHESIS SCHEME (10.0.1)

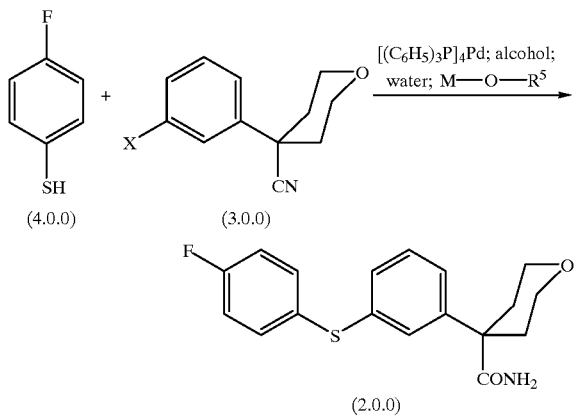

where X, M, and $R^5$ all have the same meaning as defined elsewhere herein.

Accordingly, the above-mentioned process of the present invention illustrated in SYNTHESIS SCHEME (10.0.1) may be carried out by:

(a) establishing a reaction mixture consisting of (1) tetrahydro-4-(3-bromo- or iodo-phenyl)-2H-pyran-4-nitrile of Formula (3.0.0):

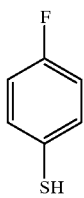

(3.0.0)

where X is bromo or iodo;
and
(2) 4-fluorothiophenol of Formula (4.0.0):

(4.0.0)

(3) in a solvent consisting of a straight or branched chain aliphatic alcohol having a total of from 2 to 7 carbon atoms, optionally as an aqueous mixture thereof, and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;

(4) in the presence of strong base of Formula (5.0.0):

$$M\text{-}O\text{-}R^5 \qquad (5.0.0)$$

where
M is an alkali metal, Group 1/Ia element, selected from the group consisting of lithium, Li; sodium, Na; potassium, K; rubidium, Rb; and cesium, Cs; and $R^5$ is hydrogen, H; or straight or branched chain ($C_1$–$C_4$) alkyl; preferably a member selected from the group consisting of lithium hydroxide, LIOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$; including mixtures of the above;
and further (5) in the presence of a transition metal catalyst comprising a palladium metal complex, preferably one which is a member selected from the group consisting of tetrakis(triphenylphosphine)palladium(0), $[(C_6H_5)_3P]_4Pd(0)$;
tetrakis(methyldiphenylphosphine)palladium(0), $[(C_6H_5)_2PCH_3]_4Pd(0)$;
trans-dichlorobis(methyldiphenylphosphine)palladium(II), $[(C_6H_5)_2PCH_3]_2PdCl_2$;
dichlorobis[methylenebis(diphenylphosphine)]dipalladium-dichloromethane adduct;
dichlorobis(triphenylphosphine)palladium(II), $[(C_6H_5)_3P]_2PdCl_2$;

tris(dibenzylideneacetone)dipalladium(0)-chloroform adduct, $(C_6H_5CH=CHCOCH=CHC_6H_5)_3Pd_2 \cdot CHCl_3$; bis(dibenzylideneacetone)palladium(0), $(C_6H_5CH=CHCOCH=CHC_6H_5)_2Pd$; [1,1'-bis(diphenylphosphino)ferrocene]dichloropalladium (II), complex with dichloromethane bis[1,2-bis(diphenylphosphino)ethane]palladium(II); and (π-allyl)palladium(II) chloride dimer; and still further (6) in the presence of an auxiliary ligand for said transition metal catalyst comprising a palladium metal complex, wherein said ligand is a bidentate, chiral, axially dissymmetric aromatic compound of Formula (5.5.0) or (5.5.1):

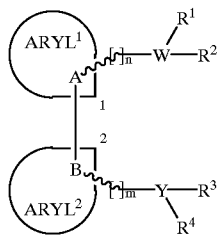

(5.5.0)

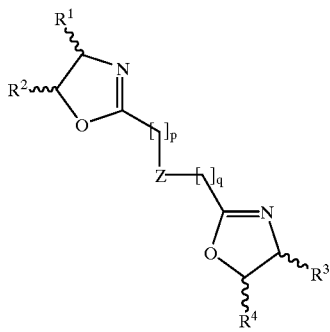

(5.5.1)

where in Formula (5.5.0): W and Y are both phosphorus or are both nitrogen, or taken together with $R^1$, $R^2$, $R^3$, and $R^4$ are hydrogen phosphate; m and n are independently 1 or 2; $R^1$, $R^2$, $R^3$, and $R^4$ are independently selected from the group consisting of hydrogen; $(C_1-C_4)$alkyl, phenyl; naphthyl; biphenyl; tolyl; furyl; pyrrolyl; and pyridyl; $ARY^1$ and $ARYL^2$ are independently selected from the group consisting of phenyl; biphenyl; 1- or 2-naphthyl; pyridyl; and quinolinyl; or $ARYL^1$ and $ARYL^2$ are taken together to form a phenyl; naphthyl; biphenyl; pyridyl; quinolinyl; or cyclohexyl group; A and B are both carbon atoms which are either bonded directly to carbon atoms identified as 1 and 2, or else are adjacent constituent carbon atoms identified as 1 and 2 of $ARYL^1$ and $ARYL^2$, respectively, in which case the bonds attached to A and B of unspecified orientation are attached to carbon atoms α to carbon atoms identified as 1 and 2; and said bonds of unspecified orientation must have opposite orientations, whereby said auxiliary ligand is axially dissymmetric; and in Formula (5.5.1): p and q are independently 0, 1 or 2; $R^1$, $R^2$, $R^3$, and $R^4$ have the same meaning as above selected on an independent basis; Z is $—N(R^5)—$ or $—(CH_2)—$ where $R^5$ is hydrogen or $(C_1-C_4)$alky; provided that p and q cannot be 0 when Z is $—N(R^5)—$; and for the bonds of unspecified orientation attached to $R^1$, $R^2$, $R^3$, and $R^4$, said bonds of $R^1$ and $R^2$ must have an orientation opposite to that of said bonds of $R^3$ and $R^4$, whereby said auxiliary ligand is axially dissymmetric;

preferably, said auxiliary ligand is (S-(—)-2,2'-bis(diphenylphosphino)-1,1'-binaphthyl (S-BINAP); followed by (b) heating said reaction mixture, preferably at reflux, preferably for a period of from 12 to 36 hours, more preferably from 18 to 24 hours; whereby there is produced said compound of Formula (2.0.0) which is optionally isolated using conventional separation techniques.

The above-described process is one which prepares an asymmetrically substituted diarylether. At the same time, the reaction which takes place also results in the hydrolysis of the nitrile substituent to the corresponding carboxamide substituent. It has been found that several factors are important in securing completion of the above-described process with acceptable yields of the novel intermediate of Formula (2.0.0).

One such factor is the solvent in which the reaction involved is carried out. The solvent consists of a straight or branched chain aliphatic alcohol having a total of from 2 to 7 carbon atoms. The alcohol solvent may also be used in admixture with water, ie., as an aqueous mixture of the alcohol in suitable proportions. While the alcohol solvent and water are miscible in almost all proportions, it has been found desirable to maintain the volume to volume ratio of alcohol to water, respectively, in the range of from 25 to 1, to 3 to 1, preferably in the range of from 10 to 1; to 5 to 1.

It has also been found that the most suitable straight or branched chain aliphatic alcohol having a total of from 2 to 7 carbon atoms, for use as the solvent in the process of the present invention is a secondary alcohol selected from the group consisting of iso-propyl alcohol, sec-butyl alcohol, iso-pentyl alcohol, and 2-heptanol. Of these preferred secondary alcohols, the iso-propyl alcohol is the most preferred. The above-mentioned secondary alcohols are also optionally utilized as an aqueous mixture, as described in detail above.

It will be appreciated that the reaction temperature employed in the above-described process of the present invention can be regulated by choosing the alcoholic solvent, depending in turn on the degree of reactivity of the substrate. For example, for the reactant of Formula (3.0.0), where X has the meaning iodo, it has been found that the reaction can be carried out smoothly in refluxing iso-propyl alcohol. For the reactant of Formula (3.0.0), where X has the meaning bromo, it has been found that the reaction can be carried out smoothly in refluxing sec-butyl alcohol. It will also be appreciated that the reaction involving aryl iodide in the above-described process of the present invention, i.e., where X has the meaning iodo in the reactant of Formula (3.0.0), proceeds rapidly and can be completed in a period of a few hours' time. The reaction involving aryl bromide, on the other hand, i.e., where X has the meaning bromo in the reactant of Formula (3.0.0), proceeds more slowly than the reaction involving aryl iodide, and heating of the reaction mixture for a significantly longer period of time, more than 10 hours, is required to complete the reaction. However, prolonged heating of the reaction mixture in the case of either reaction, does not adversely affect the yield of the resulting diaryl thioether, ie., diaryl sulfide.

Another such factor is the use of a strong base of Formula (5.0.0):

$$M-O-R^5 \qquad (5.0.0)$$

where M is an alkali metal, Group 1/Ia element, selected from the group consisting of lithium, Li; sodium, Na; potassium, K; rubidium, Rb; and cesium, Cs; and $R^5$ is hydrogen, H; or straight or branched chain $(C_1-C_4)$alkyl.

Prefered strong bases comprise a member selected from the group consisting of lithium hydroxide, LiOH; sodium hydroxide, NaOH; potassium hydroxide, KOH; rubidium hydroxide, RbOH; cesium hydroxide, CsOH; lithium methoxide, LiOCH$_3$; sodium methoxide, NaOCH$_3$; potassium methoxide, KOCH$_3$; rubidium methoxide, RbOCH$_3$; cesium methoxide, CsOCH$_3$; lithium ethoxide, LiOCH$_2$CH$_3$; sodium ethoxide, NaOCH$_2$CH$_3$; potassium ethoxide, KOCH$_2$CH$_3$; rubidium ethoxide, RbOCH$_2$CH$_3$; cesium ethoxide, CsOCH$_2$CH$_3$; lithium tert-butoxide, LiOC(CH$_3$)$_3$; sodium tert-butoxide, NaOC(CH$_3$)$_3$; potassium tert-butoxide, KOC(CH$_3$)$_3$; rubidium tert-butoxide, RbOC(CH$_3$)$_3$; and cesium tert-butoxide, CsOC(CH$_3$)$_3$.

The above-mentioned strong bases may be used in the form of mixtures thereof, but it is preferred to employ only a single strong base. More preferred among the above-recited strong bases are sodium hydroxide, NaOH; potassium hydroxide, KOH; sodium ethoxide, NaOCH$_2$CH$_3$; and potassium tert-butoxide, KOC(CH$_3$)$_3$.

A still further factor in achieving satisfactory completion of the above-described process of the present invention is the use of a transition metal catalyst comprising palladium metal complexes. Included among the palladium metal complexes which are preferred for use in the process of the present invention, are more preferred species of such catalysts which are used in the above-described process. Said more preferred species is a member selected from the group consisting of:

tetrakis(triphenylphosphine)palladium(0): [(C$_6$H$_5$)$_3$P]$_4$Pd(0);

tetrakis(methyldiphenylphosphine)palladium(0): [(C$_6$H$_5$)$_2$PCH$_3$]$_4$Pd(0);

trans-dichlorobis(methyldiphenylphosphine)palladium(II): [(C$_6$H$_5$)$_2$PCH$_3$]$_2$PdCl$_2$;

dichlorobis[methylenebis(diphenylphosphine)]dipalladium-dichloromethane adduct of Formula (6.0.0):

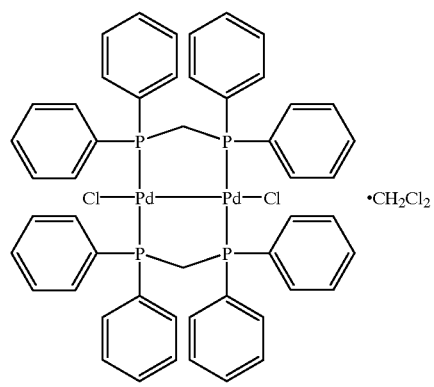

(6.0.0)

dichlorobis(triphenylphosphine)palladium(II): [(C$_6$H$_5$)$_3$P]$_2$PdCl$_2$;

tris(dibenzylideneacetone)dipalladium(0)-chloroform adduct: (C$_6$H$_5$CH=CHCOCH=CHC$_6$H$_5$)$_3$Pd$_2$·CHCl$_3$;

bis(dibenzylideneacetone)palladium(0): (C$_6$H$_5$CH=CHCOCH=CHC$_6$H$_5$)$_2$Pd;

[1,1'-bis(diphenylphosphino)ferrocene]dichloropalladium(II), complex with dichloromethane, of Formula (6.1.0):

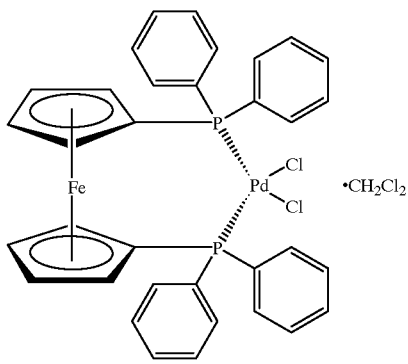

(6.1.0)

bis[1,2-bis(diphenylphosphino)ethane]palladium(II) of Formula (6.2.0):

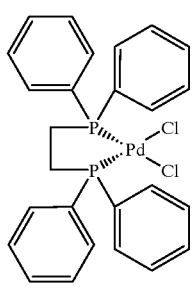

(6.2.0)

and
(π-allyl)palladium(II) chloride dimer of Formula (6.3.0):

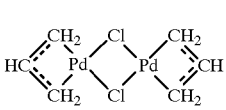

(6.3.0)

Of the palladium metal complexes described above, the most preferred is tetrakis(triphenylphosphine)palladium(0), [(C$_6$H$_5$)$_3$P]$_4$Pd(0).

The most important factor in achieving satisfactory completion of the above-described process of the present invention is the use of an auxiliary ligand for the transition metal catalyst comprising a palladium metal complex. It has been discovered that with the selection and use of a particular type of auxiliary ligand, that the efficiency and product yields of the above-described process can be very substantially improved. The particular type of ligand to be selected and used is a bidentate, chiral, axially dissymmetric aromatic compound. Such an auxiliary ligand operates in conjunction with said transition metal catalyst comprising a palladium metal complex, to drive and guide the mechanisms through which the reactions in the processes of the present invention are taking place. More details concerning the actual and conjectured workings of the auxiliary ligand in the processes of the present invention are presented further below.

The auxiliary ligand to be selected and used together with the transition metal catalyst comprising a palladium metal complex in the processes of the present invention is a bidentate, chiral, axially dissymmetric aromatic compound of Formula (5.5.0) or (5.5.1):

(5.5.0)

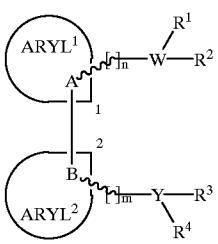

(5.5.0)

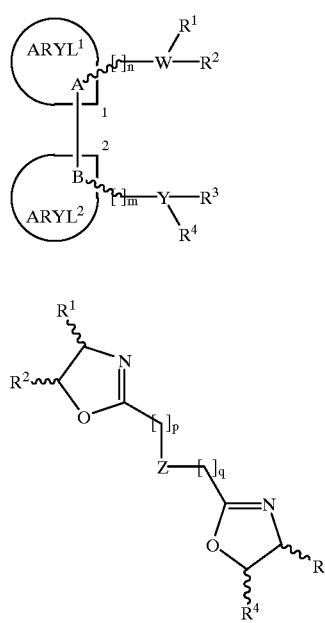

(5.5.1)

where in Formula (5.5.0): W and Y are both phosphorus or are both nitrogen, or taken together with $R^1$, $R^2$, $R^3$, and $R^4$ are hydrogen phosphate; m and n are independently 1 or 2; $R^1$, $R^2$, $R^3$, and $R^4$ are independently selected from the group consisting of hydrogen; $(C_1-C_4)$alkyl; phenyl; naphthyl; biphenyl; tolyl; furyl; pyrrolyl; and pyridyl; ARYL$^1$ and ARYL$^2$ are independently selected from the group consisting of phenyl; biphenyl; 1- or 2-naphthyl; pyridyl; and quinolinyl; or ARYL$^1$ and ARYL$^2$ are taken together to form a member selected from the group consisting of phenyl; naphthyl; biphenyl; pyridyl; quinolinyl; and 2,2-dimethyl-1,3-dioxolane-4,5-diyl; A and B are both carbon atoms which are either bonded directly to carbon atoms identified as 1 and 2, or else are adjacent constituent carbon atoms identified as 1 and 2 of ARYL$^1$ and ARYL$^2$, respectively, in which case the bonds attached to A and B of unspecified orientation are attached to carbon atoms α to carbon atoms identified as 1 and 2; and said bonds of unspecified orientation must have opposite orientations, whereby said auxiliary ligand is axially dissymmetric; and in Formula (5.5.1): p and q are independently 0, 1 or 2; $R^1$, $R^2$, $R^3$, and $R^4$ have the same meaning as above selected on an independent basis; Z is —N(R$^5$)— or —(CH$_2$)— where $R^5$ is hydrogen or $(C_1-C_4)$alkyl; provided that p and q cannot be 0 when Z is —N(R$^5$)—; and for the bonds of unspecified orientation attached to $R^1$, $R^2$, $R^3$, and $R^4$, said bonds of $R^1$ and $R^2$ must have an orientation opposite to that of said bonds of $R^3$ and $R^4$, whereby said auxiliary ligand is axially dissymmetric.

With regard to the auxiliary ligands of Formula (5.5.0):

the moieties ARYL$^1$ and ARYL$^2$ are independently selected from the group consisting of phenyl; biphenyl; 1- or 2-naphthyl; pyridyl; and quinolinyl; while A and B are both carbon atoms which are either bonded directly to carbon atoms identified as 1 and 2, or else are adjacent constituent carbon atoms identified as 1 and 2 of ARYL$^1$ and ARYL$^2$, respectively, in which case the bonds attached to A and B of unspecified orientation are attached to carbon atoms α to carbon atoms identified as 1 and 2; and said bonds of unspecified orientation must have opposite orientations, whereby said auxiliary ligand is axially dissymmetric.

In preferred embodiments, A and B form adjacent constituent parts of ARYL$^1$ and ARYL$^2$, and this requirement results in a configuration in which the aromatic groups which make up the ARYL$^1$ and ARYL$^2$ moieties are bound to each other by a carbon-to-carbon covalent bond. This arrangement of the planar aromatic groups provides additional rigidity, which is thought to further promote the enantioselectivity facilitated by the opposite orientation of the bonds on the other side of A and B. Examples of these preferred embodiments, as well as the less preferred embodiments wherein A and B are bonded directly to ARYL$^1$ and ARYL$^2$, may be illustrated by the following moieties of partial Formulas (5.6.1) through (5.6.9):

(5.6.1)

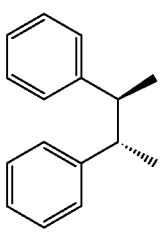

(5.6.2)

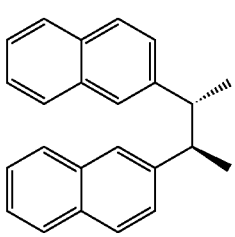

(5.6.3) 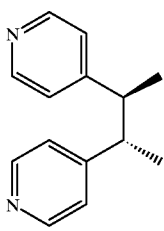

(5.6.4) 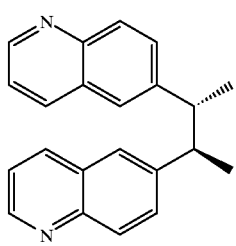

(5.6.5) 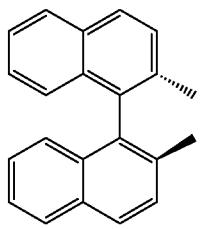

(5.6.6) 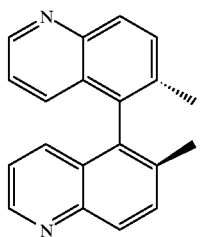

(5.6.7) 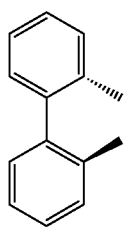

(5.6.8) 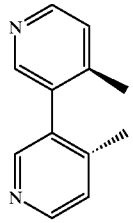

(5.6.9) 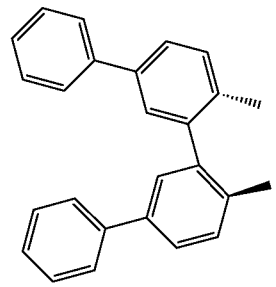

In preferred embodiments of the present invention, both m and n are 1 and both W and Y are phosphorus or taken together with $R^1$, $R^2$, $R^3$, and $R^4$ are hydrogen phosphate. A preferred hydrogen phosphate species has a 1,1'-binaphthyl group and is represented by Formula (5.7.1):

(5.7.1) 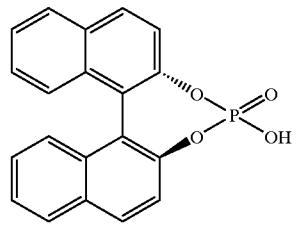

Preferred phosphorus species are those wherein $R^1$, $R^2$, $R^3$, and $R^4$ are the same and are phenyl, p-tolyl, or pyridyl. When these preferences are combined with a 1,1'-binaphthyl group as a preferred embodiment of A and B, and $ARYL^1$ and $ARYL^2$, the following preferred species of the auxiliary ligand of Formula (5.5.0) result, as shown in Formulas (5.7.2) through (5.7.4):

(5.7.2) 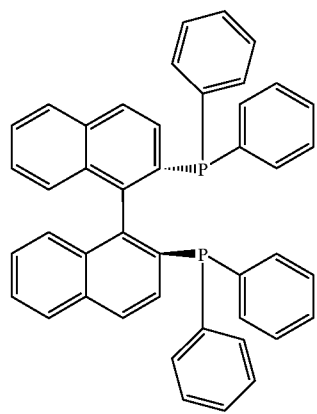

-continued (5.7.3)

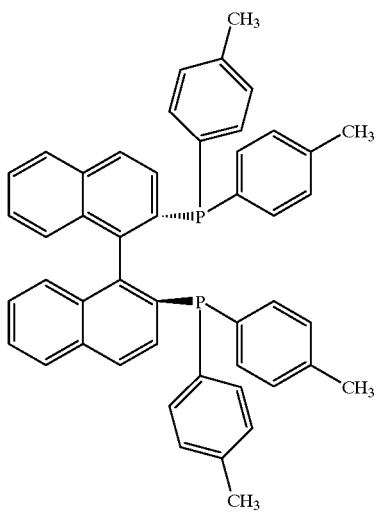

(5.7.4)

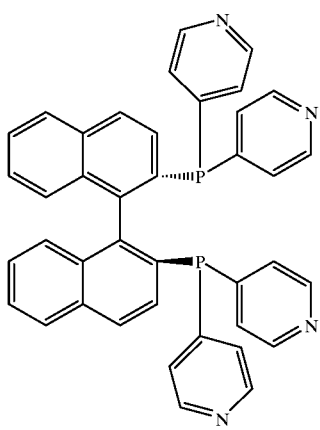

from the group consisting of phenyl; naphthyl; biphenyl; pyridyl; quinolinyl; and 2,2-dimethyl-1,3-dioxolane-4,5-diyl. In these embodiments, A and B are adjacent constituent carbon atoms of said members. Using the preferred bis (diphenyl-phosphino) moiety illustrated above, e.g., in the species of Formula (5.7.2), the following further auxiliary ligand embodiments of the present invention result, as shown in Formulas (5.7.5) through (5.7.9):

(5.7.5)

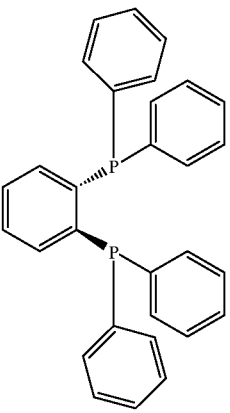

(5.7.6)

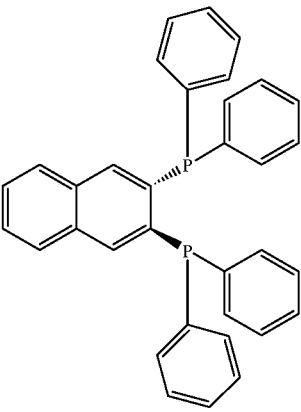

In further embodiments of the auxiliary ligands used in the preparation processes of the present invention, $ARYL^1$ and $ARYL^2$ are taken together to form a member selected With regard to the auxiliary ligands of Formula (5.5.1):

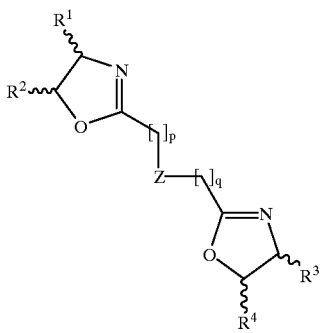
(5.5.1)

(5.7.7)
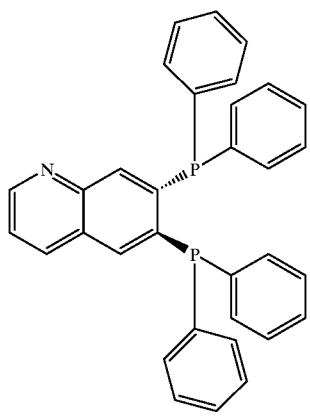

(5.7.8)
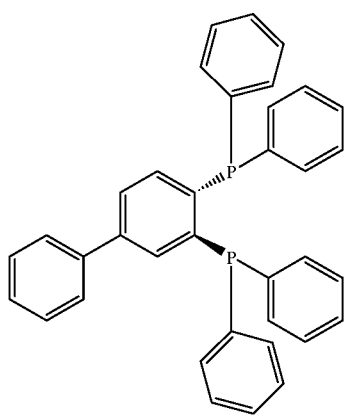

p and q are independently 0, 1 or 2; $R^1$, $R^2$, $R^3$, and $R^4$ are independently selected from the group consisting of hydrogen; $(C_1-C_4)$alkyl; phenyl; naphthyl; biphenyl; tolyl; furyl; pyrrolyl; and pyridyl; Z is —N($R^5$)— or —($CH_2$)— where $R^5$ is hydrogen or $(C_1-C_4)$alkyl; provided that p and q cannot be 0 when Z is —N($R^5$)H—; and for the bonds of unspecified orientation attached to $R^1$, $R^2$, $R^3$, and $R^4$, said bonds of $R^1$ and $R^2$ must have an orientation opposite to that of said bonds of $R^3$ and $R^4$, whereby said auxiliary ligand is axially dissymmetric.

Preferred embodiments of the auxiliary ligands of Formula (5.5.1) include those where p and q are both 0, Z is $CH_2$, and $R^1$, $R^2$, $R^3$, and $R^4$ are all defined as phenyl or $R^2$ and $R^4$ are hydrogen while $R^1$ and $R^3$ are phenyl. The resulting preferred embodiments are the species of Formulas (5.8.1) and (5.8.2):

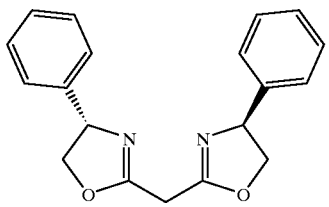
(5.8.1)

(5.7.9)
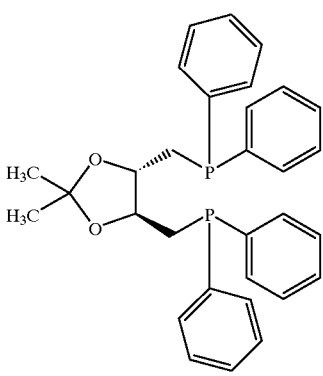

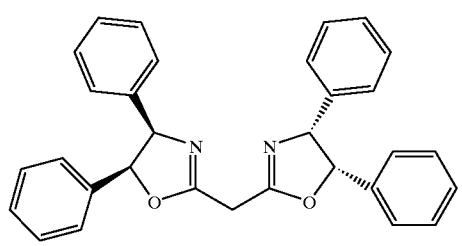
(5.8.2)

The auxiliary ligand species of Formula (5.7.9) above is (+)-2,3-O-isopropylidene-2,3-dihydroxy-1,4-bis(diphenylphospino)-butane, which is a commercially available material.

The species of Formula (5.8.1) is 2,2'-methylenebis[(4S)-4-phenyl-2-oxazoline]; and the species of Formula (5.8.2) is 2,2'-methylenebis[(4R,5S)-4,5-diphenyl-2-oxazoline]. Both species are commercially available materials.

Other embodiments of the auxiliary ligands used in the preparation processes of the present invention include those where Z is $NR^5$ where $R^5$ is hydrogen; p and q are both 1; and $R^1$, $R^2$, $R^3$, and $R^4$ are all defined as phenyl or $R^2$ and $R^4$ are hydrogen while $R^1$ and $R^3$ are phenyl. The resulting preferred embodiments are the species of Formulas (5.8.3) and (5.8.4): (5.8.3) (5.8.4)

(5.8.3)

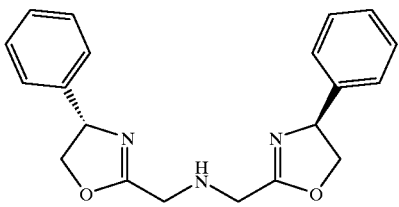

(5.8.4)

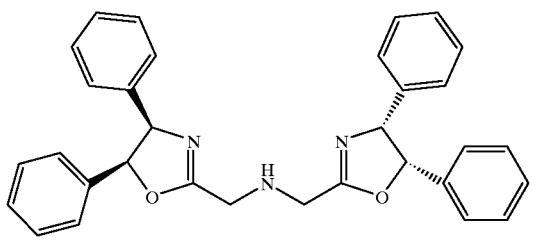

The palladium catalyzed coupling reaction of thiophenols and aryliodides to yield diarylthioethers was first reported by Migita, et al. in *Bull. Chem. Soc. Jpn.* 53, 1385–1389 (1980). In the Migita reaction as it relates to the preparation processes of the present invention, the bromo-nitrile is converted into the fluoro-amide, as is illustrated by SYNTHESIS SCHEME (10.0.1) set out further above and repeated in the discussion immediately below.

The catalytic cycle for the Migita reaction shares some similarities with the Heck reaction in that the active catalytic species is believed to be a 14 electron Pd(0) with two phosphorus ligands attached. See, e.g., Classics in Total Synthesis, K. C. Nicolaou and E. J. Sorensen, page 567, VCH 1996, Weinheim, Germany, New York, USA, Basel, Switzerland, Cambridge, England, Tokyo, Japan. The catalytic cycle of the Migita Reaction is illustrated in the following SYNTHESIS SCHEME (10.4.0):

SYNTHESIS SCHEME (10.4.0)

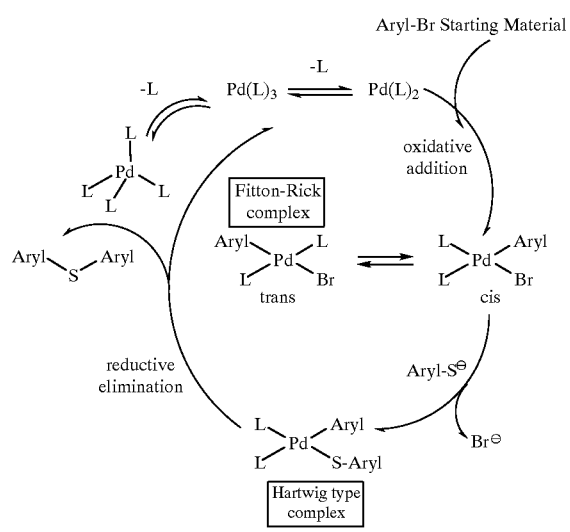

The discovery and isolation of the palladium-sulfur addition complex derived from the corresponding thiophenol and aryliodide starting materials, has been reported by Hartwig, et al. in *J. Am. Chem. Soc.* 120, 9205–9219 (1998). It is conjectured that the Hartwig complex is the precursor from which the diarylthioethers are expelled by reductive elimination and the 14 electron Pd(0) intermediate is regenerated to maintain the catalytic cycle. Application of this catalyzed sequence to the processes of the present invention is illustrated in SYNTHESIS SCHEME (10.0.1) further above and repeated here:

SYNTHESIS SCHEME (10.0.1)

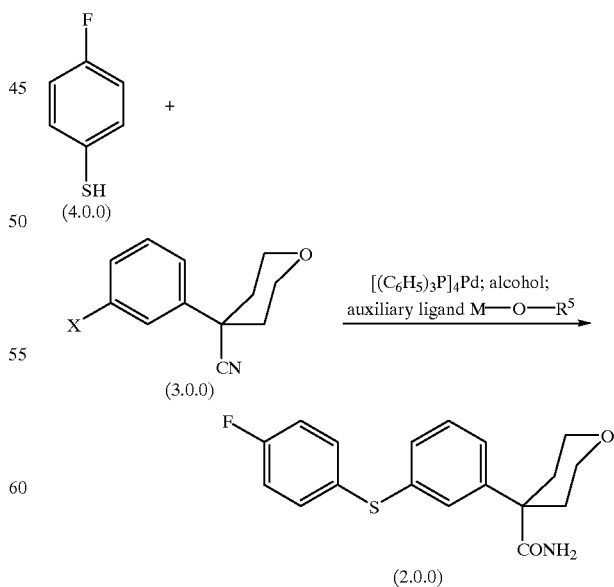

As has already been pointed out herein, in addition to the modified Migita reaction, the reaction in SYNTHESIS SCHEME (10.0.1) also involves simultaneous nitrile into amide hydrolysis. This is a desired chemical transformation which enhances the elegance and brevity of the overall synthesis of the compound of Formula (1.0.0), but it is mechanistically more complicated than the catalyzed sequence without said transformation. In order to understand the underlying mechanism of action and to assure the reproducibility of the carbon-sulfur reaction behavior and auxiliary ligand effects just described, a more simple model of the catalyzed sequence was contrived in accordance with the following SYNTHESIS SCHEME (10.5.0):

points of reaction yield, with improvement in the reaction rate when an auxiliary ligand was added. The optimum completion time for the reaction of SYNTHESIS SCHEME (10.0.1) was estimated at 6–7 hours when (S)-BINAP was used as the auxiliary ligand, compared to >16 hours when no auxiliary ligand was added. For the reaction of SYNTHESIS SCHEME (10.5.0) the optimum completion time was estimated at ~6 hours when (S)-BINAP was used as the auxiliary ligand, compared to >18 hours when no auxiliary ligand was present. These data are summarized in the following GRAPH (12.0.0) and GRAPH (12.0.1) and their corresponding TABLE (11.0.1) and TABLE (11.0.2):

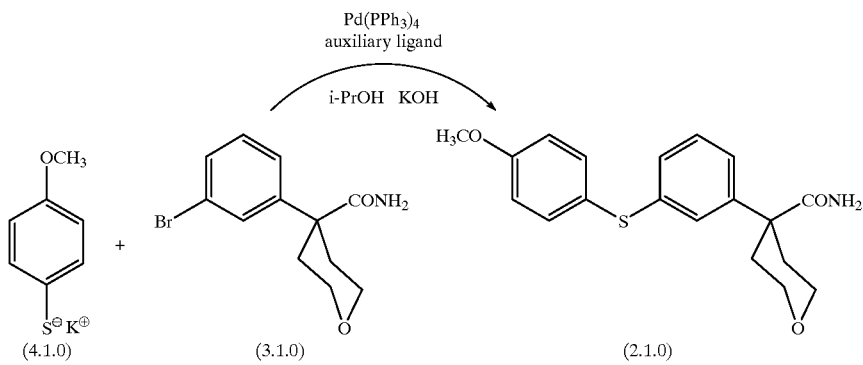

SYNTHESIS SCHEME (10.5.0)

The model represented by SYNTHESIS SCHEME (10.5.0) was carried out using 1% mole of the transition metal catalyst complex, Pd(PPh$_3$)$_4$, which contains only 9% palladium on a mass basis. This fixed minimal amount of palladium was chosen in order to reduce costs and to control the amount of residual palladium found in the final product, as well as to establish a predetermined amount of palladium that had to be removed in downstream processing. The objective was to determine whether a significant reaction rate enhancement could be obtained by the addition of catalytic amounts of auxiliary ligands. For this study 2,2'-bis(diphenylphosphino)-1,1'-binaphthyl (BINAP) was selected as the auxiliary ligand, and it was used at 2% moles. The principal reactants, the thiophenol and the arylbromide, were reacted together in equimolar proportions, and the catalyst, Pd(PPh$_3$)$_4$, was used at a 1% mole level. The base, potassium hydroxide, was used at 2 moles relative to the arylbromide. The solvent used was iso-propanol, and in some instances, 2 moles of water were added relative to the arylbromide. The reactions were carried out at –82° C.

The reactions represented by SYNTHESIS SCHEMES (10.0.1) and (10.5.0) both showed a yield increase of >10%

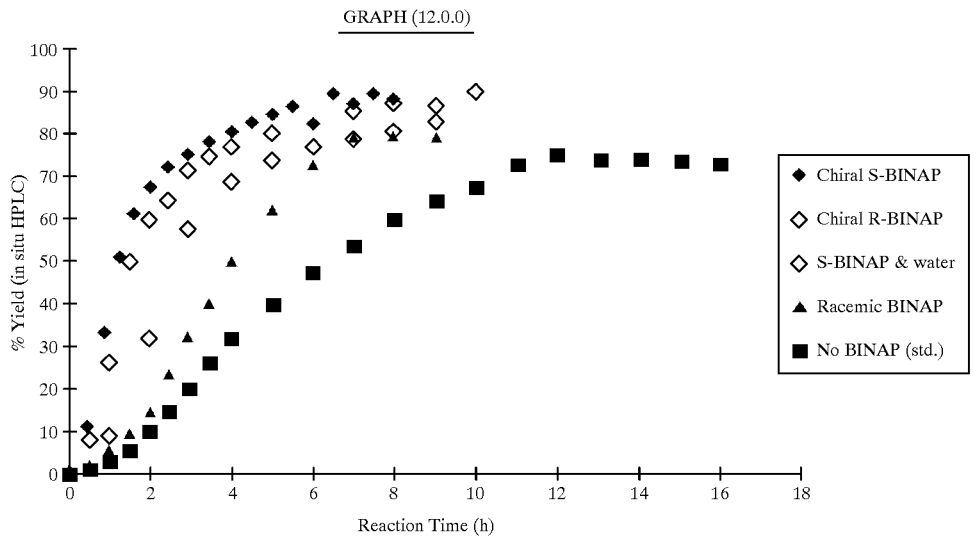
GRAPH (12.0.0)
| Time (hr) | Chiral (S)-BINAP | Racemic BINAP | No BINAP | Chiral (R)-BINAP |
|---|---|---|---|---|
| 0 | 0.2 | 0.7 | 0.04 | 0.6 |
| 0.5 | 5 | 6.6 | 3.3 | 5.3 |
| 1 | 17.5 | 14.4 | 7.0 | 11.3 |
| 1.5 | 32.3 | 20.5 |  | 19.1 |
| 2.0 | 37 | 25.8 | 17.7 | 22.0 |
| 2.5 | 51.4 | 28.0 |  | 26.7 |
| 3.0 | 56.8 | 33.4 | 21.9 | 31.1 |
| 3.5 | 62.4 | 45.2 |  | 32 |
| 4.0 | 69.8 | 52.5 | 31.9 | 41.7 |
| 5.0 | 77.3 | 51.5 | 41.2 | 52.0 |
| 6.0 | 82.4 | 58.7 | 45.4 | 60.1 |
| 7.0 | 85.9 | 64.7 | 52.4 | 67 |
| 8.0 | 85.7 | 70.6 | 57.1 | 70.9 |
| 9.0 | 83.8 | 76.8 | 63.1 | 77.7 |
| 10.0 | 80.9 | 77.7 | 67.4 | 76.7 |
| 11.0 |  | 82.0 | 68.2 | 75.7 |
| 13.0 |  |  | 71.7 | 74.2 |
| 12.0 |  | 81.2 |  | 76.7 |
| 15.0 |  |  | 73.8 |  |
| 17.0 |  |  | 75.2 |  |
| 19.0 |  |  | 73.2 |  |
| 21.0 |  |  | 67.5 |  |
| 24.0 |  |  | 73.8 |  |
TABLE (11.0.1)
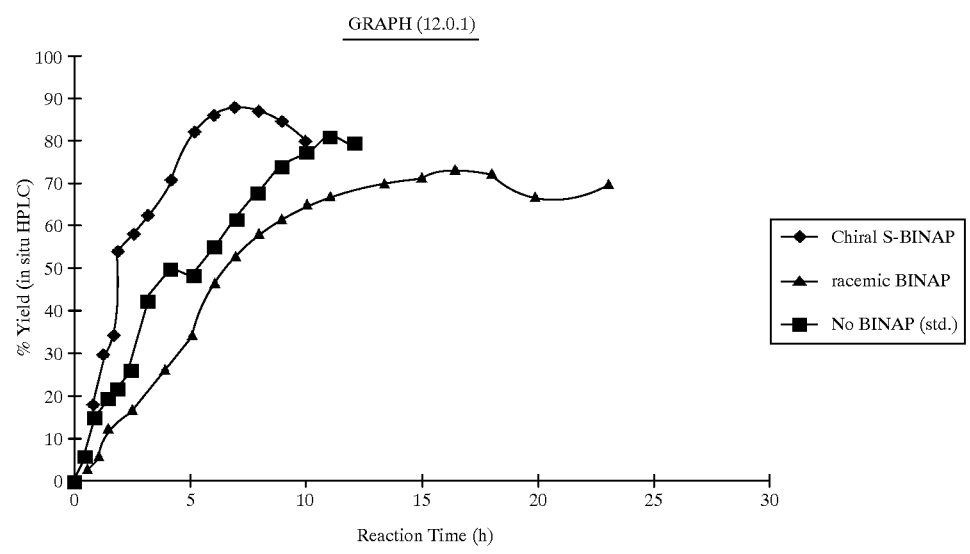
GRAPH (12.0.1)

TABLE (11.0.2)

| Time (hr) | Chiral (S)-BINAP | Racemic BINAP | No BINAP |
|---|---|---|---|
| 0 | 0.2 | 0.7 | 0.04 |
| 0.5 | 5 | 6.6 | 3.3 |
| 1 | 17.5 | 14.4 | 7.0 |
| 1.5 | 32.3 | 20.5 | |
| 2.0 | 37 | 25.8 | 17.7 |
| 2.5 | 51.4 | 28.0 | |
| 3.0 | 56.8 | 33.4 | 21.9 |
| 3.5 | 62.4 | 45.2 | |
| 4.0 | 69.8 | 52.5 | 31.9 |
| 5.0 | 77.3 | 51.5 | 41.2 |
| 6.0 | 82.4 | 58.7 | 45.4 |
| 7.0 | 85.9 | 64.7 | 52.4 |
| 8.0 | 85.7 | 70.6 | 57.1 |
| 9.0 | 83.8 | 76.8 | 63.1 |
| 10.0 | 80.9 | 77.7 | 67.4 |
| 11.0 | | 82.0 | 68.2 |
| 12.0 | | 81.2 | |
| 13.0 | | | 71.7 |
| 15.0 | | | 73.8 |
| 17.0 | | | 75.2 |
| 19.0 | | | 73.2 |
| 21.0 | | | 67.5 |
| 24.0 | | | 73.8 |

The observations made in the course of carrying out the above-described reactions, which are modifications of the Migita reaction, suggest that the auxiliary ligands used in the preparation processes of the present invention and defined herein, have applicability to other palladium catalyzed reactions. It has been found, e.g., that racemic BINAP shows a significant yield increase compared to other phosphorus ligand systems currently available, and also a significant rate increase, when used in catalytic levels equal to 2% moles relative to the principal reactants involved. It is known in the art that in the case of reactions involving oxygen and nitrogen nucleophiles, ligands such as BINAP and DPPF, 1,1'-bis(diphenylphosphino)-ferrocene, enhance the yield and rate of those reactions. This result has been attributed to a modest "bite-angle" possessed by the ligands that form the intermediate complexes involved in the catalytic cycle, which in turn leads to favorable reductive elimination. DPPF exhibited no such favorable impact, however, on the yields and rates of the preparation processes of the present invention. It has been surmised, therefore, that although the "bite-angle" of ligands in general remains important depending upon the specific stereochemical parameters involved, that it is not a critical feature of the auxiliary ligand being used in the preparation processes of the present invention.

It has also been discovered that, surprisingly, an enhanced reaction rate and yield are obtained from the reactions of SYNTHESIS SCHEMES (10.0.1) and (10.5.0) when particular stereoisomer forms of the auxiliary ligands of the present invention are used instead of the racemic form. For example, when (R)-BINAP or (S)-BINAP are used individually instead of racemic BINAP, (rac)-BINAP, in equivalent concentrations, still further improved results are obtained. For example, the reaction of SYNTHESIS SCHEME (10.0.1) is optimally completed in 22 to 24 hours when no auxiliary ligand is used, as compared with completion in 8 to 10 hours when (rac)-BINAP is used. Yet, when (R)- or (S)-BINAP are used, the required completion time is reduced to from 5 to 6 hours. Similar results have been obtained with regard to the reaction of SYNTHESIS SCHEME (10.5.0).

The use of optically active, i.e., stereoisomeric forms of the auxiliary ligands of the present invention, e.g., (R)- or (S)-BINAP auxiliary ligand, afford a further unexpected process advantage in the preparation processes of the present invention, which is the suppression of undesired side reactions. For example, it has been found that when the reaction of SYNTHESIS SCHEME (10.0.1) is carried out, the main product of the reaction, the fluoro-amide of Formula (2.0.0), undergoes further conversion to the corresponding fluoro-carboxylic acid of Formula (2.2.0), as shown in the following SYNTHESIS SCHEME (10.6.0):

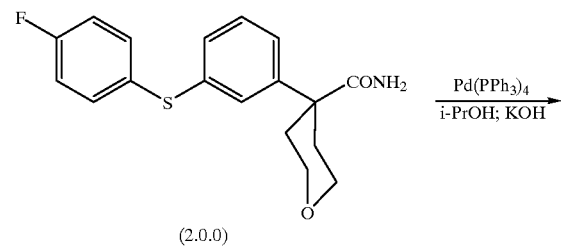

(2.0.0)

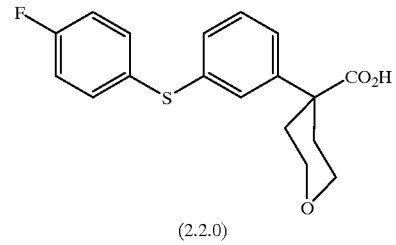

(2.2.0)

Where no auxiliary ligand is used in one of the above-described preparation processes, the typical reaction profile exhibits production of several side products, including the acid of Formula (2.2.0). After about 6 hours into the reaction, noticeable amounts of the acid of Formula (2.2.0) are being formed, and this increases to about 10% of yield after 24 hours of exposure to the homogeneous catalytic reaction conditions. By contrast, it has been found, surprisingly, that when the auxiliary catalysts as herein defined are used in the preparation processes of the present invention, the side reaction which produces the carboxylic compound of Formula (2.2.0) is effectively suppressed, so that significantly more of the original starting materials are converted to the desired end product of Formula (2.0.0).

These results are illustrated by the data in the following GRAPH (12.0.2) and GRAPH (12.0.3) and their corresponding TABLE (11.0.3) and TABLE (11.0.4):
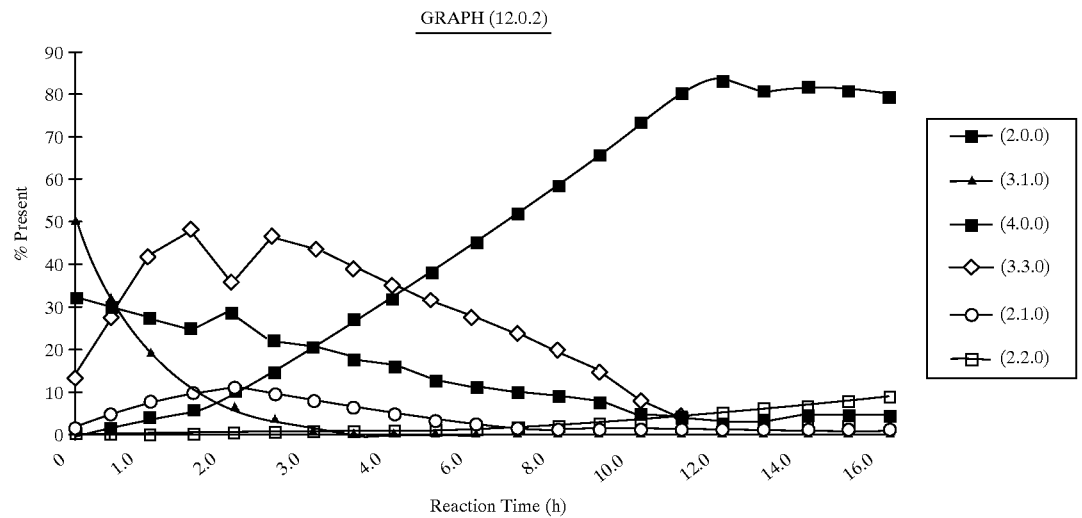
TABLE (11.0.3)
| Time (hr) | (2.0.0) | (3.1.0) | (4.0.0) | (3.3.0) | (2.1.0) | (2.2.0) |
|---|---|---|---|---|---|---|
| 0 | 13.5 | 32.3 | 51.1 | 0.2 | 0 | 1 |
| 0.5 | 29.7 | 30.5 | 32.7 | 1.4 | 0 | 4.3 |
| 1.0 | 40.4 | 28.3 | 19.1 | 3.4 | 0 | 7.4 |
| 1.5 | 45.8 | 25.8 | 10.1 | 6.6 | 0 | 8.8 |
| 2.0 | 37.1 | 29 | 6.3 | 11.9 | 0.13 | 11.8 |
| 2.5 | 44.4 | 21.8 | 2.1 | 15.2 | 0.2 | 10 |
| 3.0 | 41.1 | 20.9 | 0.7 | 21.5 | 0.3 | 9.2 |
| 3.5 | 39.0 | 18.9 | 0.3 | 27.9 | 0.6 | 7.1 |
| 4.0 | 35.5 | 18.2 | 0.1 | 34.3 | 0.9 | 5.6 |
| 5.0 | 31 | 15.2 | 0.1 | 41.6 | 1.5 | 3.1 |
| 6.0 | 27.6 | 14.5 | 0.1 | 48.4 | 2.4 | 2.1 |
| 7.0 | 23.0 | 12.5 | 0.1 | 53.8 | 3 | 1.4 |
| 8.0 | 18.8 | 11 | 0.09 | 59.8 | 3.8 | 1 |
| 9.0 | 13.8 | 9.0 | 0.08 | 66 | 4.6 | 0.8 |
| 10.0 | 8.5 | 6.5 | 0.03 | 69.9 | 4.7 | 0.7 |
| 11.0 | 4.8 | 6.2 | 0.02 | 76 | 6.2 | 0.7 |
| 12.0 | 2 | 5.2 | 0.02 | 78.2 | 6.9 | 0.6 |
| 13.0 | 1.3 | 4.7 | 0.02 | 77.1 | 7.3 | 0.6 |
| 14.0 | 0.9 | 4.9 | 0.02 | 77.5 | 8.7 | 0.6 |
| 15.0 | 0.6 | 5.2 | 0.01 | 76.6 | 9.6 | 0.6 |
| 16.0 | 0.5 | 5.5 | 0.02 | 76.2 | 10.3 | 0.7 |

GRAPH (12.0.3)

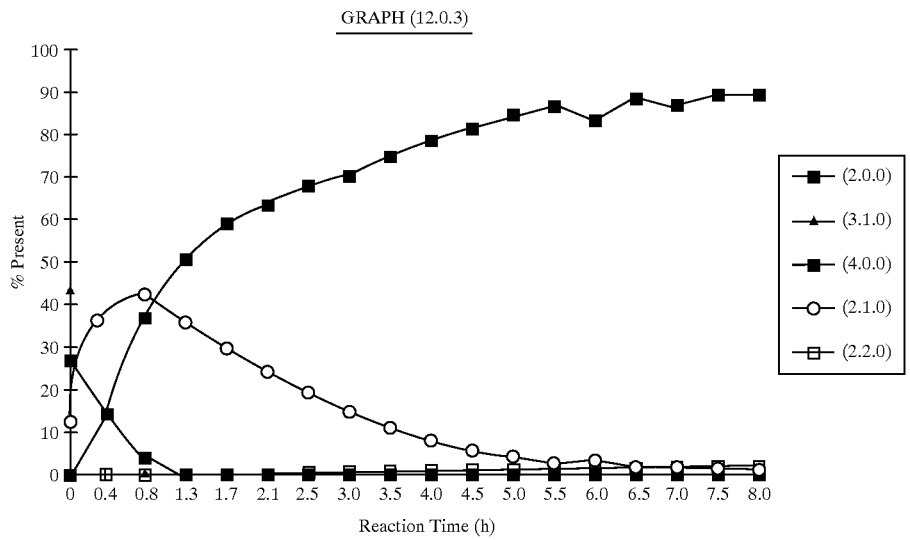

TABLE (11.0.4)

| Time (hr) | (4.0.0) | (3.1.0) | (2.0.0) | (2.2.0) | (2.1.0) |
|---|---|---|---|---|---|
| 0 | 27.2 | 44.5 | 1.2 | 0 | 14.1 |
| 0.4 | 14.7 | 13.9 | 12.3 | 0 | 40 |
| 0.8 | 4.6 | 1 | 34.8 | 0.2 | 46 |
| 1.3 | 1.4 | 0.07 | 51.6 | 0.4 | 38.2 |
| 1.7 | 0.4 | 0.05 | 61.5 | 0.7 | 32.5 |
| 2.1 | 0.09 | 0.04 | 68.4 | 1.0 | 26.4 |
| 2.5 | ND | 0.03 | 72.7 | 1.0 | 22.1 |
| 3.0 | ND | 0.02 | 75.7 | 1.3 | 18.7 |
| 3.5 | ND | 0.02 | 80.4 | 1.4 | 13.8 |
| 4.0 | ND | 0.02 | 83.2 | 1.6 | 10.6 |
| 4.5 | ND | 0.01 | 86.0 | 1.6 | 8.0 |
| 5.0 | ND | 0.02 | 87.4 | 1.8 | 6.2 |
| 5.5 | ND | 0.02 | 88.6 | 1.9 | 4.8 |
| 6.0 | ND | 0.02 | 85.9 | 2.9 | 5.4 |
| 6.5 | ND | 0.01 | 90 | 2.2 | 2.8 |
| 7.0 | ND | 0.01 | 88.8 | 3.0 | 2.6 |
| 7.5 | ND | 0.007 | 90.4 | 2.5 | 1.7 |
| 8.0 | ND | 0.007 | 90.7 | 2.9 | 1.6 |

After the reaction of SYNTHESIS SCHEME (10.0.1) is carried to completion, water is added to the reaction mixture to bring about precipitation and subsequent crystallization of the coupling product of Formula (2.0.0). The reaction work up conditions are basic, so that any residual carboxylic acid formed during the reaction is completely eliminated prior to product isolation. Consequently, the carboxylic acid purge is a feature of the process of the present invention which is especially useful, since it effectively removes from the isolated intermediate of Formula (2.0.0) any contamination by the carboxylic acid compound of Formula (2.2.0). This is a result of the fact that the carboxylic acid compound remains completely solubilized in the aqueous quench liquors in the form of carboxylate anion. This useful result is obtained even where the amounts of carboxylic acid compound contamination are as high as 10% of the reaction yield. Isolation of pure intermediate of Formula (2.0.0) is thus readily achieved.

It has further been discovered that a reaction path is favored in those cases where an auxiliary ligand as defined herein is used in the reaction, which is different from the reaction path that will occur when no auxiliary ligand is used. Thus, it has been found that when a catalytic quantity of (S)-BINAP is present, the reaction proceeds primarily by way of the fluoro-nitrile intermediate of Formula (2.1.0):

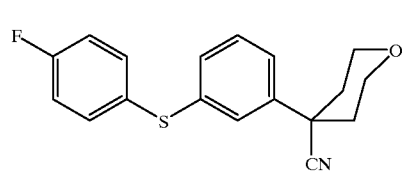

(2.1.0)

This nitrile intermediate is subsequently hydrolyzed to yield the desired product of Formula (2.0.0). However, when no auxiliary ligand as defined herein is present during the reaction, a significant quantity of the bromo-nitrile starting material of Formula (3.1.0) is hydrolyzed to the bromo-amide of Formula (3.3.0):

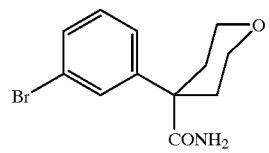

(3.3.0)

before coupling with the thiolate anion can occur. The bromo-amide of Formula (3.3.0) once formed undergoes palladium catalyzed coupling with the thiolate anion to yield the desired product of Formula (2.0.0). The chemical reactions discussed in this connection are summarized in the following SYNTHESIS SCHEME (10.7.0):

SYNTHESIS SCHEME (10.7.0)

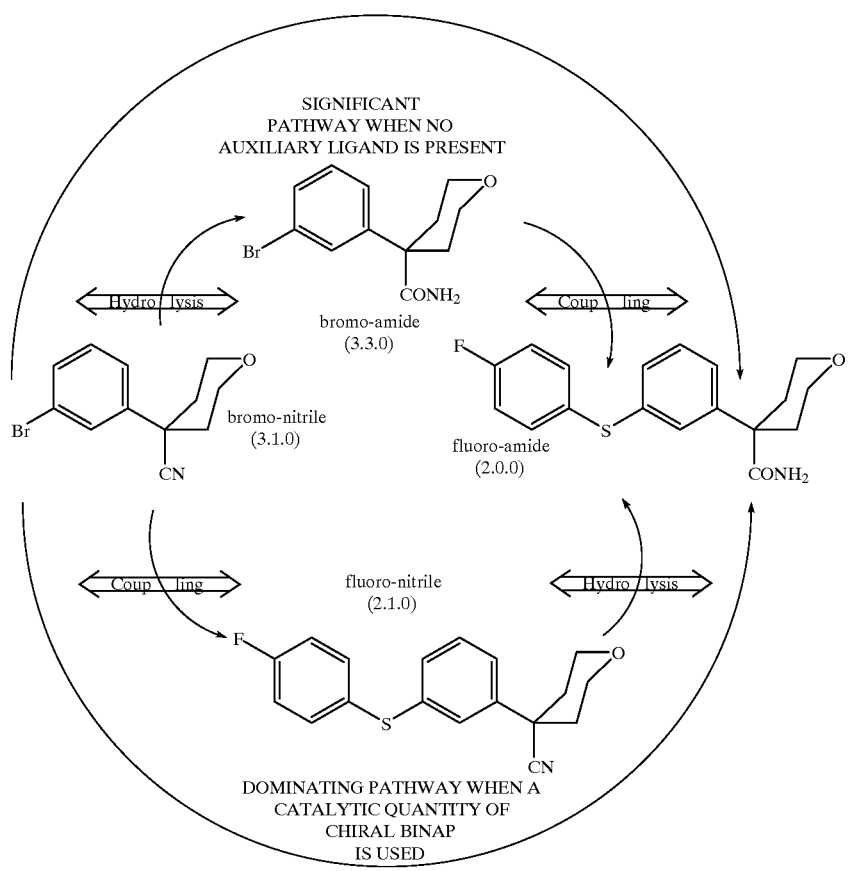

An increase in reaction rate and yield has been observed with the preparation processes of the present invention when catalytic quantities of racemic mixtures of the auxiliary ligands defined herein, e.g., (rac)-BINAP, are replaced with the corresponding enantiomerically pure (R)- or (S)- forms of those auxiliary ligands, e.g., (R)- or (S)-BINAP. It is surmised that these improvements cannot be explained by the previously discussed 'bite angle' in the reactive complex intermediate of the Hartwig type, which in this case would be (ArS) (Ar') Pd (BINAP). The Hartwig complex formed prior to reductive elimination contains only one BINAP ligand as does the elimination product Pd(BINAP), so the rate would in that case be identical for either enantiomer.

There is no intention herein to limit the scope of the present invention by setting forth details of proposed mechanisms of action which might explain the unexpected increases in reaction rates and yield which have been obtained with the preparation processes of the present invention. Such explanations must, in any event, remain hypothetical in nature. The discussion which is provided here is for the purpose of guiding the artisan in carrying out the processes of the present invention and adapting them to some particular purpose which that artisan might have.

The yield and rate amplification phenomenon arising from the catalytic cycle for bidentate phosphorus ligands which has been discovered with regard to the processes of the present invention may be illustrated in SYNTHESIS SCHEME (10.8.0):

SYNTHESIS SCHEME (10.8.0)

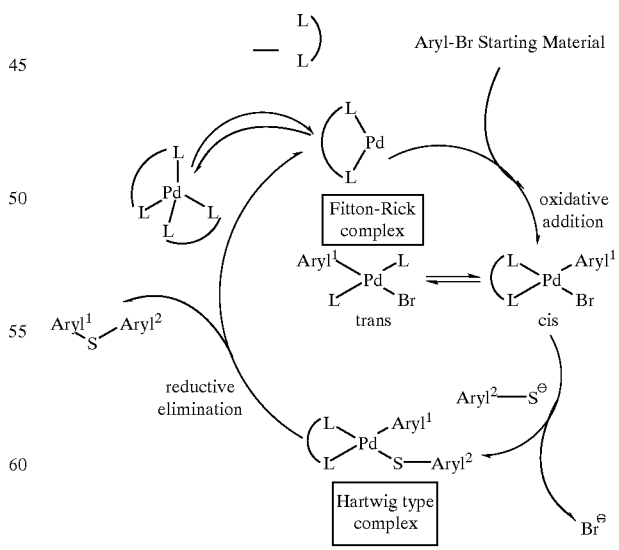

It is theorized that the improved results which have been obtained with the present invention can be explained if the concentration of the coordinately unsaturated 14 electron reactive species comprising palladium and a single bidentate auxiliary ligand as defined herein, e.g., Pd[BINAP], is sustained by an equilibrium between it and a species comprisng palladium and two bidentate auxiliary ligands, e.g., Pd[BINAP]$_2$. In this especially preferred case, the enantiomeric isomers of the palladium complex are Pd[(S)-BINAP]$_2$ and Pd[(R)-BINAP]$_2$. The equilibrium between Pd[(S)-BINAP] and Pd[(R)-BINAP] will have an equilibrium constant $K_S$ and $K_R$, respectively. $K_S$ and $K_R$ are equal in magnitude because the equilibria have symmetry as enantiomeric pairs. However, the equilibrium between Pd[(S)-BINAP][(R)-BINAP] and Pd[(S)-BINAP] or Pd[(R)-BINAP] will have a different equilibrium constant $K_{rac}$ because this palladium complex is diastereoisomeric. In accordance with the present invention it has been shown that $K_S = K_R \gg K_{rac} \gg K_M$ for the following reaction equilibria:

| Fast chiral BINAP channel | (S)-BINAP<br>(S)-BINAP | } Pd | $\xrightleftharpoons{K_S}$ | (S)-BINAP + (S)-BINAP |
| --- | --- | --- | --- | --- |
| | (R)-BINAP<br>(R)-BINAP | } Pd | $\xrightleftharpoons{K_R}$ | (R)-BINAP + (R)-BINAP |
| Intermediate rate, racemic BINAP channel | (S)-BINAP<br>(R)-BINAP | } Pd | $\xrightleftharpoons{K_{rac}}$ | (S)-BINAP + (R)-BINAP |
| | (R)-BINAP<br>(S)-BINAP | } Pd | $\xrightleftharpoons{K_{rac}}$ | (R)-BINAP + (S)-BINAP |
| Slow Migita channel | [(PPh$_3$)$_4$]—Pd | | $\xrightleftharpoons{K_M}$ | [(PPh$_3$)$_2$]—Pd + 2 PPh$_3$ |

The most preferred auxiliary ligand for use in the preparation methods of the present invention is (S)-(—)-2,2'-Bis(diphenylphosphino)-1,1'-binaphthyl, which may be illustrated by Formula (5.7.10):

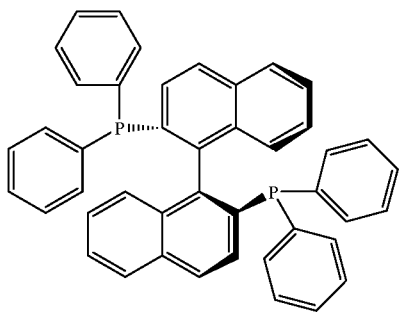

(5.7.10)

Accordingly, the most preferred auxiliary ligand of Formula (5.7.10) would be used with the most preferred palladium metal catalyst, tetrakis(triphenylphosphine)palladium (0), [(C$_6$H$_5$)$_3$P]$_4$Pd(0). Such a preferred palladium catalyst and auxiliary ligand as herein defined will usually be used without the need for the addition of any further ligand. Occasionally, however, a further ligand may be employed in addition to the auxiliary ligand, and this comprises an additional embodiment of the present invention. When such a further ligand is used with the palladium metal complex, e.g., [(C$_6$H$_5$)$_3$P]$_4$Pd(0), such ligands are preferably triphenylphosphine (TPP), ethylenebis(diphenylphosphine), or tri-(2-tolyl)phosphine.

The preferred ratio of catalyst to ligand, whether it is an auxiliary ligand as herein defined, or a further ligand being employed, is approximately 1:2 molar equivalents, but the artisan will be aware that the use of excessive amounts of ligand can lead to a reduction in the overall yield of the reaction in which such a ligand is being used. In the same manner, the other palladium metal complexes used as catalysts in the processes of the present invention are used with an auxiliary ligand as herein defined, and optionally with a further ligand. The dramatic impact on reaction rates and yields which the use of such auxiliary ligands has on the preparation processes of the present invention has already been described in detail further above.

The use of a further ligand, i.e., in addition to the auxiliary ligand as herein defined, would be expected to improve the yield of final product, i e., the compound of Formula (2.0.0). Such results are illustrated by the table of values immediately following showing yields from the above-described process of the present invention where different palladium metal complexes are used without a ligand or with one of a variety of ligands.

TABLE (11.0.3)

| Ref. No. | Palladium Metal Complex | Ligand | Yield of (2.0.0) | |
| --- | --- | --- | --- | --- |
| | | | In-situ | Isolated |
| 1 | trans-dichloro-bis(triphenyl-phosphine) palladium (II) | None | 57.2% | 43.4% |
| 2 | trans-dichloro-bis(triphenyl-phosphine) palladium (II) | Ethylenebis (diphenyl phosphine) | 72.2% | 71.3% |
| 3 | trans-dichloro-bis(triphenyl-phosphine) palladium (II) | Triphenyl-phosphine | 64.2% | 60.9% |
| 4 | trans-dichloro-bis(triphenyl-phosphine) palladium (II) | Tri-(2-tolyl) phosphine | 53.6% | 38.8% |
| 5 | tris(dibenzylideneacetone)-dipalladium(0) chloroform adduct. | None | 7.6% | 5.7% |
| 6 | tris(dibenzylideneacetone)-dipalladium(0) chloroform adduct. | Ethylenebis (diphenyl phosphine) | 34% | 18.3% |
| 7 | tris(dibenzylideneacetone)-dipalladium(0) chloroform adduct. | Triphenyl-phosphine | 75.1% | 69.8% |
| 8 | dichloro[1,1'-bis(diphenyl phosphino)ferrocene] palladium(II) dichloromethane adduct | None | 46.0% | 40.7% |
| 9 | dichloro[1,1'-bis(diphenyl phosphino)ferrocene] palladium(II) dichloromethane adduct | Ethylenebis (diphenyl phosphine) | 64.4% | 53.8% |
| 10 | dichloro[1,1'-bis(diphenyl phosphino)ferrocene] palladium(II) dichloromethane adduct | Triphenyl-phosphine | 64.4% | 55.0% |
| 11 | bis(dibenzylideneacetone) palladium(0). | None | 17.5% | 12.4% |
| 12 | bis(dibenzylideneacetone) palladium(0). | Ethylenebis (diphenyl phosphine) | 35.0% | 33.0% |
| 13 | bis(dibenzylideneacetone) palladium(0). | Triphenyl-phosphine | 55.9% | 39.0% |
| 14 | (π-allyl) palladium(II) chloride dimer | None | 14.2% | 8.3% |
| 15 | (π-allyl) palladium(II) chloride dimer | Ethylenebis (diphenyl phosphine) | 43.8% | 33.3% |
| 16 | (π-allyl) palladium(II) chloride dimer | Triphenyl-phosphine | 62.4% | 53.7% |
| 17 | tetrakis(triphenylphosphine palladium(0). CONTROL | None | 71.7% | 71.6% |

The above-described ligands as well as others well known in the art may be employed with the palladium metal complexes used as catalysts in the process of the present invention.

As pointed out further above, a particular advantage of the above-described process is that in the course of carrying out the reaction under the prescribed conditions, whether these are suitable or preferred, the nitrile moiety on the compound of Formula (3.0.0) is hydrolyzed to the corresponding carboxamide group which appears on the final product, a compound of Formula (1.0.0). Nevertheless, the present invention also affords an alternative process of preparing the novel intermediate, a compound of Formula (2.0.0), in which said nitrile moiety is first hydrolyzed to the corresponding carboxamide, thereby producing a compound of Formula (3.3.0). After this synthesis step has been carried out, the carboxamide compound of Formula (3.3.0) is reacted with the fluorothiophenol compound of Formula (4.0.0) to produce said novel intermediate of Formula (2.0.0).

It will be further noted that the second step of the above-mentioned alternative process is carried out in a fashion which is essentially the same as that illustrated in Scheme 2 above.

Consequently, the present invention is also concerned with an alternative process for preparing a compound of Formula (2.0.0):

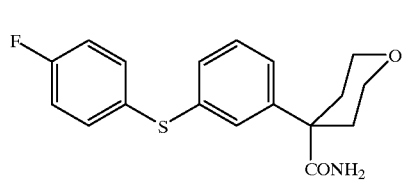

(2.0.0)

which may be illustrated by SYNTHESIS SCHEME (10.1.0) as follows:

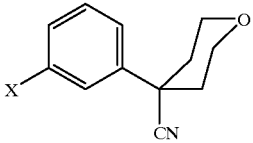

(3.0.0)

where X is bromo or iodo;

(2) in a solvent consisting of a straight or branched chain aliphatic alcohol having a total of from 2 to 7 carbon atoms, optionally as an aqueous mixture thereof, and more preferably where said alcohol is a secondary alcohol selected from the group consisting of isopropyl alcohol, sec-butyl alcohol, iso-pentyl alcohol, and 2-heptanol, optionally as an aqueous mixture of said secondary alcohol;

(3) in the presence of strong base of Formula (5.0.0):

$$M\text{-}O\text{-}R^5 \quad (5.0.0)$$

where

M is an alkali metal, Group 1/Ia element, selected from the group consisting of lithium, Li; sodium, Na; potassium, K; rubidium, Rb; and cesium, Cs; and $R^5$ is hydrogen, H; or straight or branched chain $(C_1$–$C_4)$ alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$;

SYNTHESIS SCHEME (10.1.0)

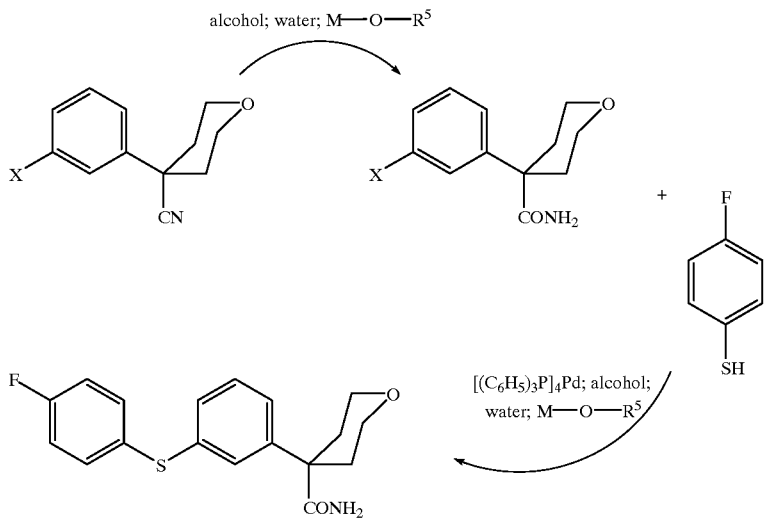

where X, M, and $R^5$ all have the same meaning as defined elsewhere herein.

The alternative process of the present invention illustrated in SYNTHESIS SCHEME (10.1.0) may be carried out by:

(a) establishing a reaction mixture consisting of (1) tetrahydro-4-(3-bromo- or iodo-phenyl)-2H-pyran-4-nitrile of Formula (3.0.0):

sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$; including mixtures of the above; followed by (b) heating said reaction mixture, preferably at reflux, preferably for a period of from 3 to 8 hours, more preferably from 5 to 6 hours; whereby there is produced a compound of Formula (3.2.0):

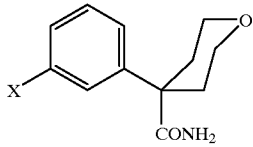

(3.2.0)

where X is bromo or iodo;

followed by (c) forming a reaction mixture consisting of said compound of Formula (4.0.0) and 4-fluorothiophenol of Formula (4.0.0):

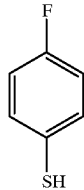

(4.0.0)

(1) in a solvent consisting of a straight or branched chain aliphatic alcohol having a total of from 2 to 7 carbon atoms, optionally as an aqueous mixture thereof, and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;

(2) in the presence of strong base of Formula (5.0.0):

M-O-R⁵            (5.0.0)

where

M is an alkali metal, Group 1/Ia element, selected from the group consisting of lithium, Li; sodium, Na; potassium, K; rubidium, Rb; and cesium, Cs; and R⁵ is hydrogen, H; or straight or branched chain (C₁–C₄) alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, LiOCH₃; sodium methoxide, NaOCH₃; potassium methoxide, KOCH₃; rubidium methoxide, RbOCH₃; cesium methoxide, CsOCH₃; lithium ethoxide, LiOCH₂CH₃; sodium ethoxide, NaOCH₂CH₃; potassium ethoxide, KOCH₂CH₃; rubidium ethoxide, RbOCH₂CH₃; cesium ethoxide, CsOCH₂CH₃; lithium tert-butoxide, LiOC(CH₃)₃; sodium tert-butoxide, NaOC(CH₃)₃; potassium tert-butoxide, KOC(CH₃)₃; rubidium tert-butoxide, RbOC(CH₃)₃; and cesium tert-butoxide, CsOC(CH₃)₃; including mixtures of the above;

and further (3) in the presence of a transition metal catalyst comprising a member independently selected from the group consisting of palladium metal complexes; preferably wherein said palladium metal complex is a member selected from the group consisting of tetrakis(triphenylphosphine)palladium(0), [(C₆H₅)₃P]₄Pd(0);

tetrakis(methyldiphenylphosphine)palladium(0), [(C₆H₅)₂PCH₃]₄Pd(0);

trans-dichlorobis(methyldiphenylphosphine)palladium(II), [(C₆H₅)₂PCH₃]₂PdCl₂;

dichlorobis[methylenebis(diphenylphosphine)]dipalladium-dichloromethane adduct;

dichlorobis(triphenylphosphine)palladium(II), [(C₆H₅)₃P]₂PdCl₂;

tris(dibenzylideneacetone)dipalladium(0)-chloroform adduct, (C₆H₅CH=CHCOCH=CHC₆H₅)₃Pd₂·CHCl₃;

bis(dibenzylideneacetone)palladium(0), (C₆H₅CH=CHCOCH=CHC₆H₅)₂Pd;

[1,1'-bis(diphenylphosphino)ferrocene]dichloropalladium(II), complex with dichloromethane bis[1,2-bis(diphenylphosphino)ethane]palladium(II); and (π-allyl)palladium(II) chloride dimer;

followed by (d) heating said reaction mixture, preferably at reflux, preferably for a period of from 5 to 15 hours, more preferably from 8 to 10 hours; whereby there is produced said compound of Formula (2.0.0).

One of the key aspects of the preparation processes of the present invention is an improved means of producing the known 5-lipoxygenase inhibitory compound of Formula (1.0.0):

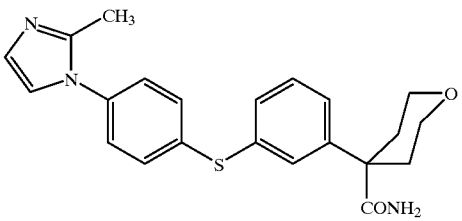

(1.0.0)

This improved process involves most of the above-described preferred embodiments of the present invention, and may be illustrated by SYNTHESIS SCHEME (10.3.0) as follows:

SYNTHESIS SCHEME (10.3.0)

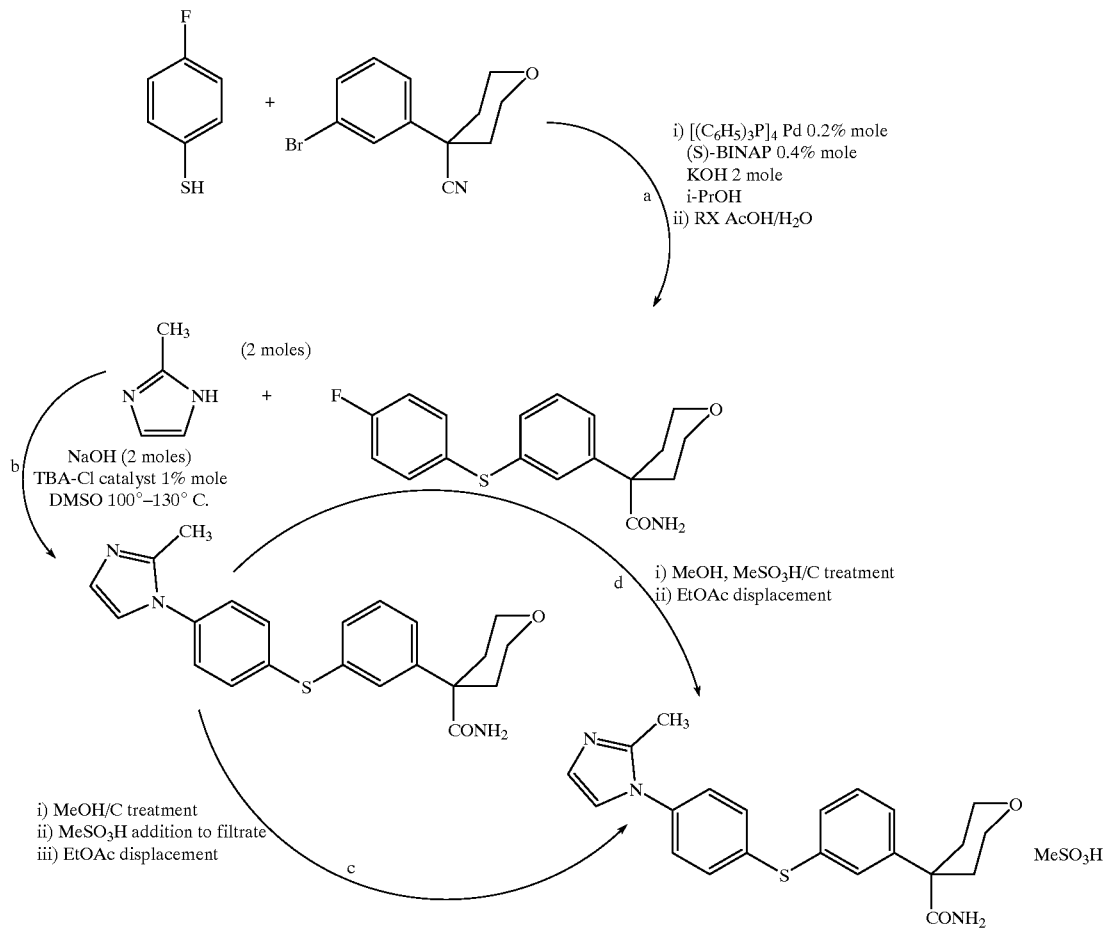

The improved process of the present invention illustrated in SYNTHESIS SCHEME (10.3.0) is deemed to comprise a total of six embodiments of the present invention. The first embodiment is Step a, which is the first step illustrated in SYNTHESIS SCHEME (10.3.0), and is a process for preparing the novel intermediate of the present invention of Formula (2.0.0). The second embodiment is Step b, which is the second or middle step illustrated in SYNTHESIS SCHEME (10.3.0), and is a process for preparing the known 5-lipoxygenase inhibitory compound of Formula (1.0.0), as the compound per se. The third embodiment is Step c or Step d, which is the last step in SYNTHESIS SCHEME (10.3.0), and is a process for preparing the mesylate salt of said known compound of Formula (1.0.0). The fourth embodiment is Step b+Step c or d. The fifth embodiment is Step a+Step b. The sixth embodiment is Step a+Step b+Step c or d.

For the sake of brevity, only the second and sixth embodiments are described in detail below. Accordingly, the second above-mentioned embodiment, Step b in SYNTHESIS SCHEME (10.3.1), is carried out as follows:

(a) establishing a reaction mixture consisting of (1) tetrahydro-4-[3-(4-fluorophenyl)thio]phenyl-2H-pyran-4-carboxamide of Formula (2.0.0):

and (2) 2-methylimidazole;

(3) in an aprotic solvent, preferably a member selected from the group consisting essentially of hexane; 1,4-dioxane; carbon tetrachloride; benzene; toluene; xylenes; diethyl ether; chloroform; ethyl acetate; tetrahydrofuran (THF); methylene chloride; hexamethylphosphoric triamide (HMPT); nitromethane; N,N-dimethylformamide (DMF); acetonitrile; sulfolane; and dimethylsulfoxide (DMSO); more preferably dimethylsulfoxide (DMSO);

(4) in the presence of a strong base in solid form selected from the group consisting of sodium hydroxide, NaOH; and potassium hydroxide, KOH;

and optionally (5) in the presence of a catalytic amount of cesium carbonate, $Cs_2CO_3$, or of a phase transfer catalyst, preferably a member selected from the group consisting of cetyltrimethylammonium bromide (CTMAB); dibenzo-18-crown-6 (DB-18-c-6); dicyclohexano-18-crown-6 (DB-18-c-6); 18-crown-6 (18-c-6); (—)-N-dodecyl-N-methylephedrinium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide (TBAI); tetra-ethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC); and more preferably a quaternary ammonium salt or a phosphonium salt comprising a member of the above-recited group;

followed by (b) heating said reaction mixture, preferably at reflux, preferably from 115° to 145° C., more preferably from 125° to 130° C., under a nitrogen atmosphere, preferably for from 12 to 30 hours, more preferably for from 17 to 24 hours; whereby there is produced said compound of Formula (1.3.0).

The above-mentioned sixth embodiment, Step a+Step b+Step c of SYNTHESIS SCHEME (10.3.0), of the present invention is a process for preparing a substantially pure mesylate salt of Formula (1.0.1):

(1.0.1)

comprising:

(a) preparing a compound of Formula (2.0.0):

(2.0.0)

comprising:

(1) establishing a reaction mixture consisting of
(i) tetrahydro-4-(3-bromo-phenyl)-2H-pyran-4-nitrile of Formula (3.1.0):

(3.1.0)

and (ii) 4-fluorothiophenol of Formula (4.0.0):

(4.0.0)

(iii) in a solvent selected from the group consisting of iso-propyl alcohol, sec-butyl alcohol, iso-pentyl alcohol, and 2-heptanol, optionally as an aqueous mixture thereof;

(iv) in the presence of a strong base selected from the group consisting of sodium hydroxide, NaOH; and potassium hydroxide, KOH;

and further (v) in the presence of a catalyst comprising a member independently selected from the group consisting of the following palladium metal complexes:

tetrakis(triphenylphosphine)palladium(0), [(C$_6$H$_5$)$_3$P]$_4$Pd(0);

tetrakis(methyldiphenylphosphine)palladium(0), [(C$_6$H$_5$)$_2$PCH$_3$]$_4$Pd(0);

trans-dichlorobis(methyldiphenylphosphine)palladium(II), [(C$_6$H$_5$)$_2$PCH$_3$]$_2$PdCl$_2$;

dichlorobis[methylenebis(diphenylphosphine)]dipalladium-dichloromethane adduct;

dichlorobis(triphenylphosphine)palladium(II), [(C$_6$H$_5$)$_3$P]$_2$PdCl$_2$;

tris(dibenzylideneacetone)dipalladium(0)-chloroform adduct, (C$_6$H$_5$CH=CHCOCH=CHC$_6$H$_5$)$_3$Pd$_2$·CHCl$_3$;

bis(dibenzylideneacetone)palladium(0), (C$_6$H$_5$CH=CHCOCH=CHC$_6$H$_5$)$_2$Pd;

[1,1'-bis(diphenylphosphino)ferrocene]dichloropalladium (II), complex with dichloromethane bis[1,2-bis(diphenylphosphino)ethane]palladium(II); and (π-allyl)palladium(II) chloride dimer;

followed by (2) heating said reaction mixture at reflux of from 80° to 84° C. for a period of from 18 to 30 hours, preferably 24 hours; whereby there is produced said compound of Formula (2.0.0);

(b) establishing a reaction mixture consisting of said compound of Formula (2.0.0) and a compound of Formula (1.3.10):

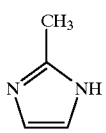

(1.3.10)

(1) in an aprotic solvent selected from the group consisting essentially of tetrahydrofuran (THF); methylene chloride; N,N-dimethylformamide (DMF); and dimethylsulfoxide (DMSO); more preferably dimethylsulfoxide (DMSO);

(2) in the presence of a strong base in solid form selected from the group consisting of sodium hydroxide, NAOH; and potassium hydroxide, KOH;

and optionally (3) in the presence of a catalytic amount of cesium carbonate, $Cs_2CO_3$, or of a phase transfer catalyst, preferably a member selected from the group consisting of cetyltrimethylammonium bromide (CTMAB); dibenzo-18-crown-6 (DB-18-c-6); dicyclohexano-18-crown-6 (DC-18-c-6); 18-crown-6 (18-c-6); (—)-N-odecyl-N-methylephedrinium bromide (DMCOH); hexamethyl phosphoric triamide (HMPT); cetylpyridinium bromide (NCPB); N-benzylquininium chloride (QUIBEC); tetra-n-butylammonium bromide (TBAB); tetra-n-butylammonium chloride (TBAC); tetra-n-butylammonium hydroxide (TBAH); tetra-n-butylammonium hydrogen sulfate (TBAHS); tetra-n-butylammonium iodide (TBAI); tetra-ethylammonium chloride hydrate (TEAC); tri-n-butylamine (TBA); benzyltributylammonium bromide (TBBAB); hexadecyltributylphosphonium bromide (TBHDPB); benzyltriethylammonium bromide (TEBAB); benzyltriethylammonium chloride (TEBA); hexadecyltriethylammonium chloride (TEHDAC); tetramethylammonium chloride (TMAC); hexadecyltrimethylammonium chloride (TMHDAC); and octyltrimethylammonium chloride (TMOAC); and more preferably a quaternary ammonium salt or a phosphonium salt comprising a member of the above-recited group;

followed by (c) heating said reaction mixture at reflux, under a nitrogen atmosphere; whereby there is produced a compound of Formula (1.0.0):

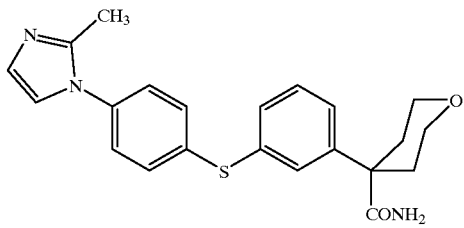

(1.0.0)

followed by (d) forming a concentrated methanol solution of said compound of Formula (1.0.0) followed by filtering of the solution, preferably through activated carbon, to the filtrate of which there is then added methanesulfonic acid, $MeSO_3H$; followed by further concentration and the addition of ethyl acetate ad seriatim until a crystalline product is isolated comprising substantially pure mesylate salt of Formula (1.0.1)

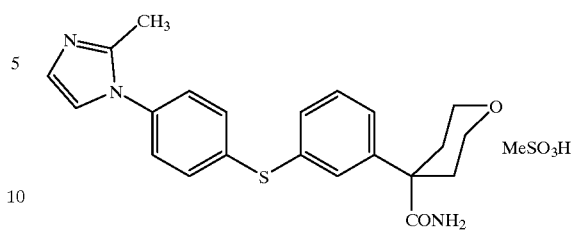

(1.0.1)

or, alternatively, followed by (e) forming a concentrated methanol solution of said compound of Formula (1.0.0) to which there is then added methanesulfonic acid, $MeSO_3H$; followed by filtering of the mixture, preferably through activated carbon, after which there follows further concentration and the addition of ethyl acetate ad seriatim until a crystalline product is isolated comprising substantially pure mesylate salt of Formula (1.0.1)

The preferred method of mesylate salt formation is that of forming a concentrated methanol solution of said compound of Formula (1.0.0) which also contains methanesulfonic acid, $MeSO_3H$; followed by filtration. It has been found that this method results in a significant reduction in process volumes and a reduction in the amount of residual palladium in the final product. The primary purpose of the above-described methanol recrystallization during formation of the mesylate salt of Formula (1.0.1) is to remove any residual palladium from the final product that may not have been removed during the filtration step, which is preferably carried out using activated carbon.

It will be appreciated that the above-described process for preparing the mesylate salt of the compound of Formula (1.0.0) may be readily adapted using the skills and knowledge available in the art, to prepare other, analogous sulfonate salts of the compound of Formula (1.0.0), especially the tosylate salt.

EXEMPLIFICATION OF PREFERRED EMBODIMENTS

The processes, novel intermediate, and novel final products of the present invention will be better appreciated by their illustration in working examples showing details for carrying them out. However, the examples of preferred embodiments of the present invention which follow are intended for purposes of demonstration only, and should not be taken as in any way limiting the scope of the present invention, for which purpose the claims appended hereto are set forth.

EXAMPLE 1

Synthesis of tetrahydro-4-(3-bromophenyl)-2H-pyran-4-nitrile

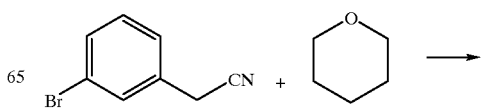

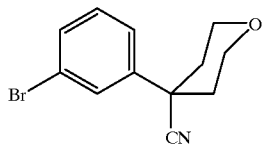

3-Bromophenylacetonitrile (20.0 g, 102 mmole, 1 eq.), commercially available from Aldrich Chemical Co., Milwaukee, Wis., tetrahydrofuran (120 ml), 40% aqueous sodium hydroxide solution (180 ml, mmole, eq.), tetrabutylammonium hydrogensulfate (3.46 g, mmole, 0.1 eq.) were stirred in a reaction flask set for boiling at reflux. Thereafter, 2,2'-dichlorodiethylether (13.75 ml, 117.3 mmole, 0.1 eq.) was added with stirring at room temperature, 20–25° C. The resultant reaction mixture was boiled at reflux for 5–8 h at approximately 64° C. The reaction mixture was cooled to ambient temperature and ethyl acetate (154 ml) was added. The lower aqueous layer was separated and the organic layer evaporated down into a red oil. Iso-propanol (100 ml) and water (10 ml) were added to the oil and stirred at 0° C. overnight to yield a crystal slurry. The crystal slurry was vacuum filtered, washed with isopropanol (2×20 ml). The white crystalline solid was dried under vacuum at 40–45° C. Yield 18.57 g (68.4%): mp 82–85° C.; m/z 267 (m+1); $^1$H NMR (300 MHz, DMSO) δ 7.75 (s, 1 H), 7.6 (m, 2 H), 7.44 (t, 1H), 4.02 (m, 2H), 3.66 (m, 2H), 2.14 (m, 4H).

EXAMPLE 2

Synthesis of tetrahydro-4-[3-(4-fluorophenyl)-thio]-phenyl-2H-pyran-4-carboxamide

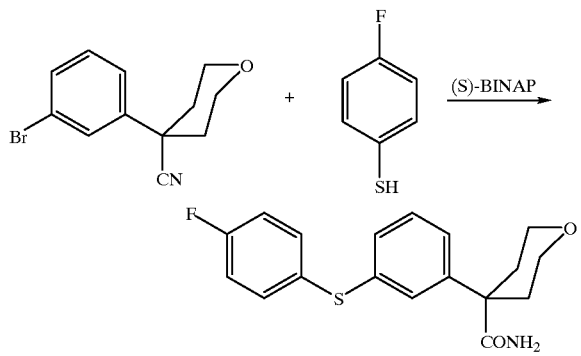

Propan-2-ol (120 ml); tetrahydro-4-(3-bromophenyl)-2H-pyran-4-nitrile (20.0 g, 75.15 mmole, 1 eq.); potassium hydroxide (9.76 g, 150.30 mmole, 2 eq.); (triphenylphosphine)palladium(0) (174 mg, 0.150 mmole, 0.002 eq.); (S)-(—)-2,2'-bis(diphenylphosphino)-1,1'-binaphthyl [(S)-BINAP, 187 mg, 0.301 mmole, 0.004 eq.]; and 4-fluorothiophenol (8.0 ml, 75.15 mmole, 1 eq.) were added to a reaction flask set for boiling at reflux under a nitrogen atmosphere. The resultant reaction mixture was boiled at reflux for 20–24 h at approximately 82° C. The reaction mixture was cooled to ambient temperature, 20–25° C., and water (120 ml) was added to obtain a slurry which was stirred for an additional 2 hours. The crude product was isolated by filtration and the wet cake was transferred to a flask to which acetic acid (160 ml, 8 vol) was added. The solution was heated to 100° C. with stirring, and was then vacuum filtered while hot and washed with acetic acid (40 ml). The yellow filtrate was heated to 75° C. after which water (120 ml) was added over a 15 minute period. A white precipitate formed and the reaction mixture was allowed to cool to room temperature and stirred. The reaction mixture was vacuum filtered and the filtrate washed twice with water (20 ml). The product was dried in a vacuum oven to give a white solid: yield 21.04 g (84.5%). The HPLC isolated yield was 97.1%. The structure of the final product was confirmed by $^1$H NMR and the concentration of palladium in the final product was determined to be 88 ppm.

EXAMPLE 3

Synthesis of tetrahydro-4-[3-(4-fluorophenyl)-thio]-phenyl-2H-pyran-4carboxamide

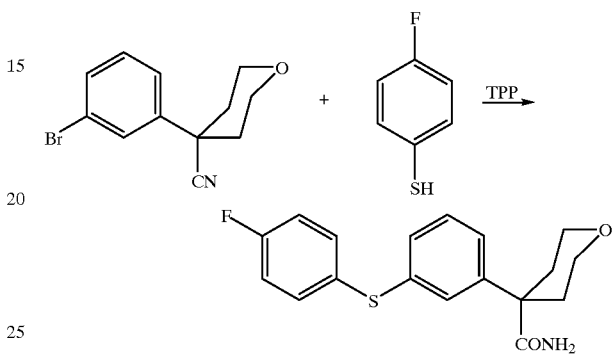

Propan-2-ol (150 ml, 6 vol.); tetrahydro-4-(3-bromophenyl)-2H-pyran-4-nitrile (24.98 g, 93.9 mmole, 1 eq.); potassium hydroxide (12.12 g, 188 mmole, 2 eq.); water (1.93 g, 188 mmole, 2 eq.); tetrakis(triphenylphosphine)palladium(0) (1.085 g, 0.939 mmole, 0.01 eq.); triphenylphosphine (TPP: 0.493 g, 1.88 mmole, 0.02 eq.); and 4-fluorothiophenol (12.03 g, 93.9 mmole, 1 eq.) were added to a reaction flask set for boiling at reflux under a nitrogen atmosphere. The resultant reaction mixture was boiled at reflux for 20–24 h at approximately 84° C. The reaction mixture was cooled to 70° C., and water (150 ml) was added, after which the reaction mixture was further cooled to room temperature, granulated for 1 hour and filtered. The resulting tan filter cake was washed with an iso-propanol/water solution (60 ml each). The filter cake was then transferred to a reaction flask to which acetic acid (200 ml), Darco KB-B brand activated carbon filter aid (1.25 g), and Celite brand silica filter aid (2.5 g) were added. The reaction flask was warmed to 100° C. and then cooled to 75–80° C., after which its contents were vacuum filtered and rinsed with acetic acid (30 ml)

The solubility of the product of this reaction was separately determined to be about 62 mg/ml in acetic acid at room temperature, and to be about 4.5 mg/ml in a 2:1 mixture of acetic acid and water. The reaction flask was heated to 75° C., after which water (150 ml) was added over a period of 15 minutes, at the end of which crystals were observed to form. The reaction mixture was cooled to 22° C. and granulated for 1 hour. The resulting slurry was then vacuum filtered and the filter cake was washed twice with water (100 ml). The filter cake (75 g) was placed in a 50° C. vacuum drier with a nitrogen bleed, after which 23.04 g of solid product were obtained for a yield of 74.0%. HPLC analysis of the Darco cake indicated that 0.263 g of product were retained.

EXAMPLE 4

Synthesis of tetrahydro-4-{3-[4-(2-methyl-1H-imidazol-1-yl)-phenyl]-thio}-phenyl-2H-pyran-4-carboxamide, Using Powdered NaOH and tert-Butylammonium Chloride

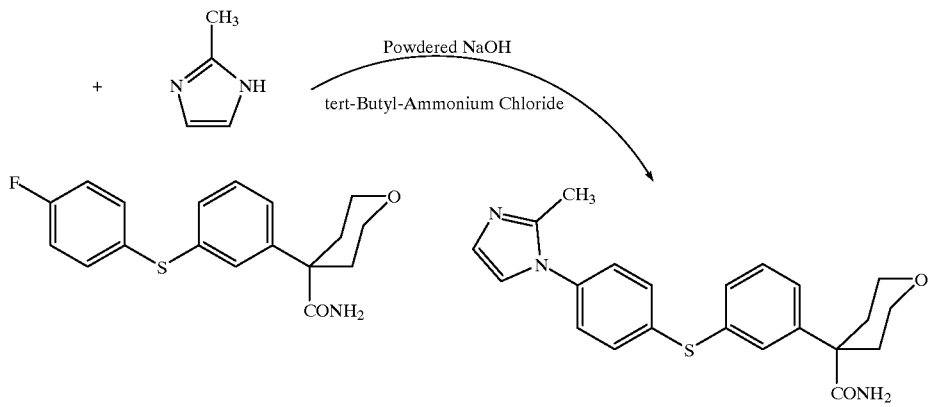

Tetrahydro-4-[3-(4-fluorophenyl)-thio]-phenyl-2H-pyran-4-carboxamide (5.0 g, 15.09 mmole, 1 eq), dimethylsulfoxide (50 ml, 10 vol), 2-methylimidazole (2.48 g, 30.17 mmole, 2.0 eq), powdered sodium hydroxide (1.207 g, 30.17 mmole, 2.0 eq), and tert-butylammonium chloride (210 mg, 0.754 mmole, 0.05 eq) were added to a reaction flask set for boiling at reflux under a nitrogen atmosphere, and the reaction mixture was heated at 130° C. for 6 hours under nitrogen. The reaction mixture was then allowed to cool to room temperature and quenched with water (50 ml), which resulted in the formation of a precipitate. An exotherm of 10–15° C. was observed during the water addition. The product was isolated by vacuum filtration and washed with water (50 ml). The product was dried overnight in a vacuum oven at 40–45° C. The amount of product obtained was 5.46 g, which represented a 88% yield. The structure of the product was confirmed using analytical data.

EXAMPLE 5

Synthesis of tetrahydro-4-{3-[4-(2-methyl-1H-imidazol-1-yl)-phenyl]-thio}-phenyl-2H-pyran-4-carboxamide, Using Powdered NaOH and Tetra-(n-Butyl)-Ammonium Chloride Tetrahydro-4-[3-(4-fluorophenyl)-thio]-phenyl-2H-pyran-4-carboxamide (5.0 g, 15.09 mmole, 1 eq), dimethylsulfoxide (50 ml, 10 vol), 2-methylimidazole (2.48 g, 30.17 mmole, 2.0 eq), powdered sodium hydroxide (1.207 g, 30.17 mmole, 2.0 eq), and tetra(n-butyl)-ammonium chloride (210 mg, 0.754 mmole, 0.05 eq) were added to a reaction flask set for boiling at reflux under a nitrogen atmosphere, and the reaction mixture was heated at 100° C. for 28 hours under nitrogen. The reaction mixture was then allowed to cool to room temperature and quenched with water (50 ml), which resulted in the formation of a precipitate. An exotherm of 20–25° C. was observed during the water addition. The product was isolated by vacuum filtration and dried overnight in a vacuum oven. The amount of product obtained was 5.54 g, which represented a 88.6% yield. The structure of the product was confirmed using analytical data.

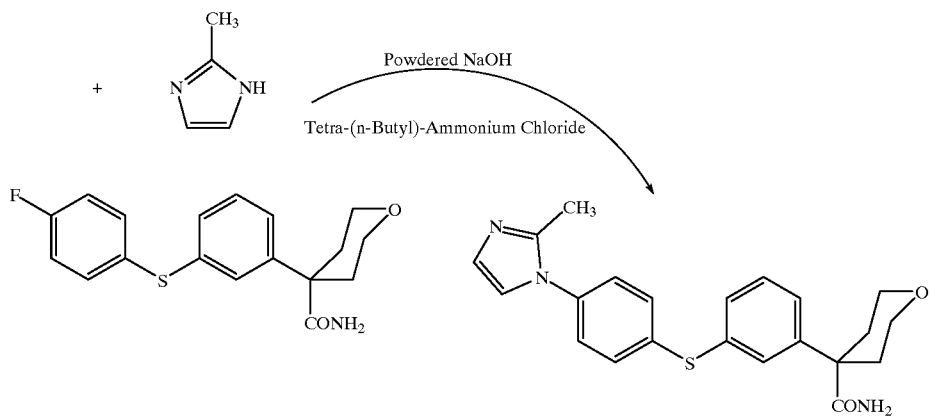

EXAMPLE 6

Synthesis of tetrahydro-4-{3-[4-(2-methyl-1H-imidazol-1-yl)-phenyl]-thio}-phenyl-2H-pyran-4-carboxamide, Using Solid NaOH and Cs₂CO₃

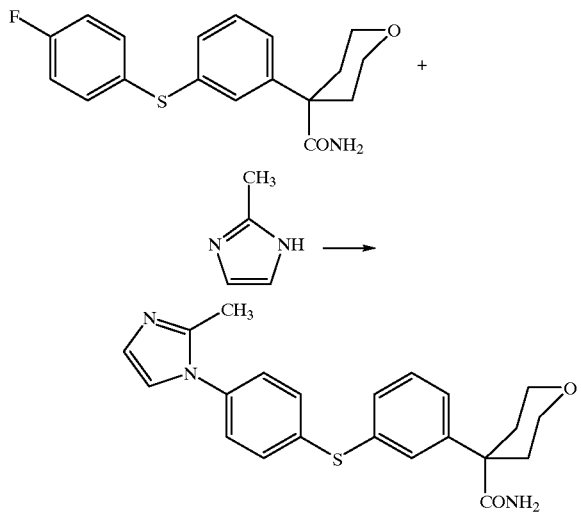

Tetrahydro-4-[3-(4-fluorophenyl)-thio]-phenyl-2H-pyran-4-carboxamide (25.0 g, 75.4 mmole, 1 eq), dimethylsulfoxide (250 ml, 10 vol), 2-methylimidazole (12.39 g, 150.9 mmole, 2.0 eq), sodium hydroxide (6.03 g, 150.9 mmole, 2.0 eq), and cesium carbonate (1.23 g, 0.38 mmole, 0.005 eq) were added to a reaction flask set for boiling at reflux under a nitrogen atmosphere, and the reaction mixture was heated at 125–130° C. for 17–24 hours under nitrogen. After the reaction was completed, it was cooled (<30° C.) and quenched with water (250 ml, 10 vol), which resulted in the formation of a precipitate. An exotherm of 10–15° C. was observed during the water addition. The reaction slurry thus formed was cooled to room temperature (15–25° C.) and then granulated for 1 hour. The product was isolated by vacuum filtration and washed with water (140 ml, 5.6 vol). The product was dried overnight in a vacuum oven at 40–45° C. The amount of product obtained was 29.4 g, which represented a 99% yield. The analytical data for the product were as follows: mp 198–200° C.; m/z 396 (m+1); $^1$H NMR (300 MHz, DMSO) δ 7.41 (m, 10H), 7.12 (s, 1H), 6.93 (d, 1H), 3.75 (m, 2H), 3.48 (t, 2H), 2.48 (d, 2H), 2.3 (s, 3H), 1.75 (m, 2H); IR (drifts) $v_{max}$ 3402, 3301, 3123, 3096, 2971, 2930, 2880, 1680, 1663, 1622, 1593, 1569, 1528.

EXAMPLE 7

Synthesis of tetrahydro-4-{3-[4-(2-methyl-1H-imidazol-1-yl)-phenyl]-thio}-phenyl-2H-pyran-4-carboxamide, Using Solid NaOH and a Phase Transfer Catalyst

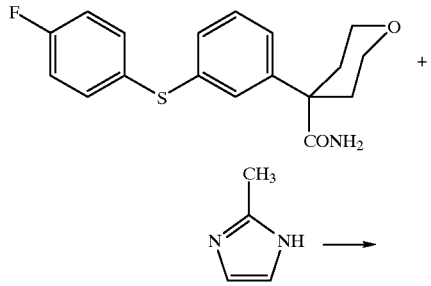

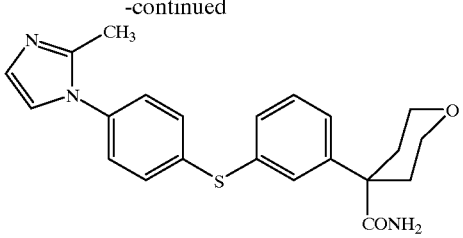

Tetrahydro-4-[3-(4-fluorophenyl)-thio]-phenyl-2H-pyran4-carboxamide (25.0 g, 75.4 mmole, 1 eq), dimethylsulfoxide (250 ml, 10 vol), 2-methylimidazole (12.39 g, 150.9 mmole, 2.0 eq), sodium hydroxide (6.03 g, 150.9 mmole, 2.0 eq), and tetra-n-butylammonium chloride (TBAC) (0.210 g, 0.75 mmole, 0.05 eq), were added to a reaction flask set for boiling at reflux under a nitrogen atmosphere, and the reaction mixture was heated at 125–130° C. for 17–24 hours under nitrogen. After the reaction was completed, it was cooled (<30° C.) and quenched with water (250 ml, 10 vol), which resulted in the formation of a precipitate. An exotherm of 10–15° C. was observed during the water addition. The reaction slurry thus formed was cooled to room temperature (15–25° C.) and then granulated for 1 hour. The product was isolated by vacuum filtration and washed with water (140 ml, 5.6 vol). The product was dried overnight in a vacuum oven at 40–45° C. The amount of product obtained was 27.6 g, which represented a 93.0% yield. The analytical data for the product were as follows: mp 198–200° C.; m/z 396 (m+1); $^1$H NMR (300 MHz, DMSO) δ 7.41 (m, 10H), 7.12 (s, 1H), 6.93 (d, 1H), 3.75 (m, 2H), 3.48 (t, 2H), 2.48 (d, 2H), 2.3 (s, 3H), 1.75 (m, 2H); IR (drifts) $v_{max}$ 3402, 3301, 3123, 3096, 2971, 2930, 2880, 1680, 1663, 1622, 1593, 1569, 1528.

EXAMPLE 8

Synthesis of tetrahydro-4-{3-[4-(2-methyl-1H-imidazol-1-yl)-phenyl]-thio}-phenyl-2H-pyran-4-carboxamide, Using Solid NaOH Alone

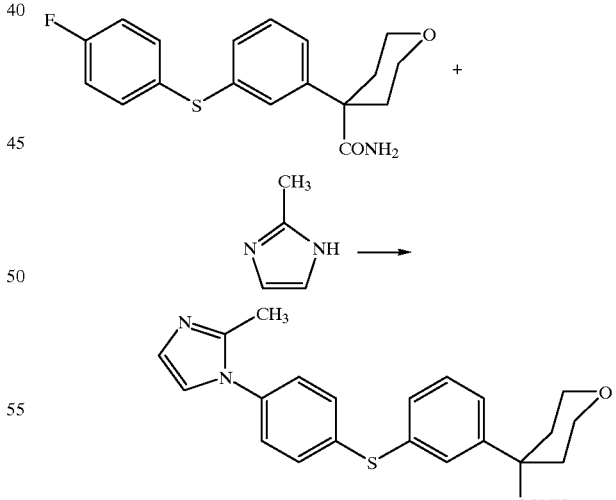

Tetrahydro-4-[3-(4-fluorophenyl)-thio]-phenyl-2H-pyran-4-carboxamide (6.5 g, 19.6 mmole, 1 eq), dimethylsulfoxide (65 ml, 10 vol), 2-methylimidazole (3.22 g, 39.23 mmole, 2.0 eq), and sodium hydroxide (1.57 g, 39.23 mmole, 2.0 eq), were added to a reaction flask set for boiling at reflux under a nitrogen atmosphere, and the reaction mixture was heated at 125–130° C. for 4–6 hours under nitrogen. After the reaction was completed, it was cooled (<30° C.) and quenched with water (65 ml, 10 vol), which resulted in the formation of a precipitate. An exotherm of 10–15° C. was observed during the water addition. The reaction slurry thus formed was cooled to room temperature (15–25° C.) and then granulated for 1 hour. The product was isolated by vacuum filtration and washed with water (80 ml, 12.3 vol). The product was dried overnight in a vacuum oven at 40–45°60 C. The amount of product obtained was 6.98 g, which represented a 90.4% yield. The analytical data for the product were as follows: mp 198–200° C.; m/z 396 (m+1); $^1$H NMR (300 MHz, DMSO) δ 7.41 (m, 10H), 7.12 (s, 1H), 6.93 (d, 1H), 3.75 (m, 2H), 3.48 (t, 2H), 2.48 (d, 2H), 2.3 (s, 3H), 1.75 (m, 2H); IR (drifts) $v_{max}$ 3402, 3301, 3123, 3096, 2971, 2930, 2880, 1680, 1663, 1622, 1593, 1569, 1528.

EXAMPLE 9

Mesylate salt formation

Methanol (640 ml, 40 vol), tetrahydro-4-[3-[4-(2-methyl-1H-imidazol-1-yl) phenyl]-thio]-phenyl-2H-pyran-4-carboxamide prepared by the method of Example 3 (16.0 g, 40.7 mmol, 1.0 eq.), activated charcoal, Darco KB-B (0.80 g) and filter aid, Celite (2.4 g) were added to a reaction flask set for boiling at reflux. The mixture was heated to reflux, approximately 66° C. to dissolve the organic substrate. The contents of the reaction flask were cooled to the temperature range 55–60° C., and the carbon and filter aid removed by filtration in the temperature range 55–60° C. The residue was washed with methanol (50 ml) and the wash combined with the original filtrate. The resultant clear combined filtrate and wash so obtained was concentrated by distillation at atmospheric pressure to a volume of approximately 700 ml. Methanesulfonic acid (4.1 g, 42.7 mmol, 1.05 eq.) was added to the concentrated methanol solution. The resultant solution was further concentrated by distillation at atmospheric pressure to a volume of about 250 ml and ethyl acetate (500 ml) was added in two aliquots, the net volume was reduced by distillation to 250 ml after each ethyl acetate addition. The resultant crystal slurry was cooled to room temperature 15–25° C. and granulated from 4–16 h in the temperature range 15–25° C. The white crystalline product was isolated by filtration and washed with ethyl acetate (135 ml), and dried under vacuum at 45–50° C. Yield 18.39 g, 92.3%. The salt so produced is characterized by an X-ray powder diffraction pattern with principal peaks set forth in Table 3 below:

TABLE (11.0.5)

| Peak Number | 2θ (Gk. Theta)° | d space (Å) | Peak Number | 2θ (Gk. Theta)° | d space (Å) |
|---|---|---|---|---|---|
| 1 | 6.5 | 13.6 | 20 | 24.0 | 3.7 |
| 2 | 9.1 | 9.7 | 21 | 24.5 | 3.6 |
| 3 | 13.3 | 6.6 | 22 | 25.4 | 3.5 |
| 4 | 14.2 | 6.2 | 23 | 26.1 | 3.4 |
| 5 | 14.4 | 6.1 | 24 | 26.7 | 3.3 |
| 6 | 15.1 | 5.9 | 25 | 27.7 | 3.2 |
| 7 | 15.4 | 5.7 | 26 | 28.6 | 3.1 |
| 8 | 16.0 | 5.5 | 27 | 29.3 | 3.0 |
| 9 | 16.7 | 5.3 | 28 | 30.0 | 3.0 |
| 10 | 17.2 | 5.1 | 29 | 30.5 | 2.9 |
| 11 | 17.8 | 5.0 | 30 | 31.7 | 2.8 |
| 12 | 18.2 | 4.8 | 31 | 32.8 | 2.7 |
| 13 | 19.0 | 4.7 | 32 | 33.8 | 2.6 |
| 14 | 19.9 | 4.4 | 33 | 35.3 | 2.5 |
| 15 | 21.0 | 4.2 | 34 | 36.0 | 2.5 |
| 16 | 22.0 | 4.0 | 35 | 36.7 | 2.4 |
| 17 | 22.3 | 4.0 | 36 | 37.6 | 2.4 |
| 18 | 22.9 | 3.9 | 37 | 39.2 | 2.3 |
| 19 | 23.6 | 3.8 | | | |

EXAMPLE 10

Recrystallization of tetrahydro-4-[3-[4-(2-methyl-1H-imidazol-1-yl) phenyl]thio]phenyl-2H-pyran-4-carboxamide Methanol (3200 ml, 40 vol), tetrahydro-4-[3-[4-(2-methyl-1H-imidazol-1-yl) phenyl]thio]phenyl-2H-pyran-4-carboxamide prepared by the method of Example 3, (80.2 g), activated charcoal, Darco KB-B (4.0 g) and filter aid, Celite (10 g) were added to a reaction flask set for boiling at reflux. The mixture was heated to reflux, approximately 66° C. to dissolve the organic substrate. The contents of the reaction flask were cooled to the temperature range 55–60° C., and the carbon and filter aid removed by filtration in the temperature range 55–60° C. The residue was washed with methanol (300 ml) and the wash combined with the original filtrate. The resultant clear combined filtrate and wash so obtained was concentrated by distillation at atmospheric pressure to a volume of approximately 1000 ml. The methanol concentrate so obtained was cooled to the temperature range 3–7° C. to establish product crystallization and granulated for 6–24 hours in this temperature range. The white product crystals were isolated by filtration and dried under vacuum at 40–45° C. Yield 70.3 g, 87.7%. mp 198–200° C.; m/z 396 (m+1); Spectral data as in Example 3.

EXAMPLE 11

Synthesis of tetrahydro-4-(3-bromophenyl)-2H-pyran-4-carboxamide

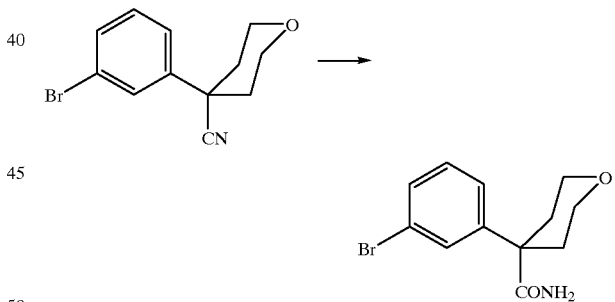

Propan-2-ol (100 ml), tetrahydro-4-(3-bromophenyl)-2H-pyran-4-nitrile (20.0 g, 0.075 mole, 1 eq.), potassium hydroxide (13.74 g, 0.245 mole, 3.26 eq.) were added to a reaction flask set for boiling at reflux under a nitrogen atmosphere, and the reaction mixture was heated with stirring at reflux, about 82° C. for 5–6 hours under nitrogen. After reaction completion, the mixture was cooled (<30° C.) and quenched with water (100 ml). The resultant slurry was filtered and the product residue, washed with water (30 ml), and dried under vacuum at 45–50° C. to yield a white solid. Yield 19.05 g, 89.2%. mp 245–247° C.; m/z 285 (m+1); $^1$H NMR (300 MHz, DMSO) δ 7.43 (m, 5H), 7.14 (s, 1H), 3.76 (d, 2H), 3.47 (t, 2H), 2.44 (d, 2H), 1.79 (m, 2H).; IR (drifts) $v_{max}$ 3363, 3174, 3062, 2973, 2935, 2879, 2828, 1685, 1631, 1588.

What is claimed is:

1. A process for preparing a compound of Formula (1.3.0):

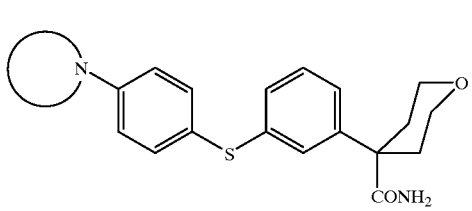
(1.3.0)

where
the moiety of following Formula (1.3.1):

(1.3.1)

is an electron deficient monocyclic or benzo-fused bicyclic N-heterocyclic group containing two nitrogen atoms, of Formula (1.3.2) (1.3.3), (1.3.4) or (1.3.5):

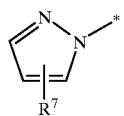
(1.3.2)

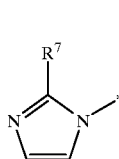
(1.3.3)

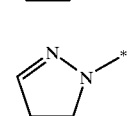
(1.3.4)

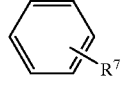
(1.3.5)

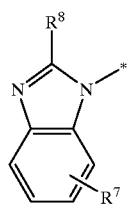

where
"*" is a symbol which represents the point of attachment of the moiety of Formula (1.3.2) (1.3.3), (1.3.4) or (1.3.5);

$R^7$ and $R^8$ are independently selected from the group consisting of H; straight or branched chain $(C_1-C_4)$ alkyl; and $(C_6-C_{10})$aryl; wherein said alkyl and aryl groups are substituted by 0 to 2 substituents selected from the group consisting of halo; hydroxy; cyano; amino; $(C_1-C_4)$alkyl; $(C_1-C_4)$alkoxy; $(C_1-C_4)$alkylthio; $(C_1-C_4)$halo-substituted alkyl; $(C_1-C_4)$halo-substituted alkoxy; $(C_1-C_4)$alkylamino; and di$(C_1-C_4)$alkylamino;

comprising:

(a) establishing a reaction mixture consisting of
(1) tetrahydro-4-[3-(4-fluorophenyl)thio]phenyl-2H-pyran-4-carboxamide of Formula (2.0.0):

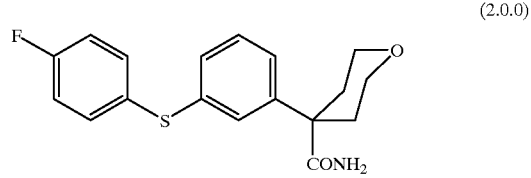
(2.0.0)

and
(2) an electron deficient monocyclic or benzo-fused bicyclic N-heterocycle containing two nitrogen atoms, of Formula (1.3.6) (1.3.7), (1.3.8) or (1.3.9):

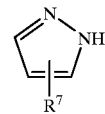
(1.3.6)

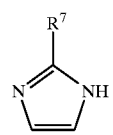
(1.3.7)

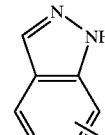
(1.3.8)

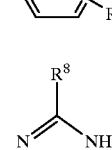
(1.3.9)

where $R^7$ and $R^8$ have the same meaning as set out above;

(3) in an aprotic solvent;
(4) in the presence of a carbonate of Formula (5.1.0):

$(M)_2\text{-}CO_3$ (5.1.0)

where M is an alkali metal, Group 1/Ia element, selected from the group consisting of lithium, Li; sodium, Na; potassium, K; rubidium, Rb; and cesium, Cs;

followed by (b) heating said reaction mixture, preferably at reflux, under a nitrogen atmosphere; whereby there is produced a compound of Formula (1.3.0).

* * * * *